(12) United States Patent
Maw et al.

(10) Patent No.: US 6,831,074 B2
(45) Date of Patent: Dec. 14, 2004

(54) PHARMACEUTICALLY ACTIVE COMPOUNDS

(75) Inventors: Graham Nigel Maw, Sandwich (GB); Christopher Gordon Barber, Sandwich (GB)

(73) Assignee: Pfizer Inc, New York, NY (US)

( * ) Notice: Subject to any disclaimer, the term of this patent is extended or adjusted under 35 U.S.C. 154(b) by 63 days.

(21) Appl. No.: 10/093,105

(22) Filed: Mar. 6, 2002

(65) Prior Publication Data

US 2002/0193388 A1 Dec. 19, 2002

Related U.S. Application Data

(60) Provisional application No. 60/290,734, filed on May 14, 2001.

(30) Foreign Application Priority Data

Mar. 16, 2001 (GB) .............................................. 0106631

(51) Int. Cl.⁷ ...................... A61K 31/33; A61K 31/495; C07D 47/100; C07D 487/00; C07D 49/00
(52) U.S. Cl. .................. 514/183; 514/247; 514/252.12; 514/257; 514/252.13; 514/252.14; 514/253.01; 544/245; 544/251; 544/252; 544/358; 544/360
(58) Field of Search ................................ 514/183, 248, 514/252.12, 252.13, 23.01, 255.05, 247, 252.14, 252.01, 257; 544/244, 249, 250, 245, 251, 252, 358, 360

(56) References Cited

FOREIGN PATENT DOCUMENTS

| EP | 623620 | * 11/1994 | |
|---|---|---|---|
| EP | 0995750 | 4/2000 | ......... C07D/487/04 |
| EP | 1176147 | 1/2002 | ......... C07D/487/04 |
| WO | 9954333 | * 10/1999 | |

OTHER PUBLICATIONS

Bischoff E. etal, PubMed Abstract 12597982,also cited as Urology, 61/2,464–7(2003).*
Arnavaz A. et al, PubMed Abstract 12694895, also cited as Psychiatry, 122/3,20709(2003).*
Modelska et al, PubMed Abstract 12548231, also cited as Am.J.Obstet. Gynecol., 188/1,286–93(2003).*
Conti et al, PubMed Abstract 10078540,also cited as Am.J. Cardio.,83/5A,29C–34C(1999).*
Joseph T. Ciylke et al, Science,219, 1184–1190(1983).*
Cecil's Textbook of Medicine, 2oth Edition, vol. 2, pp. 1992–1996.*
Cecil's Textbook of Medicine, 2oth Edition, vol. 1m pp. 1004–1010(1996).*
Uckun et al, Cureent Drug Targets, 1,59–71(2001).*

* cited by examiner

Primary Examiner—Richard L. Raymond
Assistant Examiner—Sudhaker B. Patel
(74) Attorney, Agent, or Firm—Peter C. Richardson; Gregg C. Benson; Martha G. Munchhof

(57) ABSTRACT

The present invention provides a compound of formula (I):

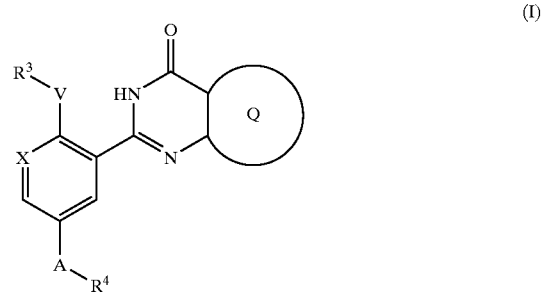

where Q is a group of formula:

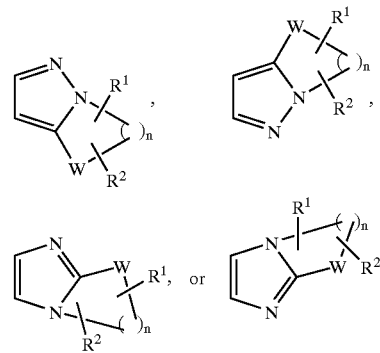

These compounds inhibit cyclic guanosine 3',5'-monophosphate phosphodiesterases (cGMP PDEs). More notably, the compounds are potent and selective inhibitors of the type 5 cyclic guanosine 3',5'-monophosphate phosphodiesterases and have utility therefore in a variety of therapeutic areas. In particular, the present compounds are of value for the curative or prophylactic treatment of mammalian sexual disorders.

14 Claims, No Drawings

PHARMACEUTICALLY ACTIVE COMPOUNDS

This application claims priority from G.B. Application 0106631.5 filed Mar. 16, 2001 and U.S. Provisional Application 60/290,734 filed May 14, 2001.

This invention relates to fused pyrazolo[4,3-d]pyrimidin-7-ones and pyrazolo [3,4-d] pyrimidin-4-ones and purinones which inhibit cyclic guanosine 3′,5′-monophosphate phosphodiesterases (cGMP PDEs). More notably, the compounds are potent and selective inhibitors of the type 5 cyclic guanosine 3′,5′-monophosphate phosphodiesterases and have utility therefore in a variety of therapeutic areas.

The present compounds are of value for the curative or prophylactic treatment of mammalian sexual disorders. In particular, the compounds are of value in the treatment of mammalian sexual dysfunctions such as male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD) as well as sexual dysfunction due to spinal cord injury or selective serotonin re-uptake inhibitor (SSRI) induced sexual dysfunction but, clearly, will be useful also for treating other medical conditions for which a potent and selective cGMP PDE5 inhibitor is indicated. Such conditions include premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, chronic asthma, allergic rhinitis, diseases and conditions of the eye such as glaucoma, optic neuropathy, macular degeneration, elevated intra-occular pressure, retinal or arterial occulsion and diseases characterised by disorders of gut motility, e.g. irritable bowel syndrome (IBS).

Further medical conditions for which a potent and selective cGMP PDE5 inhibitor is indicated, and for which treatment with compounds of the present invention may be useful, include pre-eclampsia, Kawasaki's syndrome, nitrate tolerance, multiple sclerosis, diabetic nephropathy, neuropathy including autonomic and peripheral neuropathy and in particular diabetic neuropathy and symptoms thereof (e.g. gastroparesis), peripheral diabetic neuropathy, Alzheimer's disease, acute respiratory failure, psoriasis, skin necrosis, cancer, metastasis, baldness, nutcracker oesophagus, anal fissure, haemorrhoids, hypoxic vasoconstriction, hypoxic vasoconstriction, diabetes, type 2 diabetes mellitus, the insulin resistance syndrome, insulin resistance, impaired glucose tolerance, as well as the stabilisation of blood pressure during haemodialysis.

Particularly preferred conditions include MED and FSD.

The prior art discloses a number of fused structures which are useful during the treatment of a number of disorders. For example, WO 94/15937 discloses the use of imidazopyrazinone derivatives as agonists/antagonists for GABA receptors. WO 99/02528 teaches the use of fused triazoles in anti-allergy/anti-inflammatory preparations. WO 98/14431 teaches the use of quinazolinyl piperazine derivatives for use in the treatment of arterial sclerosis and/or cancer. European Patent No 0 431 943 discloses the use of nitrogen containing fused spirocycles in the treatment of arrhythmia. European Patent No 0 623 620 teaches the use of pyrrolo pyrazine derivatives having activity on 5-HT3 receptors.

The present invention provides a compound of formula (I):

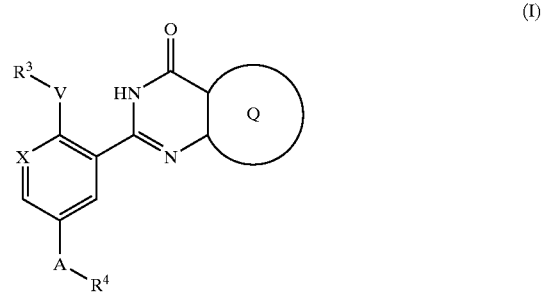

where Q is a group of formula:

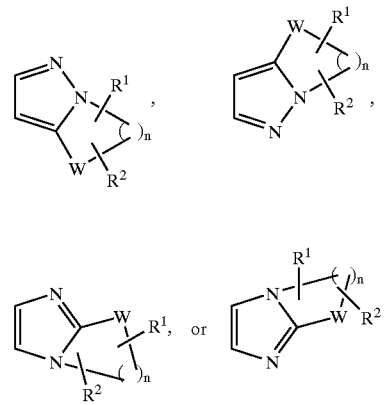

wherein
A represents $SO_2$, $C(O)$ or $CH(OH)$;
V represents O or $NR^5$;
W represents CHR, $CH_2$, —$(CH_2)_m$—CH(R)—, —C(O)—N($R^a$)—, —$(CH_2)_m$—O—, —$(CH_2)_m$—N($R^a$)—, —$(CH_2)_m$C(O)NH— or —$(CH_2)_m$NHC(O)—;
X represents CH or N;
m equals 1, 2 or 3;
n equals 1, 2, 3, 4 or 5 with the proviso that the ring containing W contains 5, 6, 7 or 8 atoms only;
R is hydrogen; halo; cyano; nitro; $C_1$ to $C_6$ alkyl; $C_3$ to $C_6$ cycloalkyl; $C_2$ to $C_6$ alkenyl; $C_1$ to $C_6$ alkylhet; $C_1$ to $C_6$ alkylaryl; aryl; het; $OR^b$; $OC(O)R^b$; $C(O)R^b$; $C(O)OR^b$; $NR^bC(O)NR^cR^d$; $NR^bC(O)OR^b$; $OC(O)NR^cR^d$; $C(O)NR^cR^d$; $NR^cR^d$; $SO_2NR^cR^d$;
$R^a$ represents hydrogen, $C_1$ to $C_6$ alkyl; $C_3$ to $C_6$ cycloalkyl; $C_2$ to $C_6$ alkenyl; $C_1$ to $C_6$ alkylhet; $C_1$ to $C_6$ alkylaryl; aryl; het; $C(O)OR^b$; $C(O)R^b$; $SO_2NR^cR^d$; or $SO_2R^b$;
wherein $R^b$, $R^c$ and $R^d$ independently represent hydrogen or $C_1$ to $C_6$ alkyl or $C_3$ to $C_6$ cycloalkyl or $C_2$ to $C_6$ alkenyl optionally substituted by halo; or $R^c$ and $R^d$ together with the nitrogen atom to which they are attached form a heterocyclic ring;
$R^1$ and $R^2$ are bonded to a carbon atom in the ring and independently represent hydrogen; halo; cyano; nitro; $C_1$ to $C_6$ alkyl; $C_3$ to $C_6$ cycloalkyl; $C_2$ to $C_6$ alkenyl; $C_1$ to $C_6$ alkylhet; $C_1$ to $C_6$ alkylaryl; aryl; het; $OR^b$;

OC(O)R$^b$; C(O)R$^b$; C(O)OR$^b$; NR$^b$C(O)NR$^c$R$^d$; NR$^b$C(O)OR$^b$; OC(O)NR$^c$R$^d$; C(O)NR$^e$R$^f$; NR$^e$R$^f$; SO$_2$NR$^e$R$^f$; or SO$_2$R$^b$;

wherein when R$^1$ or R$^2$ is C$_1$ to C$_6$ alkyl; C$_3$ to C$_6$ cycloalkyl; C$_2$ to C$_6$ alkenyl; C$_1$ to C$_6$ alkylhet; C$_1$ to C$_6$ alkylaryl; aryl; or het each such group may be optionally substituted and/or terminated with one or more substituents selected from the group comprising: halo; cyano; nitro; OR$^b$; OC(O)R$^b$; C(O)R$^b$; C(O)OR$^b$; NR$^b$C(O)NR$^c$R$^d$; NR$^b$C(O)OR$^b$; OC(O)NR$^c$R$^d$; C(O)NR$^e$R$^f$; NR$^e$R$^f$; SO$_2$NR$^e$R$^f$; or SO$_2$R$^b$;

wherein R$^e$ and R$^f$ independently represent H, C(O)R$^{12}$, SO$_2$R$^{17}$ or C$_1$–C$_6$ alkyl; or R$^e$ and R$^f$ together with the nitrogen atom to which they are bound can form a heterocyclic ring;

R$^3$, R$^4$ and R$^5$ independently represent H, C$_1$–C$_6$ alkyl, C$_3$ to C$_6$ cycloalkyl, Het, C$_1$–C$_6$ alkylHet, aryl or C$_1$–C$_6$ alkylaryl (which latter six groups may all be optionally substituted and/or terminated with one or more substituents selected from halo, cyano, nitro, OR$^6$, OC(O)R$^6$, C(O)R$^6$, C(O)OR$^6$, NR$^6$C(O)NR$^7$R$^8$, NR$^6$C(O)OR$^6$, OC(O)NR$^7$R$^8$, C(O)NR$^9$R$^{10}$, NR$^9$R$^{10}$, SO$_2$NR$^9$R$^{10}$, SO$_2$R$^{11}$, C$_1$–C$_6$ alkyl, C$_3$ to C$_6$ cycloalkyl, Het, C$_1$–C$_6$ alkylHet, aryl or C$_1$–C$_6$ alkylaryl wherein said latter six substituent and/or terminal groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$); or R$^3$ and R$^5$ together with the nitrogen atom to which they are bound can form a heterocyclic ring which is optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$; with the proviso that when A represents SO$_2$, R$^4$ does not represent hydrogen, C$_1$–C$_6$ alkyl, C$_1$–C$_6$ alkylhet, C$_1$–C$_6$ alkylaryl, aryl or a C-linked Het;

R$^6$ represents H, C$_1$–C$_6$ alkyl, C$_3$ to C$_6$ cycloalkyl, C$_2$–C$_6$ alkenyl, Het, C$_1$–C$_6$ alkylHet, aryl or C$_1$–C$_6$ alkylaryl (which latter seven groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$);

R$^7$ and R$^8$ independently represent H, C$_1$–C$_6$ alkyl, Het, C$_1$–C$_6$ alkylHet, aryl or C$_1$–C$_6$ alkylaryl (which latter five groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$); or R$^7$ and R$^8$ together with the nitrogen atom to which they are bound can form a heterocyclic ring;

R$^9$ and R$^{10}$ independently represent H, C(O)R$^6$, SO$_2$R$^{11}$, C$_1$–C$_6$ alkyl, Het, C$_1$–C$_6$ alkylHet, aryl or C$_1$–C$_6$ alkylaryl (which latter five groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$); or R$^9$ and R$^{10}$ together with the nitrogen atom to which they are bound can form a heterocyclic ring;

R$^{11}$ represents a C$_1$–C$_6$ alkyl, Het, C$_1$–C$_6$ alkylHet, aryl or C$_1$–C$_6$ alkylaryl group which is optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$;

R$^{12}$ represents H or C$_1$–C$_6$ alkyl or C$_3$–C$_6$ cycloalkyl;

R$^{13}$ and R$^{14}$ independently represent H or C$_1$–C$_6$ alkyl; or R$^{13}$ and R$^{14}$ together with the nitrogen atom to which they are bound can form a heterocyclic ring;

R$^{15}$ and R$^{16}$ independently represent H, C(O)R$^{12}$, SO$_2$R$^{17}$ or C$_1$–C$_6$ alkyl; or R$^{15}$ and R$^{16}$ together with the nitrogen atom to which they are bound can form a heterocyclic ring;

wherein when R$^7$ and R$^8$, or R$^9$ and R$^{10}$ together with the nitrogen atom to which they are bound form a heterocyclic ring, said heterocyclic ring optionally also includes an oxygen atom, and/or wherein said heterocyclic ring is optionally substituted and/or terminated with one or more substituents selected from: halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$;

R$^{17}$ represents C$_1$–C$_6$ alkyl; and

Het represents an optionally substituted four- to twelve-membered heterocyclic group, which group contains one or more heteroatoms selected from nitrogen, oxygen, sulfur and mixtures thereof, and wherein said heterocyclic ring is optionally substituted and/or terminated with one or more substituents selected from: halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$.

The compounds of formula (I) may thus be represented as follows:

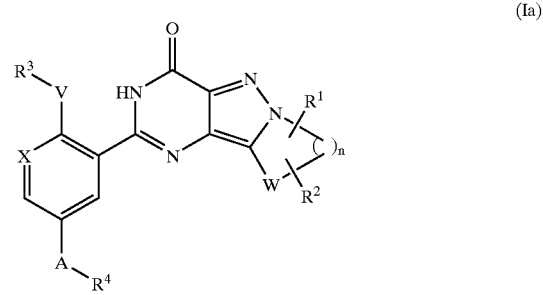

(Ia)

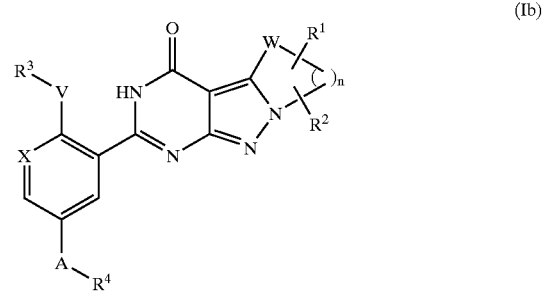

(Ib)

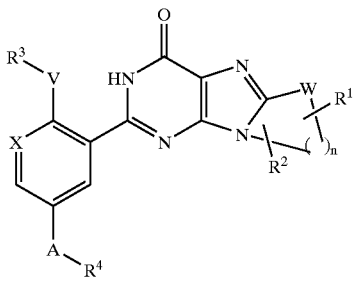

(Ic)

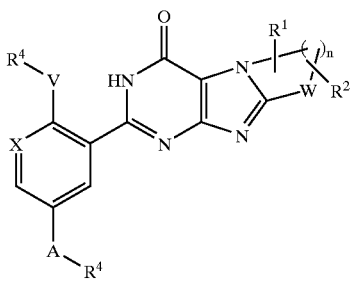

(Id)

For the avoidance of doubt the group —( )$_n$— as defined herein represents —(CH$_2$)$_n$—. Further R$^1$ and R$^2$ as defined herein are not bonded to carbon atoms which form part of the W group, but rather are bonded to ring carbon atoms from the —(CH$_2$)$_n$— group.

Preferably, A represents SO$_2$ or C(O).
Preferably, V represents O.
Preferably, W represents CHR, CH$_2$, —(CH$_2$)$_m$—CH(R)—, or —C(O)—N(R$^a$)—. Preferably R is hydrogen, methyl or ethyl.
Preferably, X represents N.
Preferably, n equals 2, 3, or 4. More preferably, n is 2 or 3.
Preferably, m equals 1.
Preferably, R$^1$ represents hydrogen or C$_1$ to C$_6$ alkyl.
Preferably, R$^2$ represents hydrogen or C$_1$ to C$_6$ alkyl.
Preferably, R$^3$ represents H or C$_1$–C$_6$ alkyl optionally substituted by C$_1$–C$_6$ alkoxy. More preferably, R$^3$ is ethyl, n-propyl, n-butyl, i-butyl, or 2-methoxyethoxy.
Preferably, when A represents SO$_2$, R$^4$ represents an N-linked Het which is substituted by C$_1$–C$_6$ alkyl (preferably methyl or ethyl). More preferably, R$^4$ is 4-ethylpiperazinyl, or 4-methylpiperazinyl.
Preferably, when A is C(O), R$^4$ represents C$_1$–C$_6$ alkyl, (preferably methyl).

The present invention also preferably provides a compound of the formula:

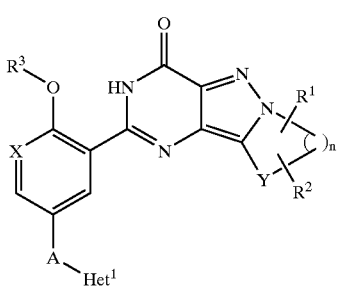

(Iaa)

wherein
A represents SO$_2$ or C(O) and more preferably A represents SO$_2$;

X represents CH or N;
Y represents W and is CH$_2$, —(CH$_2$)$_m$C(O)NH— or —(CH$_2$)$_m$NHC(O)—;
n equals 0, 1, 2, 3, 4 or 5;
m equals 0, 1, 2, 3 or 4;
Het$^1$ represents a piperazin-1-yl group having a substituent R$^6$ at the 4-position of the piperazinyl group wherein said piperazinyl group is optionally substituted with one or two C$_1$ to C$_4$ alkyl groups and is optionally in the form of its 4-N-oxide;
R$^1$ and R$^2$ independently represent hydrogen; C$_1$ to C$_6$ alkyl; C$_1$ to C$_6$ alkoxy; C$_3$ to C$_6$ cycloalkyl; C$_3$ to C$_6$ alkenyl; phenyl; heterocyclyl containing one or more atoms from N, S or O, wherein each of the aforementioned substituents may be further substituted with a group selected from —CN, —NO$_2$, —R$^6$, —S(O)$_2$R$^6$; —NR$^4$R$^5$, —OR$^6$; —OC(O)(C$_1$ to C$_4$ alkyl); halo;
R$^3$ represents C$_1$ to C$_6$ alkyl optionally substituted with one or two substituents selected from C$_3$ to C$_5$ cycloalkyl, hydroxy, C$_1$ to C$_4$ alkoxy, benzyloxy, NR$^4$R$^5$, phenyl, Het$^2$, Het$^3$, Het$^4$ or Het$^5$ wherein the C$_1$ to C$_6$ alkyl and C$_1$ to C$_4$ alkoxy groups may be optionally terminated by a haloalkyl group such as CF$_3$ and wherein the C$_3$–C$_5$ cycloalkyl group may be optionally substituted by C$_1$–C$_4$ alkyl, hydroxy or halo; C$_3$ to C$_6$ cycloalkyl; Het$^2$, Het$^3$, Het$^4$ or Het$^5$;
R$^4$ and R$^5$ each independently represents hydrogen; C$_1$ to C$_4$ alkyl optionally substituted with C$_3$ to C$_5$ cycloalkyl or C$_1$ to C$_4$ alkoxy, or, together with the nitrogen atom to which they are attached, form an azetidinyl, pyrrolidinyl, piperidinyl or morpholinyl group;
R$^6$ represents hydrogen; C$_1$ to C$_4$ alkyl optionally substituted with one or two substituents selected from halo, hydroxy, NR$^4$R$^5$, CONR$^4$R$^5$, phenyl optionally substituted with C$_1$ to C$_4$ alkyl or C$_1$ to C$_4$ alkoxy; C$_3$ to C$_6$ alkenyl; C$_1$ to C$_4$ haloalkoxy; or Het$^5$;
Het$^2$ represents an N-linked 4-, 5- or 6-membered nitrogen-containing heterocylic group optionally containing one or more further heteroatoms selected from S, N or O;
Het$^3$ represents a C-linked 5-membered heterocyclic group containing an O, S or N heteroatom optionally containing one or more further heteroatoms selected from N, O or S;
Het$^4$ represents a C-linked 6-membered heterocyclic group containing an O or S heteroatom optionally containing one or more further heteroatoms selected from O, S or N or Het$^3$ is a C-linked 6-membered heterocyclic group containing three N heteroatoms;
Het$^5$ represents a C-linked 4-, 5- or 6-membered heterocyclic group containing one, two or three heteroatoms selected from S, O or N; and
wherein any of said heterocyclic Het$^2$, Het$^3$, Het$^4$ or Het$^5$ may be saturated, partially unsaturated or aromatic and wherein any of said heterocyclic groups may be optionally substituted with one or more substituents selected from C$_1$ to C$_4$ alkyl, C$_3$ to C$_4$ alkenyl, C$_1$ to C$_4$ alkoxy, halo , CF$_3$, CO$_2$R$^6$, COR$^6$, SO$_2$R$^6$. NHR$^6$ or NHCOR$^6$ and/or wherein any of said heterocyclic groups is benzo-fused.

In the above definition of a compound of the formula (Ia) the following definitions are preferred.

Preferably in the compounds of the invention, Y, m and n are independently selected to form a 5–7 membered ring, more preferably a 6 membered ring. Even more preferably Y represents CH$_2$ and n equals 3.

Preferably in the compounds of the present invention, $R^1$ and $R^2$ each independently represent hydrogen, $C_1$–$C_6$ alkyl or $C_1$–$C_6$ alkoxy; more preferably $R^1$ and $R^2$ each independently represent hydrogen or $C_1$–$C_6$ alkyl.

Preferred compounds of the invention include those wherein $Het^1$ represents a 4-$R^6$-piperazin-1-yl group; and independently wherein $R^6$ represents a $C_1$ to $C_4$ alkyl group.

Further preferred compounds of the invention include those wherein $R^3$ represents $C_1$ to $C_6$ alkyl optionally substituted by $C_1$ to $C_4$ alkoxy.

Particularly preferred examples of the compounds of the formula (I) are:

2-{2-Ethoxy-5-[(4-ethyl-1-piperazinyl)sulphonyl]-3-pyridinyl}-3,7,8,9-tetrahydro-4H-pyrrolo[2',1':5,1]pyrazolo[4,3-d]pyrimidin-4-one 2-{2-Ethoxy-5-[(4-ethyl-1-piperazinyl)sulfonyl]-3-pyridinyl}-7,8,9,10-tetrahydropyrido[2',1':5,1]pyrazolo[4,3-d]pyrimidin-4(3H)-one 2-{2-Ethoxy-5-[(4-ethyl-1-piperazinyl)sulfonyl]-3-pyridinyl}-10-methyl-7,8,9,10-tetrahydropyrido[2',1':5,1]pyrazolo[4,3-d]pyrimidin-4(3H)-one (9R)-2-{2-Ethoxy-5-[(4-ethyl-1-piperazinyl)sulfonyl]-3-pyridinyl}-9-methyl-7,8,9,10-tetrahydropyrido[2',1':5,1]pyrazolo[4,3-d]pyrimidin-4(3H)-one 2-{2-Ethoxy-5-[(4-ethyl-1-piperazinyl)sulfonyl]-3-pyridinyl}-9-ethyl-8,9-dihydropyrazino[2',1':5,1]pyrazolo[4,3-d]pyrimidine-4,10(3H,7H)-dione 2-{5-[(4-Ethyl-1-piperazinyl)sulfonyl]-2-n-propoxy-3-pyridinyl}-7,8,9,10-tetrahydropyrido[2',1':5,1]pyrazolo[4,3-d]pyrimidin-4(3H)-one 2-{5-[(4-Ethyl-1-piperazinyl)sulfonyl]-2-(2-methoxyethoxy)-3-pyridinyl}-7,8,9,10-tetrahydropyrido[2',1':5,1]pyrazolo[4,3-d]pyrimidin-4(3H)-one 2-{5-[(4-Ethyl-1-piperazinyl)sulfonyl]-2-n-propoxy-3-pyridinyl}-10-methyl-7,8,9,10-tetrahydropyrido[2',1':5,1]pyrazolo[4,3-d]pyrimidin-4(3H)-one 2-{5-[(4-Ethyl-1-piperazinyl)sulfonyl]-2-(2-methoxyethoxy)-3-pyridinyl}-10-methyl-7,8,9,10-tetrahydropyrido[2',1':5,1]pyrazolo[4,3-d]pyrimidin-4(3H)-one (9R)-2-{5-[(4-Ethyl-1-piperazinyl)sulfonyl]-2-(2-methoxyethoxy)-3-pyridinyl}-9-methyl-7,8,9,10-tetrahydropyrido[2',1':5,1]pyrazolo[4,3-d]pyrimidin-4(3H)-one 2-[5-[(4-Ethyl-1-piperazinyl)sulfonyl]-2-(2-methoxyethoxy)-3-pyridinyl]-3,7,8,9,10,11-hexahydro-4H-pyrimido[5',4':3,4]pyrazolo[1,5-a]azepin-4-one 2-[5-[(4-Ethyl-1-piperazinyl)sulfonyl]-2-(2-methoxyethoxy)-3-pyridinyl]-11-methyl-3,7,8,9,10,11-hexahydro-4H-pyrimido[5',4':3,4]pyrazolo[1,5-a]azepin-4-one 2-{5-[(4-Ethyl-1-piperazinyl)sulfonyl]-2-n-propoxy-3-pyridinyl}-9-ethyl-8,9-dihydropyrazino[2',1':5,1]pyrazolo[4,3-d]pyrimidine-4,10(3H,7H)-dione 2-{2-n-Butoxy-5-[(4-ethyl-1-piperazinyl)sulfonyl]-3-pyridinyl}-9-ethyl-8,9-dihydropyrazino[2',1':5,1]pyrazolo[4,3-d]pyrimidine-4,10(3H,7H)-dione 2-{2-n-Butoxy-5-[(4-ethyl-1-piperazinyl)sulfonyl]-3-pyridinyl}-8,9-dihydropyrazino[2',1':5,1]pyrazolo[4,3-d]pyrimidine-4,10(3H,7H)-dione (−)-2-{2-Ethoxy-5-[(4-ethyl-1-piperazinyl)sulfonyl]-3-pyridinyl}-10-methyl-7,8,9,10-tetrahydropyrido[2',1':5,1]pyrazolo[4,3-d]pyrimidin-4(3H)-one, and (+)-2-{2-Ethoxy-5-[(4-ethyl-1-piperazinyl)sulfonyl]-3-pyridinyl}-10-methyl-7,8,9,10-tetrahydropyrido[2',1':5,1]pyrazolo[4,3-d]pyrimidin-4(3H)-one 2-{5-[(4-Ethyl-1-piperazinyl)sulfonyl]-2-n-propoxy-3-pyridinyl}-10-methyl-7,8,9,10-tetrahydropyrido[2',1':5,1]pyrazolo[4,3-d]pyrimidin-4(3H)-one 2-{5-[(4-Ethyl-1-piperazinyl)sullenly]-2-n-propoxy-3-pyridinyl}-10-methyl-7,8,9,10-tetrahydropyrido[2',1':5,1]pyrazolo[4,3-d]pyrimidin-4(3H)-one (−)-2-{5-[(4-Ethyl-1-piperazinyl)sulfonyl]-2-(2-methoxyethoxy)-3-pyridinyl}-10-methyl-7,8,9,10-tetrahydropyrido[2',1':5,1]pyrazolo[4,3-d]pyrimidin-4(3H)-one (+)-2-{5-[(4-Ethyl-1-piperazinyl)sulfonyl]-2-(2-methoxyethoxy)-3-pyridinyl}-10-methyl-7,8,9,10-tetrahydropyrido[2',1':5,1]pyrazolo[4,3-d]pyrimidin-4(3H)-one 2-(5-Acetyl-2-ethoxy-3-pyridinyl)-10-methyl-7,8,9,10-tetrahydropyrido [2',1':5,1]pyrazolo[4,3-d]pyrimidin-4(3H)-one 2-(5-Acetyl-2-isobutoxy-3-pyridinyl)-10-methyl-7,8,9,10-tetrahydropyrido [2',1':5,1]pyrazolo[4,3-d]pyrimidin-4(3H)-one The compounds of the formula (I) can be prepared using conventional procedures such as by the following illustrative methods in which all groups or substituents are as previously defined for a compound of the formula (I) unless otherwise stated.

Thus, in a further aspect, the present invention provides processes for the preparation of compounds of formulae (I), their pharmaceutically and veterinarily acceptable salts, and pharmaceutically and veterinarily acceptable solvates of either entity, as illustrated below.

It will be appreciated by persons skilled in the art that, within certain of the processes described, the order of the synthetic steps employed may be varied and will depend inter alia on factors such as the nature of other functional groups present in a particular substrate, the availability of key intermediates and the protecting group strategy (if any) to be adopted. Clearly, such factors will also influence the choice of reagent for use in the said synthetic steps.

It will also be appreciated that various standard substituent or functional group interconversions and transformations within certain compounds of formulae (I) will provide other compounds of formulae (I). Examples include alkoxide exchange at the 2-position of the 5-(pyridin-3-yl) substituent, amine exchange at the 2-position of the 5-(pyridin-3-yl) substituent, reactions at a nitrogen containing substituent, such as reductive alkylation, acetamide formation or sulphonamide formation, and reduction of a nitro functionality to provide an amino group. The deprotection and transformations described herein and as illustrated in the Examples and Preparations sections may be effected in a "one-pot" procedure.

According to a further aspect of the invention there is provided a process for the preparation of a compound of formula (I) as defined above, the process comprising cyclising a compound of general formula (IX):

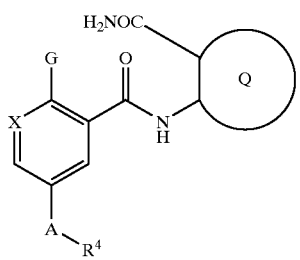

(IX)

wherein G is $OR^3$ or $NR^3R^5$ or X' and wherein A, Q, V, W, X, n, m, and $R^1$ to $R^{17}$ are as defined hereinbefore and X' is a leaving group.

According to a further aspect of the invention there is provided a process for the preparation of a compound of formula (IX), the process comprising a coupling reaction between a compound of formula (VII):

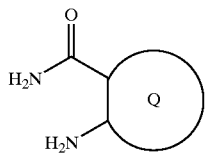

(VII)

wherein A etc. are as previously defined, with a compound of formula (XA), (XB) or (XC) respectively:

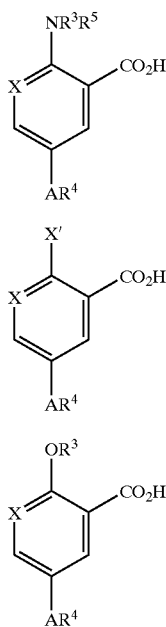

(XA)

(XB)

(XC)

wherein A, $R^3$, $R^4$, $R^5$, Q, X and X' are as previously defined.

According to a further aspect of the invention, there is provided a process for the preparation of a compound of formula (I), the process comprising functional group inter-conversion of an alternative compound of formula (I).

Certain of the intermediates formed in the processes used to make compounds of formula (I) are novel and these novel intermediates are also within the scope of the present invention.

According to a further aspect of the present invention, there is provided a compound of formula (IXA), (IXB) or (IXC):

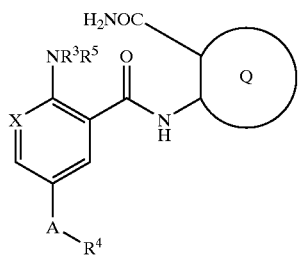

(IXA)

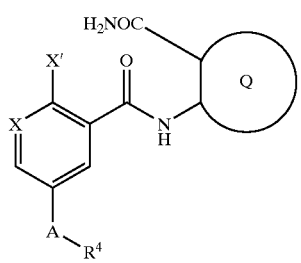

(IXB)

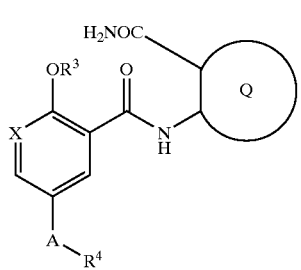

(IXC)

wherein A etc are as defined above.

According to a further aspect of the present invention, there is provided a compound of formula (VII):

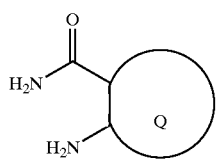

(VII)

wherein Q etc are as defined above.

According to a further aspect of the present invention, there is provided a compound of formula (XA), (XB) or (XC):

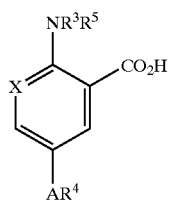

(XA)

-continued

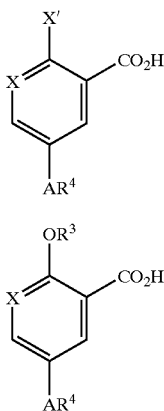

wherein A etc are as defined above.

Throughout the description, the like-numbered substituent groups in the various different formulae have the same meanings as for the compounds of formula (I) unless stated otherwise. Furthermore, unless otherwise stated, those substituents represent the same preferred subgroups as defined in respect of preferred embodiments of the compounds of formula (I).

Throughout the above definitions, "halo" means fluoro, chloro, bromo or iodo. Alkyl, alkoxy, alkenyl, alkylene and alkenylene groups containing the requisite number of carbon atoms, except where indicated, can be unbranched or branched chains.

The term "aryl", when used herein, includes optionally substituted six- to ten-membered carbocyclic aromatic groups which may be mono- or bicyclic, such as phenyl and naphthyl.

The pharmaceutically acceptable salts of the compounds of the formula (I) include the acid addition and the base salts thereof.

The pharmaceutically or veterinarily acceptable salts of the compounds of the invention which contain a basic centre are, for example, non-toxic acid addition salts formed with inorganic acids such as hydrochloric, hydrobromic, hydroiodic, sulphuric and phosphoric acid, with carboxylic acids or with organo-sulphonic acids. Examples include the HCl, HBr, HI, sulphate or bisulphate, nitrate, phosphate or hydrogen phosphate, acetate, benzoate, succinate, saccharate, fumarate, maleate, lactate, citrate, tartrate, gluconate, camsylate, methanesulphonate, ethanesulphonate, benzenesulphonate, p-toluenesulphonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc and diethanolamine salts. For a review on suitable pharmaceutical salts see Berge et al, J. Pharm, Sci., 66, 1–19, 1977.

The pharmaceutically acceptable solvates of the compounds of the invention include the hydrates thereof.

Also included within the scope of the compound and various salts of the invention are polymorphs thereof.

A compound of the formula (I) contains one or more asymmetric carbon atoms and therefore exists in two or more stereoisomeric forms. Where a compound of the formula (I) contains an alkenyl or alkenylene group, cis (E) and trans (Z) isomerism may also occur. The present invention includes the individual stereoisomers of the compounds of the formula (I) and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the invention.

The present invention also includes all suitable isotopic variations of a compound of the formula (I) or a pharmaceutically acceptable salt thereof. An isotopic variation of a compound of the formula (I) or a pharmaceutically acceptable salt thereof is defined as one in which at least one atom is replaced by an atom having the same atomic number but an atomic mass different from the atomic mass usually found in nature. Examples of isotopes that can be incorporated into compounds of the formula (I) and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the compounds of the formula (I) and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of formula (I) and pharmaceutically acceptable salts thereof of this invention can generally be prepared by conventional procedures such as by the illustrative methods or by the preparations described in the Examples and Preparations hereafter using appropriate isotopic variations of suitable reagents.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula (I) may act as prodrugs of other compounds of formula (I).

All protected derivatives, and prodrugs, of compounds of formula (I) are included within the scope of the invention. Examples of suitable pro-drugs for the compounds of the present invention are described in Drugs of Today, Volume 19, Number 9, 1983, pp 499–538 and in Topics in Chemistry, Chapter 31, pp 306–316 and in "Design of Prodrugs" by H. Bundgaard, Elsevier, 1985, Chapter 1 (the disclosures in which documents are incorporated herein by reference).

Also included within the scope of the invention are radiolabelled derivatives of compounds of formula I which are suitable for biological studies.

It will further be appreciated by those skilled in the art, that certain moieties, known to those skilled in the art as "pro-moieties", for example as described by H. Bundgaard in "design of Prodrugs" (the disclosure in which document is incorporated herein by reference) may be placed on appropriate functionalities when such functionalities are present within compounds of formula (I).

Preferred prodrugs for compounds of formula (I) include: esters, carbonate esters, hemi-esters, phosphate esters, nitro esters, sulfate esters, sulphoxides, amides, carbamates, azo-compounds, phosphamides, glycosides, ethers, acetals and ketals.

Medical Use

The compounds of the invention are useful because they possess pharmacological activity in animals, especially mammals, including humans. They are therefore indicated as pharmaceuticals, as well as for use as animal medicaments.

According to a further aspect of the invention there is provided the compounds of the invention for use as pharmaceuticals, and for use as animal medicaments.

In particular, compounds of the invention have been found to be potent and selective inhibitors of cGMP PDEs, such as cGMP PDE5, for example as demonstrated in tests described below, and thus are useful in the treatment of medical conditions in humans, and in animals, in which cGMP PDEs, such as cGMP PDE5, are indicated, and in which inhibition of cGMP PDEs, such as cGMP PDE5, is desirable.

By the term "treatment", we include therapeutic (curative), palliative or prophylactic treatment.

Thus according to a further aspect of the invention there is provided the use of the compounds of the invention in the manufacture of a medicament for the treatment of a medical condition in which a cGMP PDE (e.g. cGMP PDE5) is indicated. There is further provided the use of the compounds of the invention in the manufacture of a medicament for the treatment of a medical condition in which the inhibition of a cGMP PDE (e.g. cGMP PDE) is desirable or required.

The compounds of the invention are thus expected to be useful for the curative, palliative or prophylactic treatment of mammalian sexual disorders. In particular, the compounds are of value in the treatment of mammalian sexual dysfunctions such as male erectile dysfunction (MED), impotence, female sexual dysfunction (FSD), clitoral dysfunction, female hypoactive sexual desire disorder, female sexual arousal disorder, female sexual pain disorder, female orgasmic dysfunction (FSOD) as well as sexual dysfunction due to spinal cord injury but, clearly, will be useful also for treating other medical conditions for which a potent and selective cGMP PDE5 inhibitor is indicated. Such conditions include premature labour, dysmenrrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, artherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, allergic rhinitis, glaucoma, and diseases characterised by disorders of gut motility, e.g. irritable bowel syndrome (IBS).

Further medical conditions for which a potent and selective cGMP PDE5 inhibitor is indicated, and for which treatment with compounds of the present invention may be useful in pre-eclampsia, Kawasaki's syndrome, nitrate tolerance, multiple sclerosis, diabetic nephropathy, peripheral diabetic neuropathy, Alzheimer's disease, acute respiratory failure, psoriasis, skin necrosis, cancer, metastasis, baldness, nutcracker oesophagus, anal fissure, haemorrhoids and hypoxic vasoconstriction.

Particularly preferred conditions include MED and FSD.

Thus the invention provides a method of treating or preventing a medical condition for which a cGMP PDE5 inhibitor is indicated, in an animal (e.g. a mammal, including a human being), which comprises administering a therapeutically effective amount of a compound of the invention to a mammal in need of such treatment.

The biological activities of the compounds of the present invention were determined by the following test methods.

Bioavailability

Preferably the compounds of the invention are orally bioavailable. Oral bioavailablity refers to the proportion of an orally administered drug that reaches the systemic circulation. The factors that determine oral bioavailability of a drug are dissolution, membrane permeability and metabolic stability. Typically, a screening cascade of firstly in vitro and then in vivo techniques is used to determine oral bioavailablity.

Dissolution, the solubilisation of the drug by the aqueous contents of the gastro-intestinal tract (GIT), can be predicted from in vitro solubility experiments conducted at appropriate pH to mimic the GIT. Preferably the compounds of the invention have a minimum solubility of 50 mcg/ml. Solubility can be determined by standard procedures known in the art such as described in Adv. Drug Deliv. Rev. 23, 3–25, 1997.

Membrane permeability refers to the passage of the compound through the cells of the GIT. Lipophilicity is a key property in predicting this and is defined by in vitro Log $D_{7.4}$ measurements using organic solvents and buffer. Preferably the compounds of the invention have a Log $D_{7.4}$ of −2 to +4, more preferably −1 to +2. The log D can be determined by standard procedures known in the art such as described in J. Pharm. Pharmacol. 1990, 42:144.

Cell monolayer assays such as $CaCo_2$ add substantially to prediction of favourable membrane permeability in the presence of efflux transporters such as p-glycoprotein, so-called caco-2 flux. Preferably, compounds of the invention have a caco-2 flux of greater than $2 \times 10^{-6} cms^{-1}$, more preferably greater than $5 \times 10^{-6} cms^{-1}$. The caco flux value can be determined by standard procedures known in the art such as described in J. Pharm. Sci, 1990, 79, 595–600

Metabolic stability addresses the ability of the GIT or the liver to metabolise compounds during the absorption process: the first pass effect. Assay systems such as microsomes, hepatocytes etc are predictive of metabolic liability. Preferably the compounds of the Examples show metabolic stablity in the assay system that is commensurate with an hepatic extraction of less then 0.5. Examples of assay systems and data manipulation are described in Curr. Opin. Drug Disc. Devel., 201, 4, 36–44, Drug Met. Disp.,2000, 28, 1518–1523

Because of the interplay of the above processes further support that a drug will be orally bioavailable in humans can be gained by in vivo experiments in animals. Absolute bioavailability is determined in these studies by administering the compound separately or in mixtures by the oral route. For absolute determinations (% absorbed) the intravenous route is also employed. Examples of the assessment of oral bioavailability in animals can be found in Drug Met. Disp., 2001, 29, 82–87; J. Med Chem, 1997, 40, 827–829, Drug Met. Disp.,1999, 27, 221–226

Phosphodiesterase (PDE) Inhibitory Activity

In vitro PDE inhibitory activities against cyclic guanosine 3',5'-monophosphate (CGMP) and cyclic adenosine 3',5'-monophosphate (cAMP) phosphodiesterases were determined by measurement of their $IC_{50}$ values (the concentration of compound required for 50% inhibition of enzyme activity). The compounds of the present invention were determined to have $IC_{50}$ values between 0.5 and 250 nM. The results show that these compounds are potent and selective inhibitors of cGMP-specific PDE5.

The required PDE enzymes were isolated from a variety of sources, including human corpus cavernosum, human and rabbit platelets, human cardiac ventricle, human skeletal muscle and bovine retina, essentially by the method of W. J. Thompson and M. M. Appleman (Biochem., 1971, 10, 311). In particular, the cGMP-specific PDE (PDE5) and the cGMP-inhibited cAMP PDE (PDE3) were obtained from human corpus cavernosum tissue, human platelets or rabbit platelets; the cGMP-stimulated PDE (PDE2) was obtained from human corpus cavernosum; the calcium/calmodulin (Ca/CAM)-dependent PDE (PDE1) from human cardiac ventricle; the cAMP-specific PDE (PDE4) from human skeletal muscle; and the photoreceptor PDE (PDE6) from bovine retina. Phosphodiesterases 7–11 were generated from full length human recombinant clones transfected into SF9 cells.

Assays were performed either using a modification of the "batch" method of W. J. Thompson et al. (Biochem., 1979, 18, 5228) or using a scintillation proximity assay for the direct detection of AMP/GMP using a modification of the protocol described by Amersham pic under product code TRKQ7090/7100. In summary, the effect of PDE inhibitors was investigated by assaying a fixed amount of enzyme in the presence of varying inhibitor concentrations and low substrate, (cGMP or cAMP in a 3:1 ratio unlabelled to [$^3$H]-labeled at a conc ~1/3 $K_m$) such that $IC_{50} \Box K_i$. The final assay volume was made up to 100 $\Phi$l with assay buffer [20 mM Tris-HCl pH 7.4, 5 mM $MgCl_2$, 1 mg/ml bovine serum albumin]. Reactions were initiated with enzyme, incubated for 30–60 min at 30° C. to give <30% substrate turnover and terminated with 50 $\Phi$l yttrium silicate SPA beads (containing 3 mM of the respective unlabelled cyclic nucleotide for PDEs 9 and 11). Plates were re-sealed and shaken for 20 min, after which the beads were allowed to settle for 30 min in the dark and then counted on a TopCount plate reader (Packard, Meriden, Conn.) Radioactivity units were converted to % activity of an uninhibited control (100%), plotted against inhibitor concentration and inhibitor $IC_{50}$ values obtained using the 'Fit Curve' Microsoft Excel extension. Results from these tests show that the compounds of the present invention are potent and selective inhibitors of cGMP-specific PDE5.

Functional Activity

This was assessed in vitro by determining the capacity of a compound of the invention to enhance sodium nitroprusside-induced relaxation of pre-contracted rabbit corpus cavernosum tissue strips, as described by S. A. Ballard et al. (Brit. J. Pharmacol., 1996, 118 (suppl.), abstract 153P).

In vivo Activity

Compounds were screened in anaesthetised dogs to determine their capacity, after i.v. administration, to enhance the pressure rises in the corpora cavernosa of the penis induced by intracavernosal injection of sodium nitroprusside, using a method based on that described by Trigo-Rocha et al. (Neurourol. and Urodyn., 1994, 13, 71).

The present invention additionally comprises the combination of a cGMP PDE5i of formula (I) or (Iaa) as defined herein for the treatment of sexual dysfunction of any other condition for which a potent and selective PDE5l is indicated with one or more additional active agents.

Thus a further aspect of the invention provides a pharmaceutical combination (for simultaneous, separate or sequential administration) comprising a cGMP PDE5 inhibitor according to the present invention and:

The present invention additionally comprises the combination of a cGMP $PDE_5$ inhibitor compound of the general formula (I) with:

(1) one or more naturally occurring or synthetic prostaglandins or esters thereof. Suitable prostaglandins for use herein include compounds such as alprostadil, prostaglandin $E_1$, prostaglandin $E_0$, 13, 14-dihydroprostaglandin $E_1$, prostaglandin $E_2$, eprostinol, natural synthetic and semi-synthetic prostaglandins and derivatives thereof including those described in U.S. Pat. No. 6,037,346 issued on 14th Mar. 2000 and incorporated herein by reference, $PGE_0$, $PGE_1$, $PGA_1$, $PGB_1$, $PGF_1$ α, 19-hydroxy $PGA_1$, 19-hydroxy-$PGB_1$, $PGE_2$, $PGB_2$, 19-hydroxy-$PGA_2$, 19-hydroxy-$PGB_2$, $PGE_3α$, carboprost tromethamine dinoprost, tromethamine, dinoprostone, lipo prost, gemeprost, metenoprost, sulprostune, tiaprost and moxisylate; and/or (2) one or more α-adrenergic receptor antagonist compounds also known as α-adrenoceptors or α-receptors or α-blockers. Suitable compounds for use herein include: the α-adrenergic receptors as described in PCT application WO99/30697 published on 14th Jun. 1998, the disclosures of which relating to α-adrenergic receptors are incorporated herein by reference and include, selective $α_1$-adrenoceptors or $α_2$-adrenoceptors and non-selective adrenoceptors, suitable $α_1$-adrenoceptors include: phentolamine, phentolamine mesylate, trazodone, alfuzosin, indoramin, naftopidil, tamsulosin, dapiprazole, phenoxybenzamine, idazoxan, efaraxan, yohimbine, rauwolfa alkaloids, Recordati 15/2739, SNAP 1069, SNAP 5089, RS17053, SL 89.0591, doxazosin, terazosin, abanoquil and prazosin; $α_2$-blockers from U.S. Pat. No. 6,037,346 [14th Mar. 2000] dibenamine, tolazoline, trimazosin and dibenamine; α-adrenergic receptors as described in U.S. Pat. Nos.: 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference; $α_2$-Adrenoceptors include: clonidine, papaverine, papaverine hydrochloride, optionally in the presence of a cariotonic agent such as pirxamine; and/or (3) one or more NO-donor (NO-agonist) compounds. Suitable NO-donor compounds for use herein include organic nitrates, such as mono- di or tri-nitrates or organic nitrate esters including glyceryl brinitrate (also known as nitroglycerin), isosorbide 5-mononitrate, isosorbide dinitrate, pentaerythritol tetranitrate, erythrityl tetranitrate, sodium nitroprusside (SNP), 3-morpholinosydnonimine molsidomine, S-nitroso-N-acetyl penicilliamine (SNAP) S-nitroso-N-glutathione (SNO-GLU), N-hydroxy-L-arginine, amylnitrate, linsidomine, linsidomine chlorohydrate, (SIN-1) S-nitroso-N-cysteine, diazenium diolates, (NONOates), 1,5-pentanedinitrate, L-arginene, ginseng, zizphi fructus, molsidomine, Re-2047, nitrosylated maxisylyte derivatives such as NMI-678-

11 and NMI-937 as described in published PCT application WO 0012075; and/or (4) one or more potassium channel openers. Suitable potassium channel openers for use herein include nicorandil, cromokalim, levcromakalim, lemakalim, pinacidil, cliazoxide, minoxidil, charybdotoxin, glyburide, 4-amini pyridine, BaCl$_2$; and/or (5) one or more dopaminergic agents, preferably apomorphine or a selective D2, D3 or D2/D3 agonist such as pramipexol and ropirinol (as claimed in WO 0023056), L-Dopa or carbi dopa, PNU 95666 (as claimed in WO 00 40226); and/or (6) one or more vasodilator agents. Suitable vasodilator agents for use herein include nimodepine, pinacidil, cyclandelate, isoxsuprine, chloroprumazine, halo peridol, Rec 15/2739, trazodone; and/or (7) one or more thromboxane A2 agonists; and/or (8) one or more ergot alkoloids; Suitable ergot alkaloids are described in U.S. Pat. No. 6,037,346 issued on 14th Mar. 2000 and include acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride; and/or (9) one or more compounds which modulate the action of atrial natruretic factor (also known as atrial naturetic peptide), B and C type naturetic factors such as inhibitors or neutral endopeptidase; and/or

(10) one or more compounds which inhibit angiotensin-converting enzyme such as enapril, and one or more combined inhibitors of angiotensin-converting enzyme and neutral endopeptidase such as omapatrilat; and/or

(11) one or more angiotensin receptor antagonists such as losartan; and/or

(12) one or more substrates for NO-synthase, such as L-arginine; and/or

(13) one or more calcium channel blockers such as amlodipine; and/or

(14) one or more antagonists of endothelin receptors and inhibitors or endothelin-converting enzyme; and/or

(15) one or more cholesterol lowering agents such as statins (e.g. atorvastatin/Lipitor-trade mark) and fibrates; and/or

(16) one or more antiplatelet and antithrombotic agents, e.g. tPA, uPA, warfarin, hirudin and other thrombin inhibitors, heparin, thromboplastin activating factor inhibitors; and/or

(17) one or more insulin sensitising agents such as rezulin and hypoglycaemic agents such as glipizide; and/or

(18) one or more COX 2 inhibitors; and/or

(19) pregabalene; and/or

(20) gabapentene; and/or

(21) one or more acetylcholinesterase inhibitors such as donezipil; and/or

(22) one or more steroidal anti-inflammatory agents; and/or

(23) one or more estrogen agonists and/or estrogen antagonists, preferably raloxifene or lasofoxifene, (−)-cis-6-phenyl-5-[4-(2-pyrrolidin-1-yl-ethoxy)-phenyl]-5,6,7,8-tetrahydronaphthalene-2-ol and pharmaceutically acceptable salts thereof (compound A below) the preparation of which is detailed in WO 96/21656.

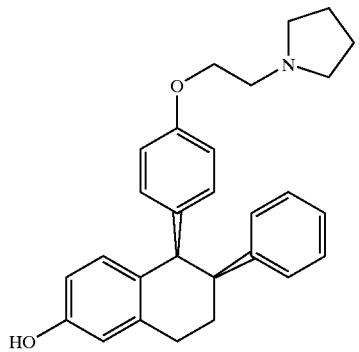

(24) one or more one or more of a further PDE inhibitor, more particularly a PDE 2, 4, 7 or 8 inhibitor, preferably PDE2 inhibitor, said inhibitors preferably having an IC50 against the respective enzyme of less than 100 nM: and/or

(25) one or more of an NPY (neuropeptide Y) inhibitor, more particularly NPY1 or NPY5 inhibitor, preferably NPY1 inhibitor, preferably said NPY inhibitors (including NPY Y1 and NPY Y5) having an IC50 of less than 100 nM, more preferably less than 50 nM, suitable NPY and in particular NPY1 inhibitor compounds are described in EP-A-1097718; and/or

(26) one or more of vasoactive intestinal peptide (VIP), VIP mimetic, more particularly mediated by one or more of the VIP receptor subtypes VPAC1, VPAC or PACAP (pituitary adenylate cyclase activating peptide), one or more of a VIP receptor agonist or a VIP analogue (eg Ro-125-1553) or a VIP fragment, one or more of a α-adrenoceptor antagonist with VIP combination (eg Invicorp, Aviptadil); and/or

(27) one or more of a melanocortin receptor agonist or modulator or melanocortin ehancer, such as melanotan II, PT-14, PT-141 or compounds claimed in WO-09964002, WO-00074679, WO-09955679, WO-00105401, WO-00058361, WO-00114879, WO-00113112, WO-09954358; and/or

(28) one or more of a serotonin receptor agonist, antagonist or modulator, more particularly agonists, antagonists or modulators for 5HT1A (including VML 670), 5HT2A, 5HT2C, 5HT3 and/or 5HT6 receptors, including those described in WO-09902159, WO-00002550 and/or WO-00028993; and/or

(29) one or more of a modulator of transporters for noradrenaline, dopamine and/or serotonin, such as bupropion, GW-320659; and/or

(30) one or more of a purinergic receptor agonist and/or modulator; and/or

(31) one or more of a neurokinin (NK) receptor antagonist, including those described in WO-09964008; and/or

(32) one or more of an opioid receptor agonist, antagonist or modulator, preferably agonists for the ORL-1 receptor; and/or

(33) one or more of an agonist or modulator for oxytocin/vasopressin receptors, preferably a selective oxytocin agonist or modulator; and/or

(34) one or more modulators of cannabinoid receptors; and/or

(35) one or more of an NEP inhibitor, preferably wherein said NEP is EC 3.4.24.11 and more preferably wherein said NEP inhibitor is a selective inhibitor for EC 3.4.24.11, more preferably a selective NEP inhibitor is a selective inhibitor for EC 3.4.24.11, which has an $IC_{50}$ of less than 100 nM (e.g. ompatrilat, sampatrilat) suitable NEP inhibitor compounds are described in EP-A-1097719; and/or

(36) one or more compounds which inhibit angiotensin-converting enzyme such as enalapril, and one or more combined inhibitors of angiotensin-converting enzyme and neutral endopeptidase such as omapatrilat; and/or

(37) one or more tricyclic antidepressants, e.g. amitriptiline; and/or

(38) one or more non-steroidal anti-inflammatory agents; and/or

(39) one or more angiotensin-converting enzyme (ACE) inhibitors, e.g. quinapril; and/or

(40) one or more anti-depressants (such as clomipramine and SSRIs (such as paroxetine and sertaline).

wherein said combination can be in the form of co-administration, simultaneous administration, concurrent administration, or stepwise administration.

It is to be appreciated that all references herein to treatment include curative, palliative and prophylactic treatment.

The compounds of the invention, their pharmaceutically acceptable salts, and pharmaceutically acceptable solvates of either entity can be administered alone but, in human therapy will generally be administered in admixture with a suitable pharmaceutical excipient diluent or carrier selected with regard to the intended route of administration and standard pharmaceutical practice.

For example, the compounds of the invention, or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, or controlled-release such as sustained-, dual-, or pulsatile delivery applications. The compounds of the invention may also be administered via intracavernosal injection. The compounds of the invention may also be administered via fast dispersing or fast dissolving dosages forms or in the form of a high energy dispersion or as coated particles. Suitable pharmaceutical formulations of the compounds of the invention may be in coated or un-coated form as desired.

Such tablets may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds of the invention can also be administered parenterally, for example, intracavernosally, intravenously, intra-arterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the invention or salts or solvates thereof will usually be from 10 to 500 mg (in single or divided doses).

Thus, for example, tablets or capsules of the compounds of the invention or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including MED and FSD), compounds of the invention may be taken as a single dose on an "as required" basis (i.e. as needed or desired).

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the invention or salts or solvates thereof can be administered in the form of a suppository or pessary, or they may be applied topically in the form of a gel, hydrogel, lotion, solution, cream, ointment or dusting powder. The compounds of the invention or salts or solvates thereof may also be dermally administered. The compounds of the invention or salts or solvates thereof may also be transdermally administered, for example, by the use of a skin patch. They may also be administered by the ocular, pulmonary or rectal routes.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention or salts or solvates thereof can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Generally, in humans, oral administration of the compounds of the invention is the preferred route, being the most convenient and, for example in MED, avoiding the well-known disadvantages associated with intracavernosal (i.e.) administration. A preferred oral dosing regimen in MED for a typical man is from 25 to 250 mg of compound when required. In circumstances where the recipient suffers from a swallowing disorder or from impairment of drug absorption after oral administration, the drug may be administered parenterally, sublingually or buccally.

For veterinary use, a compound of the invention, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

The following formulation examples are illustrative only and are not intended to limit the scope of the invention. "Active ingredient" means a compound according to formula I or a pharmaceutically acceptable salt thereof.

FORMULATION EXAMPLE 1

Tablet

In general a tablet formulation could typically contain between about 0.01 mg and 500 mg of a compound according to the present invention (or a salt thereof) whilst tablet fill weights may range from 50 mg to 1000 mg. An example formulation for a 10 mg tablet is illustrated:

| Ingredient | % w/w |
|---|---|
| Free acid, Free base or Salt of Compound | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

FORMULATION EXAMPLE 2

A tablet is prepared using the following ingredients:

|  | Quantity (mg/tablet) |
|---|---|
| Active ingredient | 250 |
| cellulose, microcrystalline | 400 |
| silicon dioxide, fumed | 10 |
| stearic acid | 5 |
| total | 665 mg | the components are blended and compressed to form tablets each weighing 665 mg. The tablets are manufactured by a standard process, for example, direct compression or a wet or dry granulation process. The tablet cores may be coated with appropriate overcoats.

FORMULATION EXAMPLE 3

An intravenous formulation may be prepared as follows:

| Active ingredient | 100 mg |
|---|---|
| isotonic saline | 1,000 ml |

In summary, the invention provides:
(i) a compound of the formula (I) or a pharmaceutically acceptable salt or solvate thereof;
(ii) a pharmaceutical composition including a compound of the formula (I) or a pharmaceutically acceptable salt or solvate thereof, together with a pharmaceutically acceptable excipient, diluent or carrier;
(iii) a compound of the formula (I) or a pharmaceutically acceptable salt, solvate or composition thereof, for use as a pharmaceutical or as an animal medicament;
(v) the use of a compound of the formula (I) or of a pharmaceutically acceptable salt, solvate or composition thereof, for the manufacture of a medicament for the curative or prophylactic treatment of a medical condition for which inhibition of cGMP PDE5 is desired or required;
(vi) use of a compound of formula (I) for the curative or prophylactic treatment of a medical condition for which inhibition of cGMP PDE5 is desired or required:
(vii) use as in (v) or (vi) where the disease or disorder is preferably selected from the group consisting of male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD);
(viii) a method of treatment of a mammal for which inhibition of cGMP PDE5 is desired or required including treating said mammal with an effective amount of a compound of the formula (I) or with a pharmaceutically acceptable salt, solvate or composition thereof; and
(ix) a method as in (viii) where the disease or disorder is preferably selected from the group consisting of male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD).

General Procedures

The processes described below are illustrative of the general synthetic procedures which may be adopted in order to obtain the compounds of the invention:

1. A compound of formula (I):

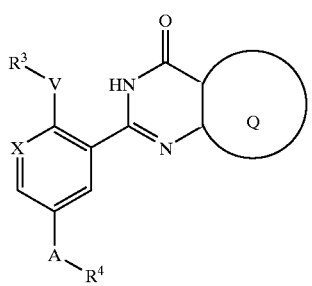

(I)

may be prepared from a compound of general formula (IX):

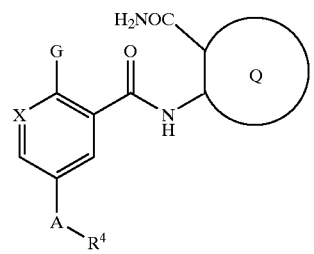

(IX)

wherein G is $VR^3$ (i.e. $OR^3$ or $NR^3R^5$) or X' and wherein A, Q, V, W, X, n, m, and $R^1$ to $R^{17}$ are as defined hereinbefore and X' is a leaving group and wherein general formula (IX) can be represented by formulae (IXA), (IXB) or (IXC) respectively:

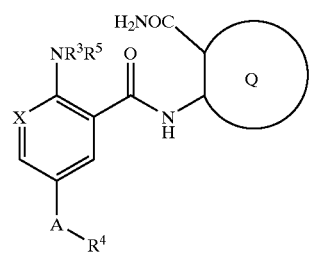

(IXA)

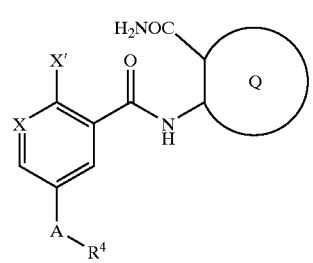

(IXB)

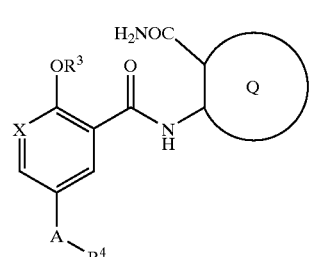

(IXC)

wherein A, Q, V, W, X, n, m, and $R^1$ to $R^{17}$ are as previously defined herein and wherein X' is a leaving group and may be any group which is displaceable by an amino group of the formula —$NR^3R^5$ or by an alkoxy group. Suitable leaving groups, X', for use herein include halogen, alkoxy, amino, tosylate groups and further groups are detailed hereinafter.

1.1 A compound of formula (I) wherein $VR^3$=$NR^5R^6$ may be prepared by cyclisation of a compound of general formula (IXA):

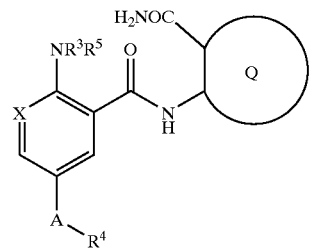

(IXA)

wherein A, Q, V, W, X, n, m, and $R^1$ to $R^{17}$ are as previously defined. Preferably, the cyclisation is base-mediated, using an alkali metal salt of a sterically hindered alcohol or amine. For example, the required cyclisation may be effected using about a 1- to 5-, preferably a 1.2- to 3.5-fold excess of potassium t-butoxide, potassium bis(trimethylsilyl)amide or cesium carbonate, optionally in the presence of molecular sieves, in a suitable solvent, such as for example an inert solvent e.g. DMF or $NHR^3R^5$ or mixtures thereof, at the reflux temperature of the reaction mixture optionally in the presence of about a 1 molar equivalent of ethyl acetate or ethyl pivalate, or, the reaction can optionally be carried out in a sealed vessel at about 100–130° C. optionally in the presence of about a 1 molar equivalent of ethyl acetate or ethyl pivalate.

1.2 A general route for the synthesis of compounds (I) via compounds (IXB) is illustrated in Scheme 1 wherein said intermediate compounds (IXB) have the general formula:

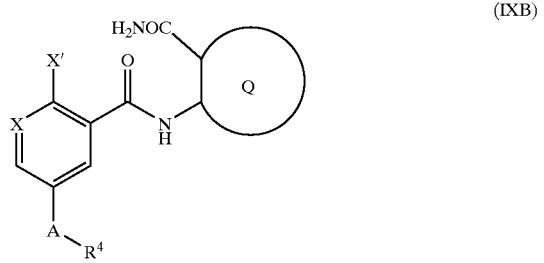
(IXB)

wherein A, Q, V, W, X, n, m, and $R^1$ to $R^{17}$ are as previously defined and wherein X' is a leaving group as defined hereinbefore, by reaction in the presence of $^-OR^3$ and a hydroxide trapping agent. The conversion (IXB) to (I) can be undertaken in either a stepwise process or a one-pot process. A number of stepwise permutations are feasible, some of which are subsets of others. These include i) cyclisation (IXB to XXX) followed by displacement (XXX to I);
ii) cyclisation (IXCa to XXX) followed by displacement (XXX to I);
iii) displacement (IXB to IXC) followed by cyclisation (IXC to I); and
iv) displacement (IXCa to IXC) followed by cyclisation (IXC to I) wherein compounds (XXX) and (IXCa) have the general formulae:

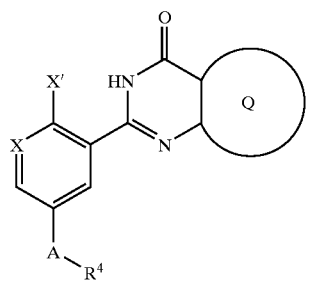
(XXX)

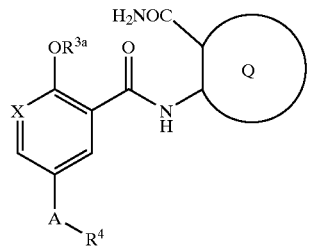
(IXCa)

wherein A, Q, V, W, X, n, m, and $R^1$ to $R^{17}$ are as previously defined and $OR^{3a}$ is an alkoxy group which is different from and displaceable by the desired $OR^3$ group on the final compounds of general formula (I) and wherein $R^{3a}$ is selected from $C_1$ to $C_6$ alkyl optionally substituted with one or two substituents selected from $C_3$ to $C_5$ cycloalkyl, hydroxy, $C_1$ to $C_4$ alkoxy, benzyloxy, $NR^5R^6$, phenyl, Het wherein the $C_1$ to $C_6$ alkyl and $C_1$ to $C_4$ alkoxy groups may optionally be terminated by a haloalkyl group such as $CF_3$ and wherein the $C_3$–$C_5$ cycloalkyl group may optionally be substituted by $C_1$–$C_4$ alkyl, hydroxy or halo; $C_3$ to $C_6$ cycloalkyl; Het. Preferably $R^{3a}$ is $C_1$ to $C_6$ alkyl.

To effect initial displacement without significant simultaneous cyclisation it is preferred that the displacement with $^-OR^3$ (in (iii) or (iv)) is carried out in the range of from about 80° C. to about 90° C. to provide a compound of the general formula (IXC). Subsequent cyclisation to a compound of general formula (I) is generally carried out at a temperature greater than about 115° C.

To effect initial cyclisation without significant simultaneous displacement it is preferred that, for (IXCa) to (XXX) (in (ii)), the reaction is conducted at a temperature greater than about 110° C. with $^-OR^{3a}$ in $R^{3a}OH$. Subsequent displacement to a compound of general formula (I) is generally carried out with $^-OR^3$ in $R^3OH$ in the range of from about 80° C. to about 90° C.

For conversion of (IXB) to (I) (ie. (i) above), it may be preferred to obtain compounds of general formula (I) directly from compounds of general formula (IXB) since both the cyclisation and displacement components of this reaction can be carried out in a "one-pot" reaction. Such a "one-pot" process can be run at lower pressures (ie. nearer ambient pressure) than say a stepwise cyclisation and displacement process (ie. (ii) above) if the boiling point of $R^3OH$ is higher than that of $R^{3a}OH$ and where the ambient boiling point of $R^{3a}OH$ is less than about 115° C. (ie. too low to effect cyclisation at ambient pressure). It should be noted that it may still be necessary to operate such processes at higher temperatures than the boiling point of $HOR^3$, i.e. at higher pressure.

In the case of compounds of general formula (IXC) as detailed hereinafter wherein X is $OR^3$, compounds of general formula (I) can be obtained by direct cyclisation by reacting in the presence of an auxiliary base, a hydroxide trapping agent and an appropriate solvent $R^3OH$ or an inert solvent or a combination thereof.

The temperature of the reaction of compounds of the general formula (IXB) to compounds of the general formula (I) (such as the corresponding formation of compounds (IA) and (IB)) is preferably at least about 80° C., more preferably about 80 to about 130° C., more preferably still about 100 to about 130° C. and most preferably about 115 to about 125° C. These temperatures are also applicable for the conversion of compounds (XXX) to (I), although the temperature in this case could also probably be lower (e.g. about 60° C.) since there is no cyclisation taking place.

Intermediates of the general formula (IXC) form further aspects of the invention.

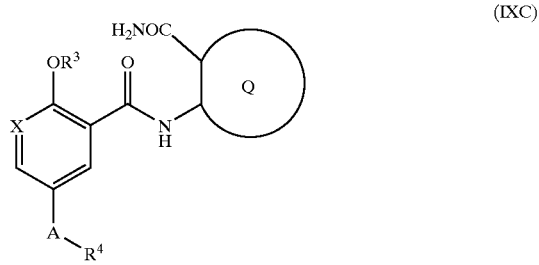

(IXC)

A particular advantage of the use of the hydroxide trapping agent is that a higher yield of final product (compounds of general formula (I)) can be obtained than for the same reaction where the trapping agent is not present.

Preferably the hydroxide trapping agent is an ester. More preferably said hydroxide trapping agent is an ester of the formula:

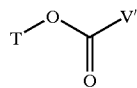

wherein OT is $OR^3$ or the residue of a bulky alcohol or a non-nucleophilic alcohol or TOH is an alcohol which can be azeotropically removed during the reaction; and C(O)V' is the residue of a carboxylic acid. For example, where $OR^3$ is OEt in compound (IXC) the hydroxide trapping agent (TOC(O)V') could be e.g. ethyl acetate or ethyl pivalate. Preferably V' is a $C_1$ to $C_4$ alkyl group.

Preferably X' is selected from the group consisting of —$OR^3$, halo, optionally substituted arylsulphonyloxy, preferably phenylsulphonyloxy, more preferably a para-substituted aryl (phenyl) such as by a $C_1$–$C_4$ alkyl group e.g. p-toluenesulphonyloxy; $C_1$–$C_4$ alkylsulphonyloxy e.g. methanesulphonyloxy; nitro or halo substituted benzenesulphonyloxy preferably para-substituted e.g. p-bromobenzenesulfonyloxy or p-nitrobenzenesulphonyloxy; $C_1$–$C_4$ perfluoroalkylsulphonyloxy e.g. trifluoromethylsulphonyloxy; optionally substituted aroyloxy such as benzoyloxy; $C_1$–$C_4$ perfluoroalkanoyloxy such as trifluoroacetyloxy; $C_1$–$C_4$ alkanoyloxy such as acetyloxy; diazonium; quatenaryammonium $C_1$–$C_4$ alkylsulphonyloxy; halosulphonyloxy e.g. fluorosulphonyloxy and other fluorinated leaving groups; and diarylsulphonylamino e.g. ditosyl ($NTs_2$).

More preferably, X' is a $C_1$–$C_6$ primary or secondary alkoxy and is especially a $C_1$–$C_4$ alkoxy group such as ethoxy or methoxy.

$^-OR^3$ can act both as a nucleophile (to displace the leaving group by nucleophilic substitution) and as a base (to bring about the cyclisation).

$^-OR^3$ can be generated in solution from, for example, a salt $Z'OR^3$ (wherein Z' is a cation) such as a metal salt. More particularly an alkali (such as sodium or potassium) or alkaline earth metal salt of —$OR^3$ in a suitable solvent would give rise to —$OR^3$ in solution. In another embodiment, —$OR^3$ is formed in situ from $R^3OH$ plus an auxiliary base (i.e. a base other than —$OR^3$). However, in another system, $Z'OR^3$ could be used in the reaction system with an auxiliary base.

As will be appreciated the solvent in which the reaction takes place can be $R^3OH$ or an inert solvent (or a mixture of both). By inert solvent we mean a solvent which will not form a nucleophile under the reaction conditions or if a nucleophile is formed it is sufficiently hindered or unreactive such that it does not substantially compete in the displacement reaction. When $R^3OH$ is used as a source of $^-OR^3$, then a separate solvent is not essentially required but an (auxiliary) inert solvent (i.e. a solvent other than $R^3OH$) may be used as a co-solvent in the reaction.

Suitable solvents are as follows: $R^3OH$, a secondary or tertiary $C_4$–$C_{12}$ alkanol, a $C_3$–$C_{12}$ cycloalkanol, a tertiary $C_4$–$C_{12}$ cycloalkanol, a secondary or tertiary ($C_3$–$C_7$ cycloalkyl)$C_2$–$C_6$ alkanol, a $C_3$–$C_9$ alkanone, 1,2-dimethoxyethane, 1,2-diethoxyethane, diglyme, tetrahydrofuran, 1,4-dioxan, toluene, xylene, chlorobenzene, 1,2-dichlorobenzene, acetonitrile, dimethyl sulphoxide, sulpholane, N,N-dimethylformamide, N-methylpyrrolidin-2-one, pyridine, and mixtures thereof.

More preferably, the solvent is $R^3OH$, a tertiary $C_4$–$C_{12}$ alkanol, a tertiary $C_4$–$C_{12}$ cycloalkanol, a tertiary ($C_3$–$C_7$ cycloalkyl)$C_2$–$C_6$ alkanol, a $C_3$–$C_9$ alkanone, 1,2-dimethoxyethane, 1,2-diethoxyethane, diglyme, tetrahydrofuran, 1,4-dioxan, toluene, xylene, chlorobenzene, 1,2-dichlorobenzene, acetonitrile, dimethyl sulphoxide, sulpholane, N,N-dimethylformamide, N-methylpyrrolidin-2-one, pyridine, and mixtures thereof.

Most preferably the solvent is $R^3OH$, which means that $^-OR^3$ is formed in situ, such as in the presence of an auxiliary base.

A wide range of auxiliary bases can be used in the process of the invention. Typically the bases would not substantially compete with —$OR^3$ in the nucleophilic substitution of X' (i.e. they would be non nucleophilic) such as by suitably being sterically hindered.

Preferably the auxiliary base is selected from the group consisting of a sterically hindered base, a metal hydride, metal oxide, metal carbonate and metal bicarbonate.

More preferably the auxiliary bases in accordance with the invention are selected from the group consisting of metal salts of a sterically hindered alcohol or amine such as a secondary or tertiary $C_4$–$C_{12}$ alkanol, a $C_3$–$C_{12}$ cycloalkanol and a secondary or tertiary ($C_3$–$C_8$ cycloalkyl)$C_1$–$C_6$ alkanol, a N-(secondary or tertiary $C_3$–$C_6$ alkyl)-N-(primary, secondary or tertiary $C_3$–$C_6$ alkyl)amine, a N-($C_3$–$C_8$ cycloalkyl)-N-(primary, secondary or tertiary $C_3$–$C_6$ alkyl)amine, a di($C_3$–$C_8$ cycloalkyl)amine or hexamethyidisilazane; 1,5-diazabicyclo[4,3,0]non-5-ene and 1,8-diazabicyclo[5,4,0]undec-7-ene; a metal hydride, oxide, carbonate, and bicarbonate.

More preferably still, the auxiliary base is the metal salt of a tertiary $C_4$–$C_6$ alcohol such as the alkali or alkaline earth metal salts (e.g. Na/K/Cs) of t-butanol or t-amyl alcohol, or the base is KHMDS or alkaline earth carbonates (eg. Na/K/Cs).

To maximise yields, it is further preferred that when X' is any group hereinbefore defined except —$OR^3$, then at least about 1 molecular equivalent of auxiliary base and —$OR^3$ are used. If —$OR^3$ also functions as a base (i.e. there is no auxiliary base present) then preferably at least about 2 equivalents of $^-OR^3$ are present. Suitably, at least about 1 equivalent of trapping agent (preferably at least about 2 equivalents) is present. In the case where X'=$OR^3$ (i.e. starting from (IXC) rather than (IXB) then, in theory, at least 1 equivalent of base is required, wherein said base may be —$OR^3$ or auxiliary base.

The temperature of the reaction of compounds of the general formula (IXC) to compounds of the general formula (I) (such as the corresponding formation of compounds (IA)

and (IB)) is preferably at least about 80° C., more preferably about 80 to about 130° C., more preferably still about 100 to about 130° C. and most preferably about 115 to about 125° C.

The reaction temperature attainable to effect the conversion of compounds of the general formulae (IXB), (IXC) or (XXX) to compounds of the general formula (I) depends on the solvent, the nature of $^-OR^3$ and X'. When X' is $OR^{3a}$ (wherein $OR^{3a}$ and $OR^3$ are not the same), i.e. a compound of the formula (IXC$^a$) and $R^3OH$ is the solvent, preferably X'H (such as $C_1$–$C_6$ alcohol) is removed azeotropically (of course the reaction vessel must be configured to distill over the azeotrope mixture) with $R^3OH$ by running the reaction at the azeotrope temperature of X'H and $R^3OH$. In this way the yield and quality of the final product can be further improved. For example, (where X' is an alkoxy, preferably ethanol) the conversion of compound (XXX), (IXB) or (IXC) to (I) is preferably carried out at the azeotrope temperature of the alcohol (i.e. X'H (preferably ethanol)) with $R^3OH$. When X'=$OR^3$ and the solvent is $R^3OH$ there is no requirement to azeotrope out $R^3OH$.

1.3 For compounds of the general formula (IXB) wherein X' is $OR^3$ and an alcohol is selected as solvent, a compound of formula (I) may be prepared by cyclisation of a compound of general formula (IXC):

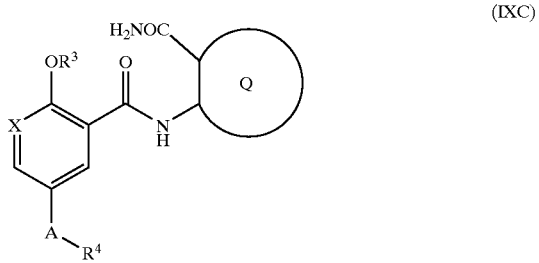

(IXC)

wherein A, Q, V, W, X, n, m, and $R^1$ to $R^{17}$ are as previously defined. In said reaction the appropriate alcohol of formula $R^3OH$ should be employed as the solvent in order to obviate potential problems associated with alkoxide exchange at the 2-position of the pyridine ring or an inert solvent or a mixture of the two. The appropriate alcohol as defined herein means that the solvent alcohol should be of the same alkyl chain length as the alkoxy (—$OR^3$) substituent, for example, where —OR$^3$ is ethoxy, ethanol is the appropriate alcohol. Preferably, said cyclisation is base-mediated, using an alkali metal salt of a sterically hindered alcohol or amine or carbonate. For example, the required cyclisation may be effected using about a 1- to 8, preferably about a 1- to 5-, more preferably a 1.2- to 3.5-fold excess of potassium t-butoxide or potassium bis(trimethylsilyl)amide, or caesium carbonate, optionally under suitable drying conditions i.e. in the presence of molecular sieves or under azeotroping conditions, in a suitable solvent as described above at the reflux temperature of the reaction mixture optionally in the presence of about 1 to 2 molar equivalents of a hydroxide trapping agent such as ethyl acetate or ethyl pivalate, or, the reaction can optionally be carried out in a sealed vessel at about 100–130° C. optionally in the presence of about 1 to 2 molar equivalents of a hydroxide trapping agent such as ethyl acetate or ethyl pivalate.

Alternative reaction conditions for the cyclisation reactions of compounds of (IXC) wherein X' is $OR^3$ are to conduct the reaction with about 1.2 to 4.5 molecular equivalents of sterically hindered base such as potassium t-butoxide or KHMDS, or caesium carbonate, optionally in a sealed vessel at from about 100° C. to about 150° C. with, rather than an alcohol of formula $R^3OH$ as solvent, a sterically hindered alcohol, e.g. 3-methylpentan-3-ol, as solvent optionally in the presence of about 1 or 2 molar equivalents of ethyl acetate or ethyl pivalate.

A compound of formula (IXA) or a compound of formula (IXB) wherein X' is $OR^3$ (i.e. a compound of general formula (IXC)) may be prepared by a coupling reaction between a compound of formula (VII):

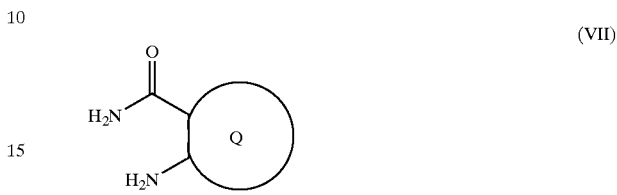

(VII)

wherein A etc. are as previously defined, with a compound of formula (XA), (XB) or (XC) respectively:

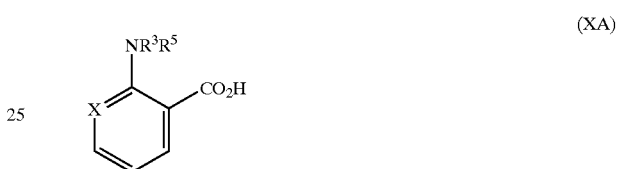

(XA)

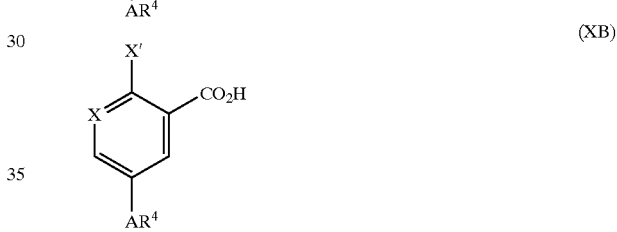

(XB)

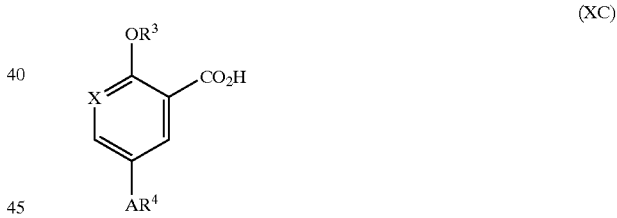

(XC)

wherein A, $R^3$, $R^4$, $R^5$, X and X' are as previously defined. Where either $R^3$ and/or $R^5$ in the —$NR^3R^5$ group of formula (XA) are H, then a suitable N-protecting group strategy may be advantageously employed. Any known suitable protecting group strategy may be used.

The coupling reaction may be carried out using conventional amide bond-forming techniques, e.g. via the acyl chloride derivative of (XA), (XB) or (XC) in the presence of up to about a five-fold excess of a tertiary amine such as triethylamine or pyridine to act as scavenger for the acid by-product (HY), optionally in the presence of a catalyst such as 4-dimethylaminopyridine, in a suitable solvent such as dichloromethane, at from about 0° C. to about room temperature. For convenience pyridine may also be used as the solvent.

In particular, any one of a host of amino acid coupling variations may be used. For example, the acid of formula (XA), (XB) or (XC) or a suitable salt (e.g. sodium salt) thereof may be activated using a carbodiimide such as 1,3-dicyclohexylcarbodiimide or 1-ethyl-3-(3-dimethylaminoprop-1-yl)carbodiimide optionally in the presence of 1-hydroxybenzotriazole hydrate and/or a catalyst such as 4-dimethylaminopyridine, or by using a halotrisaminophosphonium salt such as bromotris(pyrrolidino) phosphonium hexafluorophosphate or by using a suitable pyridinium salt such as 2-chloro-1-methylpyridinium iodide. Either type of coupling is conducted in a suitable solvent such as dichloromethane, tetrahydrofuran or N,N-dimethylformamide, optionally in the presence of a tertiary amine such as triethylamine or N-ethyldiisopropylamine (for example when either the compound of formula (VII), or the activating reagent, is presented in the form of an acid addition salt), at from about 0° C. to about room temperature. Preferably, from 1 to 2 molecular equivalents of the activating reagent and from 1 to 3 molecular equivalents of any tertiary amine present are employed.

In a further variation, the carboxylic acid function of (XA), (XB) or (XC) may first of all be activated using up to about a 5% excess of a reagent such as N,N-carbonyldiimidazole in a suitable solvent, e.g. ethyl acetate or butan-2-one, at from about room temperature to about 80° C., followed by reaction of the intermediate imidazolide with (VII) at from about 20° C. to about 90° C.

The compounds having the general formulae (VII)

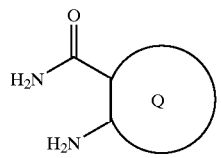

(VII)

may be prepared according to the following general procedures. For example, where Q is a group of the formula:

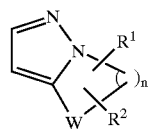

the synthesis can be achieved by the following routes:

Route A in the following scheme

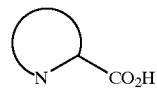

represents

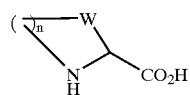

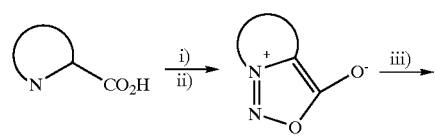

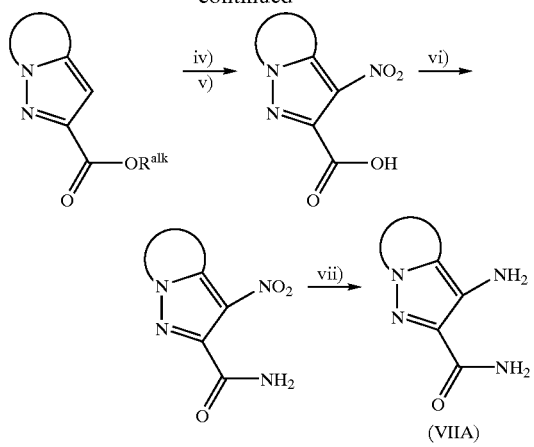

(VIIA)

which involves the following general steps i) a N-nitrosation reaction using a suitable reagent (eg nitrous acid, prepared in-situ from HCl/NaNO$_2$, NOCl, BrCH$_2$NO$_2$) in a suitable solvent (eg water), for up to 24 hrs. Preferably, the reaction is carried out using HCl and 1.1 eq of NaNO$_2$ in H$_2$O at room temperature for 2 hrs.

ii) cyclodehydration using a suitable acid activating agent (eg trifluoroacetic anhydride (TFFA)), in a suitable solvent (ether, THF) at room temperature for 1 to 24 hours. Preferably the reaction is carried out using 1.1 eq TFAA in diethylether at room temperature for 18 hrs.

iii) 2+3 cycloaddition reaction in which cycloaddition with a suitable alkene (—CH≡CCO$_2$R$_{alk}$) where R$_{alk}$ is preferably a C$_1$–C$_4$ alkyl, is performed at elevated temperature with a suitable high boiling solvent, eg xylene, or toluene for 2 to 8 hrs. Preferably the reaction is carried out using (—CH≡CCO$_2$R$_{alk}$) in xylene at reflux for 2 to 8 hrs.

iv) ester hydrolysis in the presence of acid (eg HCl) or base (NaOH, LiOH) in a suitable solvent system (dioxan, water) at room temperature for up to 48 hrs. Preferably the reaction is carried out using NaOH (aq) in dioxan at room temperature for 18 hrs.

v) nitration under standard nitrating conditions, such as fuming HNO$_3$ with H$_2$SO$_4$, NO$_2$$^+$BF$_4$$^-$, or EtONO$_2$, optionally in a suitable solvent, at between room temperature and an elevated temperature. Preferably the reaction is carried out in a mixture of fuming HNO$_3$ and H$_2$SO$_4$ at 40 to 60° C. for 4 hrs.

vi) amide formation is effected as described previously for the formation of (IXA) by reaction of (VII) with (XA), (XB) or (XC).

vii) hydrogenation is carried out using standard catalytic hydrogenation conditions. For example, using a suitable catalyst (eg Raney® Nickel, 10% palladium on charcoal) in an alcoholic suitable solvent (ethanol, methanol), at a hydrogen pressure of about 60 psi at elevated temperature for up to 24 hrs. Alternatively, the transformation may be performed under transition metal catalysed reduction, using Sn in the presence of HCl, in an alcoholic solvent (EtOH), at between room temperature and reflux temp. Preferably, the reaction is carried out with 10% Pd/C, in EtOH or MeOH at a pressure of 60 psi and at a temperature of room temperature to 60° C. for 5 to 18 hrs.

The compound of formula (VII) can also be synthesised by the following general route:

Route B

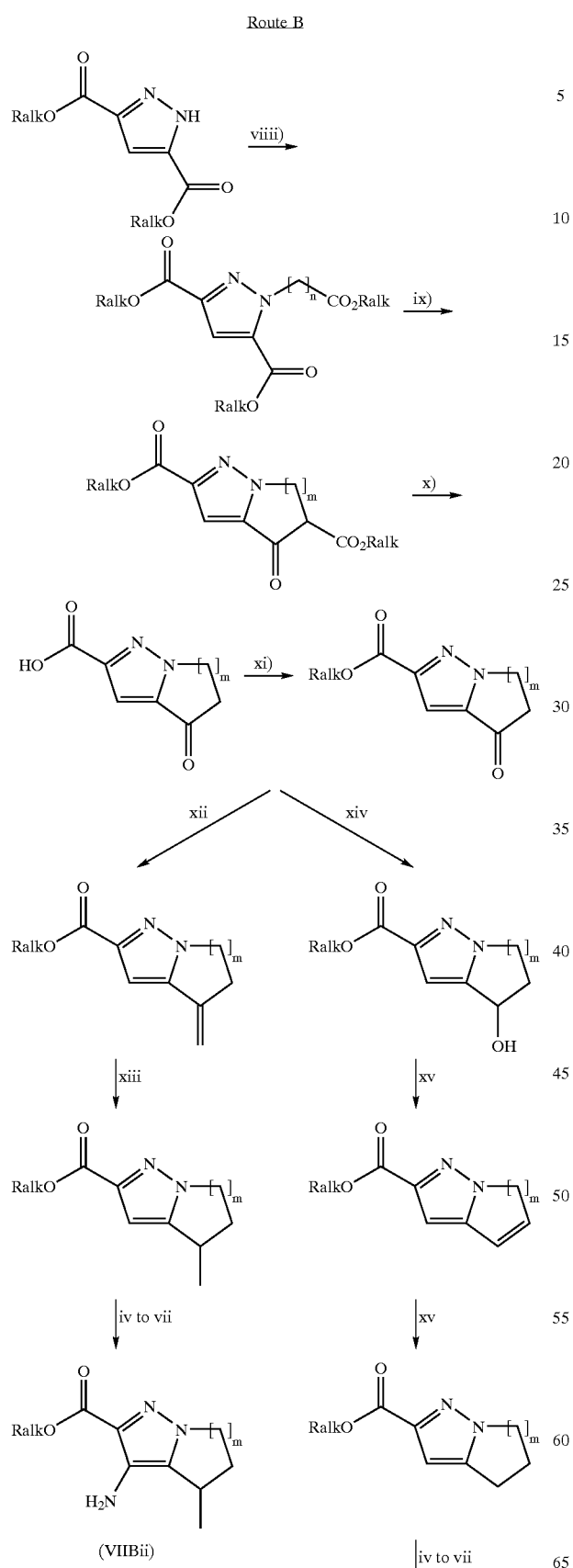

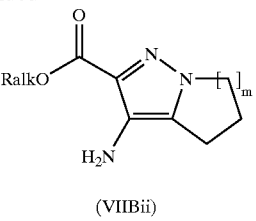

(VIIBii)

where n in the above scheme=2 to 5 and m in the above scheme=(n−1) Ralk is preferably Me or Et.

which involves the following general steps viii) alkylation using a suitable alkylating agent, (L[CH$_2$]$_n$CO$_2$Ralk), where L is a leaving group, typically halo, mesylate or tosylate and Ralk is C$_1$–C$_4$ alkyl, in the presence of a suitable base (eg alkali metal salt, such as K$_2$CO$_3$, Na$_2$CO$_3$, NaH) in a suitable solvent, such as N,N-dimethylformamide or MeCN, at between room temperature and reflux, for between 2 and 24 hrs. Preferably, the alkylating agent is Br(CH$_2$)$_n$CO$_2$Ralk) (1 eq) and the base is K$_2$CO$_3$ (1 eq) and the reaction is carried out in MeCN at reflux for 2 hrs.

ix) Dieckmann cyclisation which is catalysed by a slight excess of suitable base (NaNH$_2$, NaH, KOtBu) in a suitable solvent (toluene, tetrahydrofuran) at elevated temperature for up to 24 hrs. Preferably, the base is KO$^t$Bu (1.1eq) and the solvent is toluene with the reaction being carried out at reflux for 1 to 12 hrs.

x) decarboxylation/hydrolysis is performed under acidic (eg HCl) or basic conditions (eg NaOH), in a suitable alcoholic or aqueous solvent system, at elevated temp for up to 24 hrs. Preferably, the reaction is carried out in HCl/H$_2$O at reflux for 2 to 5 hrs.

xi) esterification is performed under standard conditions, using either acid (eg HCl, H$_2$SO$_4$) or base catalysis (eg, NaOH), using a suitable alcohol (R$_{alk}$OH) where Ralk is typically C$_1$–C$_4$ alkyl, in a suitable solvent (eg RalkOH) at elevated temperature. Preferably, the reaction is carried out in H$_2$SO$_4$ and the reaction mixture containing RalkOH (eg EtOH), is refluxed for 2 to 4 hrs.

xii) Wittig reaction which is performed under standard conditions as described in Org. Synth. Coll. 5, 751 1973, using a suitable phosphonium salt in the presence of a suitable base (eg alkali metal salt) in a suitable solvent (eg toluene) at elevated temperature. Preferably, the reaction is carried out with CH$_3$PPh$_3^+$ Br$^-$ (1.16 eq) and KO$^t$Bu (1.1 eq) in toluene at room temperature for 18 hrs.

xiii) hydrogenation is carried out using the conditions described for vii) Preferably, the reaction is performed with 10% Pd/C in EtOH or MeOH at a pressure of 60 psi and at a temperature of room temperature to 50° C. for 2.5 hrs.

xiv) reduction is effected using a suitable selective metal hydride reducing agent (eg NaBH$_4$, DIBALH), in a suitable solvent (eg EtOH) at between 0° and room temperature for between 1 and 24 hrs. Preferably, the reaction is performed with NaBH$_4$ (1.1 eq) in EtOH at a temperature of from 0° C. to room temperature for 2 hrs.

xv) dehydration of the alcohol is carried out under acidic or neutral conditions, using a suitable reagent (eg H$_2$SO$_4$, pTsOH), as described in Larock, Comprehensive Organic Transformations, VCH; New York, 1989, pg 151–152. Preferably, the reaction is carried out using a catalytic amount of pTSOH in toluene at reflux for 4 hrs.

xvi) hydrogenation is performed under the same conditions as described in vii) above. Preferably, the reaction is carried out with 10% Pd/C in EtOH at a pressure of 60 psi and at a temperature of room temperature for 17 hrs.

Alternatively, the following general procedure may be used:

Route C

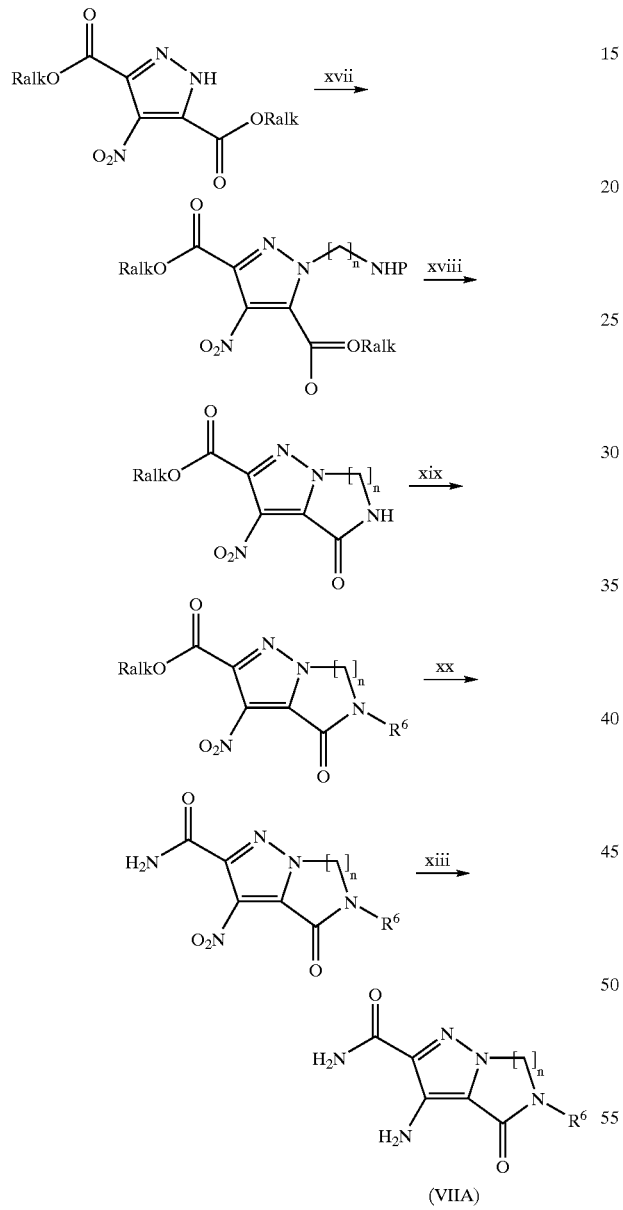

(VIIA)

where n in the above scheme=1–3.

xvii) alkylation is carried out using the same conditons described for viii) above. Preferably, the alkylating agent (eg mesylate), (1.1 eq) is reacted with the pyrazole in the prescence of $K_2CO_3$ in a mixture of MeCN:DMF (1:1) at a temperature of 50° C. for 3 days.

xviii) deprotection/cyclisation; the deprotection is performed under standard conditions, as described in "Protective Groups in Organic Synthesis", by Greene and Wutz, Wiley-Interscience 1991. Cyclisation is catalysed by an excess of 3° amine base (eg $Et_3N$, Hunig's base), in a suitable solvent (eg MeOH) at room temperature. Preferably, protecting group P is Boc and the reaction is carried out in TFA/DCM at room temperature for 2 hrs. Cyclisation is then effected in MeOH using $Et_3N$ (4 eq) at room temperature for 30 mins.

xix) alkylation is carried out under the same conditions as described for xvii) and viii) above. Preferably, the alkylating agent (eg halide) (1.2 eq) and the base (eg NaH, 1.1 eq) are reacted in DMF at room temperature for 1 hr.

xx) amide formation is achieved by reaction of the ester with $NH_3$ at elevated temperature and pressure in a suitable solvent (DMSO, MeOH, EtOH) for about 8 to 72 hrs. Preferably, the reaction is performed with $NH_3$/EtOH at 100° C. for 16 hrs in a sealed vessel.

When A is $SO_2$, compounds having the general formulae (XA), (XB) or (XC)

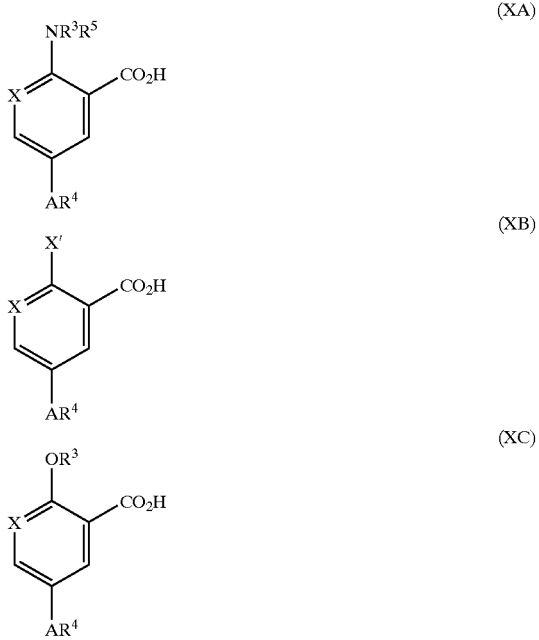

may be prepared from the carboxylic acid compounds of the general formulae (VIIIA), (VIIIB) or (VIIIC) respectively:

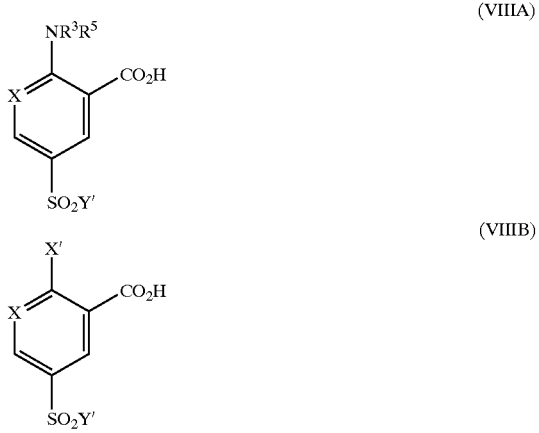

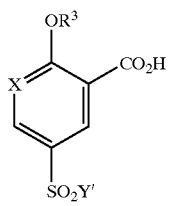
(VIIIC)

wherein $R^3$ and $R^5$ are as defined previously by reaction with a 4-substituted-piperizinyl compound, such as for example 4-methylpiperazine or 4-ethylpiperazine. Such reaction can be conducted at from about 0° C. to about room temperature, preferably in the presence of an appropriate solvent such as a $C_1$ to $C_3$ alkanol or dichloromethane optionally in the presence of a suitable base such as triethylamine to scavenge the acid by-product (HY') where Y' is halo, preferably chloro. Where either $R^3$ or $R^5$ is H a suitable amino protecting group strategy may be employed as detailed hereinbefore.

Compounds of the general formulae (VIIIA), (VIIIB) or (VIIIC) may be prepared from compounds of the general formulae (XIA), (XIB) or (XIC) respectively:

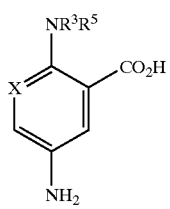
(XIA)

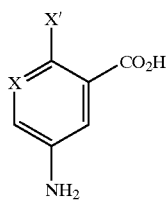
(XIB)

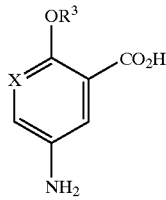
(XIC)

wherein $R^3$, $R^5$, X and X' are as defined previously by the application of known methods for converting amino to an $SO_2Y'$ group, wherein Y' is halo, preferably chloro. For example, when Y' is chloro, by the action of about a two-fold excess of sodium nitrite in a mixture of concentrated hydrochloric acid and glacial acetic acid at from about −25° C. to about 0° C., followed by treatment with excess liquid sulphur dioxide and a solution of about a three-fold excess of cupric chloride in aqueous acetic acid at from about −15° C. to about room temperature. When $VR^3$ contains a primary or secondary amino group, protection of the said amino group with an acid stable group such as acetyl or benzyl will generally be advantageous.

Compounds of the general formula (XIA), (XIB) and (XIC) may be prepared by reduction of compounds of the general formulae (XIIA), (XIIB) and (XIIC) respectively:

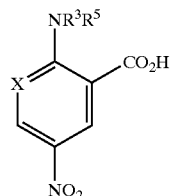
(XIIA)

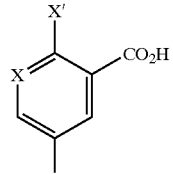
(XIIB)

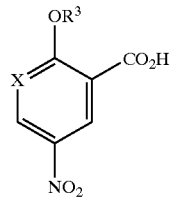
(XIIC)

wherein $R^3$, $R^5$, X and X' are as previously defined. Such conversion of compounds of the general formulae (XIIA), (XIIB) and (XIIC) to compounds of the general formulae (XIA), (XIB) and (XIC) can be achieved by conventional catalytic or catalytic transfer hydrogenation procedures. Typically, the hydrogenation is achieved using a Raney (RTM) nickel catalyst or a palladium catalyst such as 10% Pd on charcoal, in a suitable solvent such as ethanol at a hydrogen pressure of from about 345 kPa (50 psi) to about 414 kPa (60 psi) at from about room temperature to about 60° C., preferably from about 40° C. to about 50° C.

Intermediates of the general formula (IXC) as described in 1.2 and 1.3 hereinbefore can be prepared via a coupling reaction between a compound of the general formula (XB) and a compound of the general formula (VII) wherein said coupling may be achieved by any of the methods described hereinbefore.

Compounds of general formula (XB) may be prepared according to or by analogy with the route outlined in Scheme 1 where A is $SO_2$.

Scheme 1

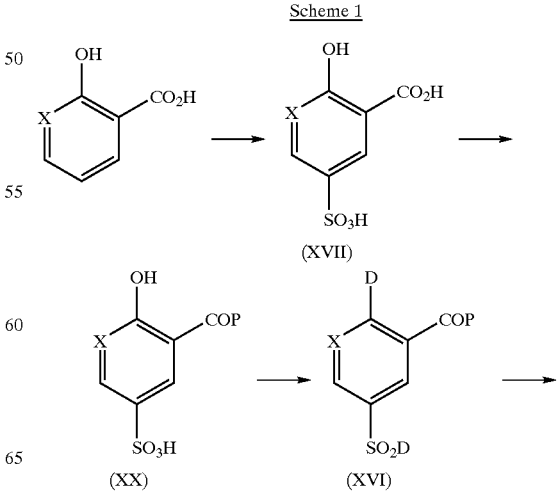

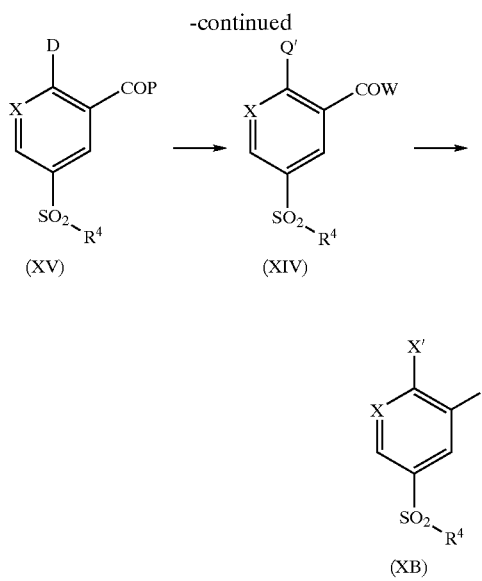

With reference to Scheme 1, the intermediate of formula (XB) is formed from a compound of formula (XIV), the exact process being dependent on leaving group X'.

For compounds of formula (XB) wherein X'=arylsulfonyloxy, $C_1$–$C_4$ alkylsulfonyloxy, $C_1$–$C_4$ perfluoroalkylsulfonyloxy, aryloxy, $C_1$–$C_4$ perfluoroalkanoyloxy, $C_1$–$C_4$ alkanoyloxy, quarternaryammonium $C_1$–$C_4$ alkylsulfonyloxy or halosulfonyloxy, compound (XB) can be formed from compounds (XIV) (wherein Q'=OH and W'=OH) and an appropriate derivatising agent, more particularly an appropriate sulphonylating agent such as arylsulfonylhalide, $C_1$–$C_4$ alkylsulfonylhalide, $C_1$–$C_4$ perfluoroalkylsulfonylhalide, arylhalide, $C_1$–$C_4$ perfluoroalkanoylhalide, $C_1$–$C_4$ alkanoylhalide, quarternary ammonium $C_1$–$C_4$ alkylsulfonylhalide or halosulfonylhalide, or an appropriate arylating agent such as arylhalide, or an appropriate acylating agent such as $C_1$–$C_4$ perfluoroalkanoylhalide, or $C_1$–$C_4$ alkanoylhalide), respectively (preferably the halide substituent of the above is chloride), in an appropriate solvent. Compounds of formula (XIV) (wherein Q'=OH and W'=OH) can be formed from compounds (XV) (wherein P is hydrolisable group) via use of a hydrolising agent, preferably a hydroxide base (ideally 2 molar equivalents), more preferably a metal hydroxide such as sodium hydroxide, in an appropriate solvent, such as water. The metal of the hydroxide base can be as defined hereinbefore for Z' (in Z'OR). This will also apply for other reactions of scheme 1 and 2 hereafter where hydroxide base/hydrolising agent is used. Where P is group which is not hydrolisable by hydroxide then a suitable de-protection strategy should be employed according to standard literature practise.

Compounds of formula (XB) where X'=chloro, can be formed from (XIV) wherein Q'=Cl and W'=P (such as OEt) (i.e. formula XV) and a hydroxide base (ideally 1 molar equivalent), such as sodium hydroxide preferably in an appropriate solvent, such as water and a deprotecting agent.

Preferably the deprotecting agent as used herein in accordance with the invention is a hydrolysing agent, more preferably a hydroxide nucleophile, advantageoulsly a hydroxide base (ideally 1 molar equivalent), such as sodium hydroxide preferably in an appropriate solvent, such as water.

Compounds of formula (XB) wherein X'=diazonium, can be formed from (XIV) (wherein Q'=NH$_2$, W'=OH) and nitrous acid. Compounds of formula (XIV) (wherein Q'=NH$_2$, W'=OH) can be formed from compounds of formula (XIV) (wherein Q'=NH$_2$, W'=P, e.g. OEt) and a deprotecting agent such as a hydroxide base e.g. sodium hydroxide, in an appropriate solvent, such as water. Intermediate (XIV) (Q'=NH$_2$, W'=P, e.g. OEt) is formed from (XV) and an ammoniating agent, such as ammonia, in an appropriate solvent, such as water.

Compounds of formula (XB) wherein X'=diarylsulfonylamino, can be formed from (XIV) (wherein Q'=NH$_2$, W'=OH) and an appropriate derivatising agent, preferably an appropriate sulphonylating agent such as arylsulphonylhalide, preferably arysulfonylchloride (ideally at least 2 molar equivalents) and preferably in the presence of a base (ideally 2 molar equivalents thereof, such as triethylamine in an appropriate solvent.

Compounds of formula (XB) wherein X'=$C_1$–$C_6$ (preferably $C_1$–$C_4$) preferably primary or secondary alkoxy, can be formed from (XIV) (wherein Q'=$C_1$–$C_6$ (preferably $C_1$–$C_4$) primary or secondary alkoxy and W'=P, such as OEt) and a deprotecting agent (for P=OEt), preferably a hydroxide base, such as sodium hydroxide, in an appropriate solvent, such as water. Compounds of formula (XIV) (wherein Q'=$C_1$–$C_6$ (preferably $C_1$–$C_4$) primary or secondary alkoxy, W'=P e.g. OEt) can be formed from (XV) and an appropriate alkoxide, OR$^-$ wherein R is $C_1$–$C_6$ alkyl more preferably $C_1$–$C_4$ primary or secondary alkyl, such as sodium ethoxide in an appropriate solvent such as toluene. Most preferably P=X' (wherein X' is an alkoxy) since this avoids trans-esterification issues.

The compounds of formula (XV) can be formed from compounds of formula (XVI) by reaction with a mono-N-substituted piperazine, optionally in the presence of a supplementary base (which does not react irreversibly with the sulphonyl chloride moiety) such as triethylamine preferably in an appropriate solvent, such as toluene. "D" in compounds (XV) and (XVI) is Cl or Br. The monosubstituted piperazine group may also be the base where more than one equivalent of monosubstituted piperazine is present. Preferably about 2 equivalents are used.

Where a supplementary base is used it either does not react with the sulphonyl chloride moiety (such as a metal oxide, carbonate or bicarbonate) or it reacts with the sulphonyl chloride moiety in such a way as to keep it activated to nucleophilic attack (e.g. a tertiary amine such as triethylamine). The amine NH(R3)(R5) may also act as a base, in which case preferably more than one equivalent is present, more preferably about 2 equivalents (or more).

The compounds of formula (XVI) can be formed from compounds of formula (XX) in the presence of a chlorinating or brominating agent such as thionyl chloride or thionyl bromide more preferably in the presence of a halogenation catalyst, more preferably still thionyl chloride or thionyl bromide in the presence of dimethylformamide. The thionyl chloro/bromo can also act as the solvent, but more preferably the reaction takes place or in an appropriate other solvent such as toluene. In such case only stoicheometric amounts of thionyl chloride/bromide would be required, preferably at least 2 molar equivalents, more preferably at least 5 molar equivalents.

It is possible to undertake the four step conversion of (XX) to (XB) in a single telescoped step, without intermediate product isolation, using the same solvent throughout (hereinafter the "telescoping solvent"). Thus where X' is an alkoxy group (—OR³ group), steps (XX) to (XB) can be telescoped together using a single solvent such as a water immiscible inert organic solvent. More preferably a hydrocarbon solvent (such as toluene, xylene, anisole, chlorobenzene, hexane, heptane, octane, nonane, decane, cyclohexane, methylcyclohexane) or ethers (such as dibutyl ether, diphenyl ether) or ketones (such as methylisobutylketone, methylethylketone) or esters (such as ethyl acetate, butyl acetate) or dimethylformamide. More preferably still a hydrocarbon solvent (such as toluene, xylene, anisole, chlorobenzene, octane, nonane, decane, methylcyclohexane) or ethers (such as dibutyl ether, diphenyl ether) or esters (such as ethyl acetate, butyl acetate). More preferably still the telescoping solvent is toluene.

The intermediate of formula (XX) is formed from a compound of formula (XVII) in the presence of an agent which will form a protecting group (P) for the carboxylic acid (i.e. to form the —COP group). Preferably said agent is an esterification agent, to form a carboxylic acid ester (wherein, e.g. P will be alkoxy and the protecting forming agent will be an alcohol) such as a $C_1$–$C_6$ carboxylic acid ester which will be carried through the reaction scheme and hydrolised under basic conditions to the carboxylic acid function of compound (XB). Most preferably the esterification agent is ethanol. An additional solvent such as toluene may be appropriate.

The intermediate of formula (XVII) is formed from 2-hydroxynicotinic acid or a salt thereof in the presence of a sulphonylating agent, more preferably an agent comprising $SO_3$ (ideally at least 1 molar equivalent of $SO_3$), for example using $SO_3$ in an organic solvent (e.g. THF, dioxan and heptane) or an aprotic solvent (e.g. nitrobenzene, nitromethane, 1,4-dioxane, dichloromethane) or a mineral acid as solvent (e.g. sulphuric acid) or in a liquid carboxylic acid as solvent (e.g. acetic acid) or THF or heptane. More preferably still, the sulphonylating agent is oleum ($SO_3$ in sulphuric acid) such as about 20% to 30% oleum.

Compounds of the general formula (IXB) are formed by the reaction of intermediates of general formula (XB) with compounds of the general formula (VII), as detailed hereinbefore in the presence of a coupling agent, such as N,N'-carbonyldiimidazole and a suitable solvent, such as ethyl acetate.

Methods for the preparation of compounds of the general formula (VII) are described hereinafter.

In a preferred embodiment of Scheme 1, X' is an —OR³ alkoxy group and so Q' in compound (XIV) represents OR³. Preferably OR³ is a $C_1$ to $C_6$ alkoxy group, more preferably a $C_1$ to $C_4$ primary or secondary alkoxy group and especially ethoxy. However for other leaving groups the general method for Scheme 1 would apply.

This preferred embodiment of Scheme 1 is illustrated in Scheme 2.

Scheme 2

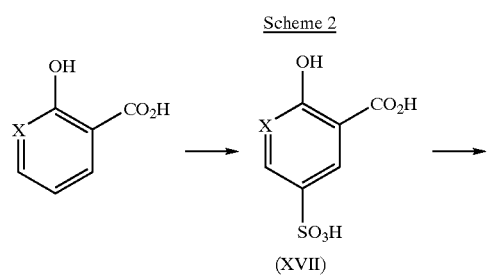

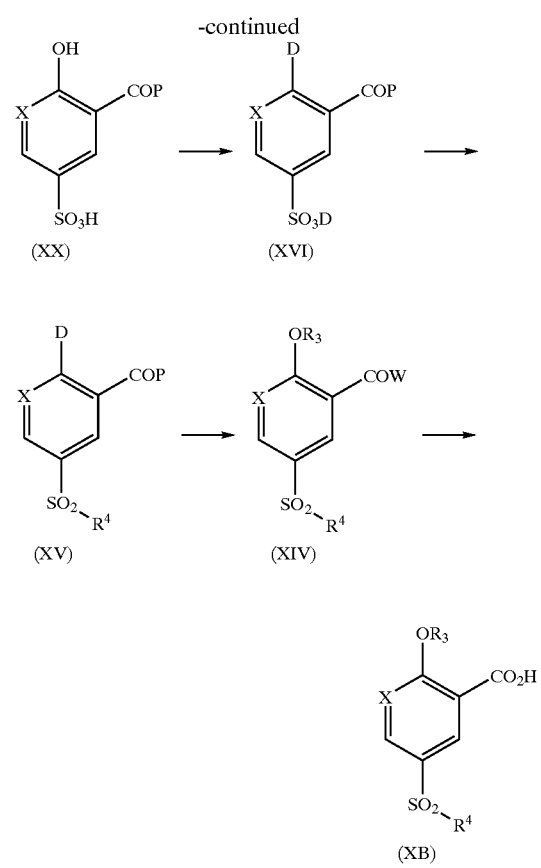

In Scheme 2 the intermediate of formula (XB) is formed from a compound of formula (XIV) by removal of protecting group P by a deprotecting agent, advantageously by saponification in the presence of a hydroxide base such as sodium hydroxide, preferably in an appropriate solvent such as water and toluene.

The intermediate of formula (XIV) is formed from a compound of formula (XV) in the presence of an appropriate $C_1$–$C_6$ alkoxide nucleophile (—OR³), (such as a primary or secondary alkoxide), preferably a metal alkoxide of the formula Z'OR³, wherein the metal (Z') is as defined hereinbefore for Z'OR, such as sodium ethoxide, preferably in an appropriate solvent such as toluene or R³OH, wherein R³OH is as defined hereinbefore and is preferably ethoxy. D in compounds of formulae (XV) and (XVI) is Cl or Br, more preferably D is Cl.

The intermediate of formula (XV) is formed from a compound of formula (XVI) by reaction with N-substituted piperazine, preferably in the presence of a base, such as triethylamine or excess N-substituted piperazine, preferably in an appropriate solvent such as toluene.

The intermediate of formula (XVI) is formed from a compound of formula (XX) in the presence of a chlorinating or brominating agent as defined for the same step in Scheme 1 such as thionyl chloride or bromide, preferably thionyl chloride or bromide/dimethylformamide. The former can also act as the solvent, but more preferably the reaction takes place in an appropriate other solvent, such as toluene. In such a case only stoicheiometric amounts of thionyl chloride/bromide would be required, preferably as at least 2 molar equivalents more preferably at least 5 molar equivalents.

The intermediate of formula (XX) is formed from a compound of formula (XVII) in the presence of an agent which will form a protecting group (P) for the carboxylic acid (i.e. to form the —COP group) as defined herein before. Preferably said agent is an esterification agent, to form a carboxylic acid ester such as a $C_1$–$C_6$ carboxylic acid ester which will be carried through the reaction scheme and hydrolysed under basic conditions to the carboxylic acid function of compound (XB). Most preferably the esterification agent is ethanol. An additional solvent such as toluene may be utilised as appropriate.

The intermediate of formula (XVII) is formed from 2-hydroxynicotinic acid with a sulphonylating agent such as 30% oleum.

Again it is possible to undertake the four step conversion of (XX) to (XB) in a single telescoped step (as set out hereinbefore) in the same pot, without intermediate product isolation, using the same solvent (herein the "telescoping" solvent) throughout. The list of solvents described with respect to Scheme 1 are directly applicable here. Most preferably the solvent is toluene.

For example after formation of compound (XVI), the excess chlorinating/brominating agent could be azeotroped off at the azeotrope temperature of the said agent and the telescope solvent. After formation of compound (XV), the HBr/HCl (i.e. HD) salts which are formed could be washed out (in aqueous) or filtered from the reaction vessel and the remainder of the aqueous solvent (where applicable) azeotroped off with some of the telescoping solvent. In the formation of compound (XIV), if the alkoxide used to introduce $OR^3$ is dissolved in solvent (such as ethanol), then this solvent could again be azeotroped off with some of the telescoping solvent. If solid alkoxide is used then this latter azeotroping step is not required. Most preferably the telescoping solvent for any telescoped steps of Scheme 2 is toluene.

It will be appreciated that salts of the compounds of Schemes 1 and 2 can be formed in accordance with the invention by converting the relevant compound to a salt thereof (either in situ or as a separate step). Also an acid addition salt of the compound of formula (I) can be formed in accordance with the invention.

1.4. Clearly, for certain compounds of formulae (I), wherein $VR^3$ is $OR^3$, by exploiting the cyclisation and alkoxide exchange methodology described in sections 1.2 and 2.1 herein, it may be particularly advantageous to generate a compound of formula (I) from a compound of the general formula (IXCa), wherein the 2-alkoxy group of the 5-(pyridin-3-yl) substituent in the former is different from that in the latter, directly in a "one-pot reaction". To achieve this an alternative alcohol ($R^3OH$) should be used wherein the alkyl chain of the —$R^3$ group of the alcohol is different from that of the —$R^{3a}$group on the starting compound of general formula (IXCa). When the alcohol which is to provide the alternative 2-alkoxy group (—$OR^3$) is too scarce or expensive to be employed as the reaction solvent, then it will be expedient to use a suitable alternative such as 1,4-dioxan as reaction solvent with the required alcohol ($R^{3a}OH$) present in an amount sufficient to effect the desired conversion, typically from about 1 to about 2 molecular equivalents. (IXCa) and $R^{3a}$ are as defined hereinbefore.

When the compound is of formula (Ic) or (Id) synthesis can be achieved by the following general route:

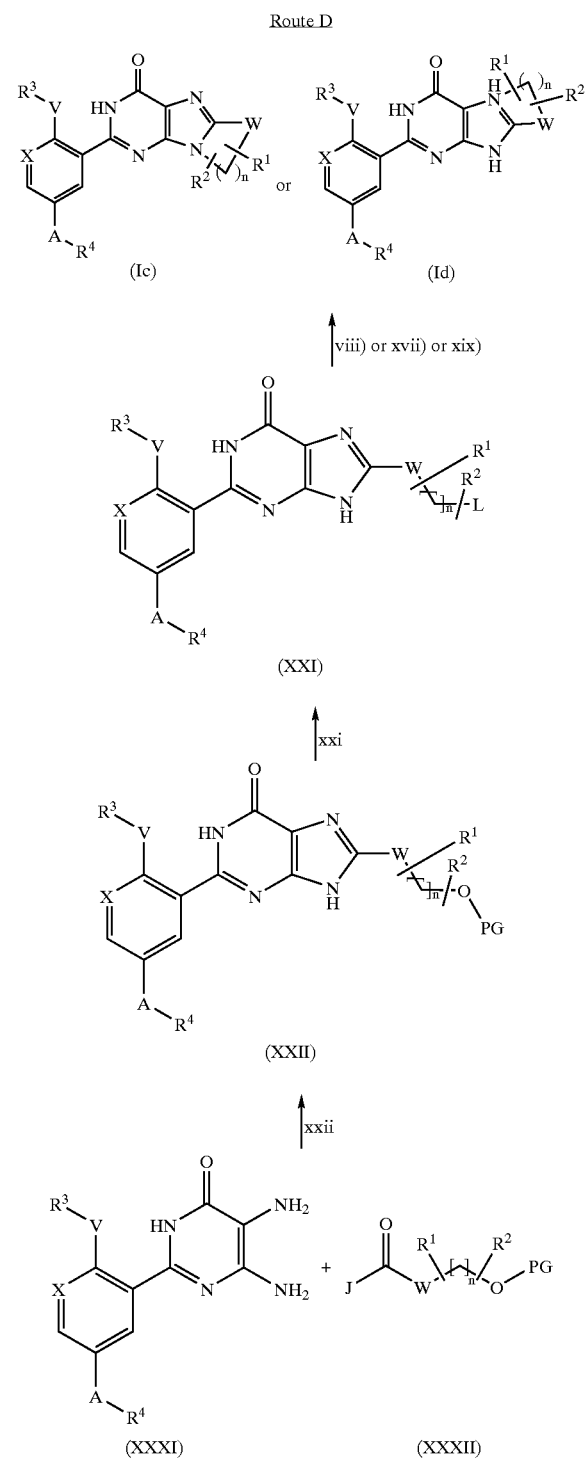

which involves the following steps:

xxi) deprotection of the silyl protecting group (PG), using standard methodology (see, for example, Protective Groups in Organic Synthesis", by Greene and Wutz, Wiley-Interscience 1991), followed by conversion of the alcohol into a suitable leaving group, L (eg mesylate or Chloro), using standard methodology.

xxii) reaction of the diamine (XXXI) with either aldehyde (XXXII) (ie when J is H) or with an acid or acid derivative (i.e. when J is OH or ORalk). The protecting group (PG) on O, is a conventional group as described in the standard textbooks referred to above and suitable conditions are described in European patent 1092718. Preferably the protecting group is a silyl derivative (eg t-Bu(Me)$_2$Si).

The diamine (XXXI) can be prepared as described in European patent 1092718 or U.S. Pat. Nos. 3,819,631 and 4,039,544. Similarly, the aldehyde, acid or acid derivative (XXXII) can also be prepared as described in European patent 1092718.

The synthesis of compounds of formula (Ib) can be achieved from compound (VIIb) by the following general route:

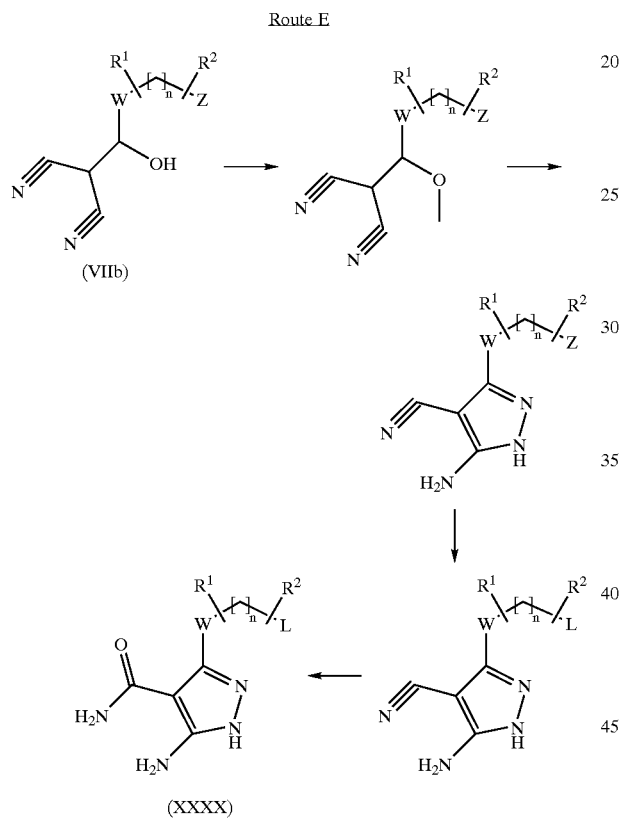

In the above scheme, L is a suitable leaving group, (eg chloro, mesylate) and Z is a group that is easily converted into L, eg O-PG, as above. The synthesis of the required pyrazoles is as described in European patent 0995751. Compound (XXXX) is then reacted with (XA), (XB), or (XC) in an analogus manner to the reaction of (VII) with (XA), (XB), or (XC) described above. The coupled product is then cyclised in ananalogus manner to that described in Section 1 above, followed by a further reaction according to step viii) in Route D to yield the compound of formula (Ib).

2. In a further generally applicable process, compounds of the general formula (I), may be prepared from "alternative" compounds of the general formula (I), wherein said process may comprise either interconversion of differing —OR$^3$ groups, interconversion of X and —OR$^3$ groups or interconversion of —OR$^3$ and —NR$^3$R$^5$ groups wherein X, R$^3$ and R$^5$ are as defined hereinbefore.

2.1 As mentioned earlier, certain compounds of formulae (I), can be interconverted by inducing alkoxide exchange or displacement at the 2-position of the 5-(pyridin-3-yl) substituent. This may be achieved, by treating the appropriate alcohol (of formula R$^{3a}$OH wherein the R$^{3a}$ alkyl group is as defined hereinbefore and is different from the R$^3$ group on the starting material (I), with an alkali metal salt of a sterically hindered alcohol or amine or carbonate in order to generate the required alkoxide anion which then reacts with the substrate. Typically, in a two-step procedure, a mixture of from about 1 to about 8, more preferably from about 5 to about 8, and especially from about 4 to about 8 molecular equivalents of potassium bis(trimethylsilyl)amide and the required alcohol (of formula R$^{3a}$OH) as solvent is heated at from about 80° C. to about 100° C. for about 25 minutes to about 1 hour, followed by addition of the compound of formula (I) and heating of the reaction mixture at from about 100° C. to about 130° C. for from about 6 to about 24 hours. Alternatively, in a one-step procedure, the substrate may be treated directly, in the required alcohol as solvent, with from about 1.2 to about 6, preferably from about 4 to about 6 molecular equivalents of, for example, potassium bis(trimethylsilyl)amide, potassium t-butoxide or cesium carbonate at from about 80° C. to about 130° C. A hydroxide trapping agent may be optionally included in such alkoxide exchange reactions.

2.2 Alternatively, certain compounds of the general formula (I), wherein VR$^3$ is —OR$^3$ may be obtained from compounds of the general formula (XXX):

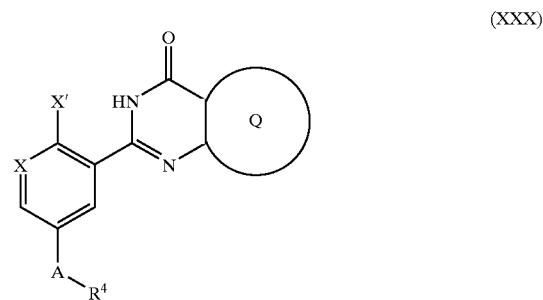

wherein A etc are as previously defined and wherein X' is anything other than —OR$^3$ by reaction in the presence of —OR$^{3-}$ optionally in the presence of a hydroxide trapping agent as defined hereinbefore.

2.3 In a yet further alternative synthesis compounds of the general formula (I), wherein VR$^3$ is NR$^3$R$^5$ may be generated directly from a compound of general formula (I) wherein VR$^3$=OR$^3$. When VR$^3$ is OR$^3$, the substrate may be treated with an excess of R$^3$R$^5$NH, or a suitable acid addition salt thereof, in the presence of an excess of a non-nucleophilic base such as a sterically hindered amine or a suitable inorganic base in a suitable solvent. Typically, R$^5$R$^6$ NH is used as the free base with about a 3-fold excess (over the substrate) of potassium bis(trimethylsilyl)amide (KHMDS) in dimethylformamide (DMF) as solvent at about 100° C. Alternatively, an excess of R$^3$R$^5$NH may be used as the solvent and the reaction conducted in the presence of about a 50% excess of copper(II) sulphate at up to the reflux temperature of the reaction medium. Where the desired amino substituent on the compound of the formula (I), is —NR³R⁵ and one of either R³ or R⁵ is H, then the exchange reaction may be carried out by refluxing with the appropriate amine, and copper(II)sulphate penta- or hepta-hydrate or anhydrous copper (II) sulphate or KHDMS in DMF. Typically, to exchange the OR³ group for alternative amines of the formula NHR³R⁵, such as compounds wherein R³ or R⁵ are selected from aliphatic or cyclic amines, optionally including oxygen (e.g. morpholine), then the reaction is preferably carried out by treating with the appropriate amine and about 3 equivalents of potassium bis(trimethylsilyl) amide in DMF for about 18 hours at 100° C.

3. In a yet further alternative process, a compound of the general formula (I) may be prepared from a compound of general formulae (IIA) or (IIC) respectively:

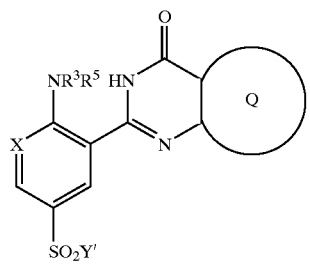
(IIA)

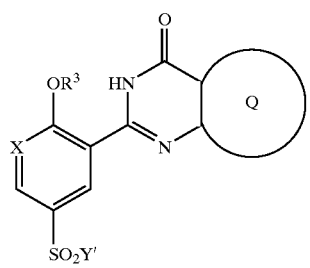
(IIC)

wherein Y' is halo, preferably chloro, and wherein A etc are as previously defined, by a reaction with a suitable compound such as a 4-methyl or 4-ethyl-piperazinyl compound as described for the preparation of compounds of formula (XA) and (XB) from compounds of formula (VIIA) and (VIIIB) respectively.

Alternatively, a compound of the general formula (I), (Ia) or (Ib) may be prepared from a compound of the general formula (IIB):

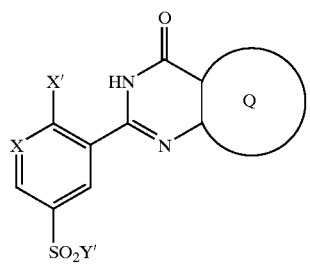
(IIB)

wherein A, V, W, X, X', Y', n, m, and R¹ to R¹⁷ are as previously defined herein for compounds of formula (I) via reaction with a suitable compound such as a 4-methyl or 4-ethyl piperazinyl compound followed by an optional displacement reaction in the presence of a hydroxide trapping agent and —OR³ as detailed hereinbefore for the preparation of compound (I) from compound (IXB) or (XXX).

3.1 A compound of general formulae (IIA) or (IIB) or (IIC) may be prepared from a compound of general formula (IVA) or (IVB) or (IVC) respectively:

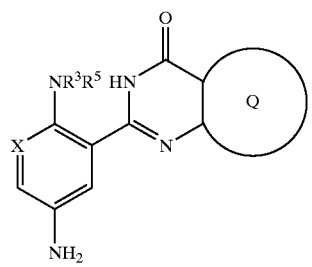
(IVA)

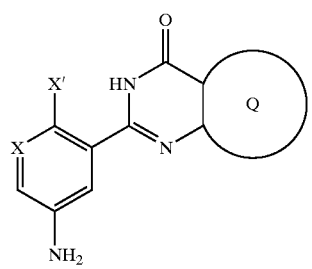
(IVB)

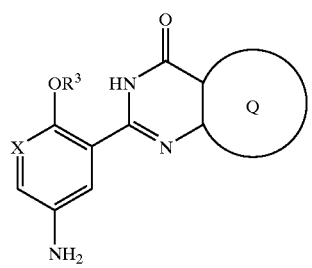
(IVC)

wherein R¹ etc are as previously described herein, by the application of known methods for converting amino to a SO₂Y'. Such reactions are previously described for the preparation of compounds of the general formulae (VIIIA) and (VIIIB) from compounds of the general formulae (XIA) and (XIB) respectively.

A compound of the general formula (IVA) or (IVB) or (IVC) may be prepared by cyclisation of a compound of the general formula (VA) or (VB) or (VC) respectively:

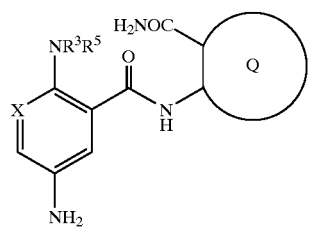
(VA)

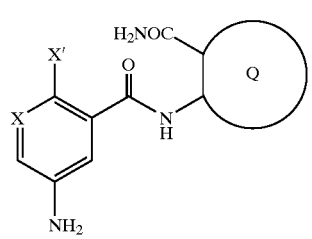
(VB)

(VC)

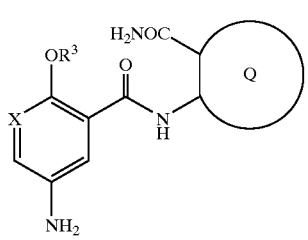

wherein R¹ etc are as previously defined herein and wherein the conditions for cyclisation are analogous to those previously described for cyclisation of the compounds of general formulae (IXA), (IXB) or (IXC).

A compound of formula (VA) or (VB) or (VC) may be prepared by reduction of a compound of formula (VIA) or (VIB) or (IVC) respectively:

(VIA)

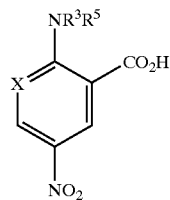

(VIB)

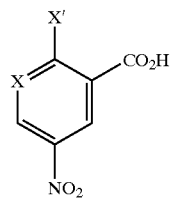

(VIC)

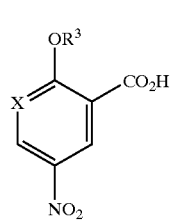

wherein R¹ etc are as previously defined for compounds of the general formulae (VA), (VB) and (VC), by conventional catalytic or catalytic transfer hydrogenation procedures as previously detailed for preparation of compounds of the general formulae (XIA) or (XIB) from compounds of the general formulae (XIIA) or (XIIB) respectively.

A compound of formula (VIA), (VIB) or (VIC) may be prepared by reaction of a compound of formula (VII) as defined previously herein with a compound of formula (XIIA) or (XIIB) or (XIIC) respectively:

(XIIA)

![XIIA structure]

(XIIB)

![XIIB structure]

(XIIC)

![XIIC structure]

wherein R³, R⁵, X and X' are as previously defined for compounds of the general formulae (VIA) or (VIB) or (VIC). Again, as previously detailed a conventional amine protecting group strategy is preferred for (XIIA) when NR³R⁵ is a primary or secondary amino group. The coupling reaction is analogous to the reactions of (VII) with the compounds of general formulae (XA) or (XB) or (XC) already described herein.

3.2 A compound of general formulae (IIA) or (IIB) or (IIC) may be prepared from a compound of formula (IVA) or (IVB) or (IVC) respectively as described hereinbefore wherein said compound of the general formulae (IVA) or (IVB) or (IVC) may be prepared by direct cyclisation of a compound of the general formula (VIA) or (VIB) or (VIC), respectively, wherein R¹ etc are as previously defined herein and wherein the conditions for said direct cyclisation are analogous to the previously described cyclisation for compounds of the general formulae (IXA) or (IXB) or (IXC) and wherein said cyclisation is followed by reduction of the resultant intermediate compounds according to the methods previously detailed herein to provide compounds of the general formulae (IVA) or (IVB) or (IVC) from compounds of the general formulae (VA) or (VB) or (VC).

Compounds of the general formula (XIIC) wherein X is Cl may be prepared from 2-hydroxy nicotinic acid via nitration followed by esterification then chlorination of the suitably protected nicotinic acid and subsequent ester hydrolysis.

Compounds of the general formula (XIIIC) (i.e. compounds of general formula (XIIIB wherein X is —OR³) can be prepared by analogy with the methods detailed previously herein.

The intermediate pyrazole and carboxylic acid compounds described above when neither commercially available nor subsequently described, can be obtained either by analogy with the processes described in the Preparations section or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections which allow the compounds defined by formulae (I), (IA) or (IB) to be obtained.

The pharmaceutically acceptable acid addition salts of the compounds of formulae (I) which contain a basic centre may also be prepared in a conventional manner. By way of illustration, acid addition salts of compounds of formula (I) can be formed by reacting a compound of formula (I) with an equimolar or excess amount of the appropriate acid, either neat or in a suitable solvent. The salt may then be precipitated out of solution and isolated by filtration or the reaction solvent can be stripped off by conventional means such as by evaporation under vacuum. Typical salts which can be used in the schemes of 1 and 2 are described in WO 99/54333. Example of salts of compound I are the p-toluenesulfonate, benzenesulfonate, camphorsulfonate and ethanesulfonate respectively.

The preferred compounds of formula Ia in which $AR^4$ is $SO_2Het^1$ may be prepared by cyclisation of a corresponding compound of formula IXA.

The reaction is typically performed in a sealed vessel in the presence of bis(trimethylsilyl)acetamide or potassium hexamethyidisilazide with a suitable solvent (e.g. an alcohol), optionally with an equivalent of ethyl acetate. The alcohol is selected such that the alkyl group corresponds to group $R^3$, for example ethanol is used when $R^3$ is ethyl. Transalkylation can be effected by using an alternative alcohol as the solvent.

Likewise, the preferred compounds of formula IXA in which $AR^4$ is $SO_2Het^1$ may be prepared by reaction of a corresponding compound of formula XA, XB, or XC with a compound of formula VII. The preferred compounds of formula XA, XB, or XC can be formed as previously described.

Compounds of formula Ia may also be prepared by reaction of a corresponding compound of formula IaLG:

(IaLG)

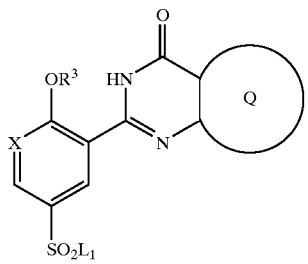

wherein $L^1$ represents a suitable leaving group (e.g. halo), and $R^1$ etc are as hereinbefore defined, with a compound of formula $Het^1$-H, provided that the 1-N atom of the piperazine is attached to the H-atom.

Compounds of formula IaLG can be formed using synthetic methodology described in published European patent application 1092719.

Compounds described above and derivatives thereof, when not commercially available or not subsequently described, may be obtained either by analogy with the processes described hereinbefore, or by conventional synthetic procedures, in accordance with standard techniques, from readily available starting materials using appropriate reagents and reaction conditions.

Substituents on phenyl and Het groups in the above-mentioned compounds may be introduced, removed and interconverted, using techniques which are well known to those skilled in the art. For example, compounds of formula I as described hereinbefore, in which either $R^1$ or $R^2$ represents $C_{1-6}$ alkyl substituted by an alkylphenyl group, may be prepared by alkylation of a corresponding compound of formula I in which $R^1$ or $R^2$ represents $C_{1-6}$ alkyl substituted by a phenyl group. The reaction may be performed using methods which are well known to those skilled in the art.

The skilled person will also appreciate that various standard substituent or functional group interconversions and transformations within certain compounds of formula I will provide other compounds of formula I; for example, for compounds of formula I in which $R^3$ represents alkyl, alkoxide exchange at the 2-position of the pyridin-3-yl substituent. Moreover, certain compounds of formula I, for example those in which $Het^1$ represents a 4-$R^6$-1-piperazinyl group, in which $R^6$ does not represent H, may be prepared directly from the corresponding piperazine analogues in which $R^6$ represents H, using standard procedures (e.g. alkylation).

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it is desirable to protect include hydroxy, amino and carboxylic acid. Suitable protecting groups for hydroxy include trialkylsilyl and diarylalkylsilyl groups (e.g. tert-butyidimethylsilyl, tert-butyldiphenylsilyl or trimethylsilyl), tetrahydropyranyl and alkylcarbonyl groups (e.g. methyl- and ethylcarbonyl). Suitable protecting groups for amino include tertbutyloxycarbonyl, 9-fluorenylmethoxycarbonyl or benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art.

The use of protecting groups is fully described in "Protective Groups in Organic Chemistry", edited by JWF McOmie, Plenum Press (1973), and "Protective Groups in Organic Synthesis", 2nd edition, TW Greene & PGM Wutz, Wiley-Interscience (1991).

Persons skilled in the art will also appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Pharmaceutically acceptable acid addition salts of the compounds of formula I that contain a basic centre may be prepared in a conventional manner. For example, a solution of the free base may be treated with the appropriate acid, either neat or in a suitable solvent, and the resulting salt may then be isolated either by filtration or by evaporation under vacuum of the reaction solvent.

Pharmaceutically acceptable base addition salts can be obtained in an analogous manner by treating a solution of a compound of formula I with the appropriate base. Both types of salt may be formed or interconverted using ion-exchange resin techniques.

All of the above reactions and the preparations of novel starting materials using in the preceding methods are conventional and appropriate reagents and reaction conditions for their performance or preparation as well as procedures for isolating the desired products will be well-known to those skilled in the art with reference to literature precedents and the Examples and Preparations hereto.

The syntheses of the compounds of the invention and of the intermediates for use therein are illustrated by the following Examples and Preparations. A number of the compounds included in the Preparations section are compounds of the formula (I), (IA) or (IB) and are thereby examples of compounds according to the present invention.

$^1$H Nuclear magnetic resonance (NMR) spectra were recorded using either a Varian Unity 300 or a Varian Inova 400 spectrometer and were in all cases consistent with the proposed structures. Characteristic chemical shifts ($\delta$) are given in parts-per-million downfield from tetramethylsilane using conventional abbreviations for designation of major peaks: e.g. s, singlet; d, doublet; t, triplet; q, quartet; m, multiplet; br, broad.

Mass spectra (m/z) were recorded using a Fisons Instruments Trio mass spectrometer in the thermospray ionisation mode.

Room temperature means 20 to 25° C.
WSCDI=1-(3-dimethylaminopropyl)-3-ethylcarbodiimide hydrochloride
DCC=N,N'-dicyclohexylcarbodiimide
HOAT=1-hydroxy-7-azabenzotriazole
HOBT=1-hydroxybenzotriazole hydrate
PyBOP®=Benzotriazol-1-yloxytris(pyrrolidino)phosphonium hexafluorophosphate
PyBrOP=bromo-tris-pyrrolidino-phosphonium hexafluorophosphate
Mukaiyama's reagent=2-chloro-1-methylpyridinium iodide
KHMDS=potassium bis(trimethylsilyl)amide
Hünig's base=N-ethyldiisopropylamine
Et$_3$N=triethylamine
NMM=N-methylmorpholine
Boc=tert-butoxycarbonyl
CBz=benzyloxycarbonyl
(Boc)$_2$O=di-tert-butyl dicarbonate
MeOH=methanol
EtOH=ethanol
EtOAc=ethyl acetate
THF=tetrahydrofuran
DCM=dichloromethane
TFA=trifluoroacetic acid

PREPARATIONS

Preparation 1

5,6-Dihydro-4H-pyrrolo[1,2-c][1,2,3]oxadiazol-7-ium-3-olate

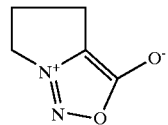

N-Nitroproline (17.0 g, 118 mmol) was suspended in ether (400 ml) and cooled in ice. Trifluoroacetic anhydride (16.5 ml, 120 mmol) was then added dropwise over 30 minutes and the mixture left to warm to room temperature whilst stirring over 16 hours. The mixture was evaporated in vacuo to an oil and purified by column chromatography on silica gel using an eluant of ethyl acetate to afford the title compound, 9.8 g.

$^1$Hnmr (CDCl$_3$, 400 MHz) $\delta$: 2.75 (2H, m), 2.90 (2H, t), 4.40 (2H, t)

LRMS: m/z 127 (MH)$^+$

Preparation 2

(5R)-5-Methyl-4,5,6,7-tetrahydro[1,2,3]oxadiazolo[3,4-a]pyridin-8-ium-3-olate

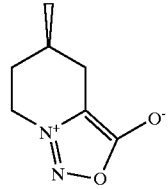

Concentrated hydrochloric acid (6.0 ml) was added to a suspension of (2R,4R)-4-methyl-2-piperidinecarboxylic acid (Biochem. Biophys. Res. Commun. 1981; 101(2); 440) (10 g, 7.03 mmol), in water (30 ml) and this solution cooled to −5° C. A solution of sodium nitrite (5.3 g, 7.7 mmol), in water (20 ml) was then added, and this solution stirred at room temperature for 2 hours. The mixture was extracted with dichloromethane, twice, and the combined organic extracts were dried (MgSO$_4$) and evaporated under reduced pressure to give a white solid. Trifluoroacetic anhydride (11 ml, 7.70 mmol) was added to a cooled (−3° C.) solution of the intermediate product in ether (200 ml) and the reaction stirred overnight at room temperature. The mixture was evaporated under reduced pressure, and the residue purified by column chromatography using ethyl acetate as the eluant. The title compound was obtained as a brown crystalline solid, 7.1 g.

$^1$Hnmr (CDCl$_3$, 300 MHz) $\delta$: 1.19 (3H, d), 1.65–1.82 (1H, m), 2.00–2.24 (3H, m), 2.82 (1H, m), 4.20 (1H, m), 4.44 (1H, m).

LRMS m/z: 172.1 (MNH$_4$)$^+$

Preparation 3

Ethyl 5,6-dihydro-4H-pyrrolo[1,2-b]pyrazole-2-carboxylate

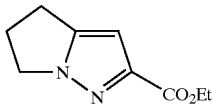

A mixture of the product of preparation 1 (9.8 g, 78 mmol) and ethyl propiolate (24 ml, 236 mmol) was heated under reflux in xylene (150 ml) for 8 hours. The cooled reaction mixture was evaporated to an oil, dissolved in ethyl acetate and washed with sodium carbonate solution. The aqueous layer was re-extracted with dichloromethane and the combined organic extracts were dried ($Na_2SO_4$), filtered and evaporated in vacuo to an oil, 13 g. This was purified by column chromatography on silica gel using ethyl acetate as eluant to afford 9 g of a mixture of C-1 and C-2 regioisomers. The regioisomers were then separated by column chromatography on silica gel using an eluant of ether to afford 4.1 g of the desired C-1 regioisomer.

$^1$Hnmr (CDCl$_3$, 400 MHz) δ: 1.40 (3H, t), 2.63 (2H, m), 2.92 (2H, t), 4.18 (2H, t), 4.38 (2H, q), 6.55 (1H, s)

Preparation 4

Ethyl 4,5,6,7-tetrahydropyrazolo[1,5-a]pyridine-2-carboxylate

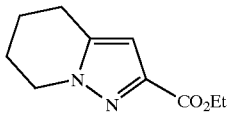

A mixture of 4,5,6,7-tetrahydro[1,2,3]oxadiazolo[3,4-a]pyridin-8-ium-3-olate (Heterocycles; 1990; 31; 481), (13.0 g, 93 mmol), and ethyl propiolate (28.5 ml, 278 mmol), in xylene (250 ml) was heated under reflux for 2 hours. The cooled mixture was evaporated under reduced pressure. The residual oil was purified by column chromatography on silica gel using ether as the eluant, to afford the title compound as an oil, 5.82 g.

$^1$Hnmr (CDCl$_3$, 400 MHz) δ: 1.39 (3H, t), 1.88 (2H, m), 2.06 (2H, m), 2.82 (2H, t), 4.20 (2H, t), 4.39 (2H, q), 6.55 (1H, s).

LRMS m/z: 195.2 (MH)$^+$

Preparation 5

Ethyl (5R)-5-methyl-4,5,6,7-tetrahydropyrazolo[1,5-b]pyridine-2-carboxylate

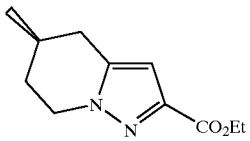

A mixture of the compound from preparation 2 (7.0 g, 46.0 mmol) and ethyl propiolate (13.5 g, 140 mmol) in xylene (100 ml) was heated under reflux for 4 hours. The cooled mixture was evaporated under reduced pressure and the residue purified by column chromatography on silica gel using ether as eluant. The product was re-columned on silica gel, using an elution gradient of ethyl acetate:dichloromethane (0:100 to 50:50) to give a brown oil. This was recrystallised from diisopropyl ether to afford the title compound as a pale yellow solid, 2.0 g.

$^1$Hnmr (CDCl$_3$, 300 MHz) δ: 1.14 (3H, d), 1.38 (3H, t), 1.75 (1H, m), 2.01 (2H, m), 2.38 (1H, m), 2.95 (1H, m), 4.12 (1H, m), 4.38 (3H, m), 6.50 (1H, s).

Preparation 6

Diethyl 1-(5-ethoxy-5-oxopentyl)-1H-pyrazole-3,5-dicarboxylate

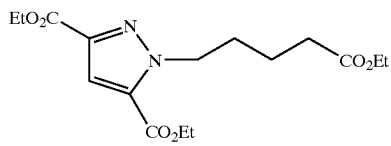

Diethyl 3,5-pyrazoledicarboxylate (50 g, 0.236 mol) was dissolved in acetonitrile (500 ml) under a nitrogen atmosphere. Potassium carbonate (33 g, 0.236 mol) was added followed by ethyl 5-bromovalerate (37.7 ml, 0.235 mol) and the mixture heated under reflux for 2 hours. The solvent was removed in vacuo leaving a clear oil which was partitioned between ethyl acetate and water. The organic phase was separated and the aqueous phase further extracted with ethyl acetate (×2). The organic extracts were combined, dried (MgSO$_4$), filtered and concentrated under reduced pressure to give 75 g of the title product.

$^1$Hnmr (CDCl$_3$, 300 MHz) δ: 1.25 (3H, t), 1.40 (6H, m), 1.65 (2H, m), 1.90 (2H, m), 2.35 (2H, t), 4.10 (2H, q), 4.35 (4H, m), 4.65 (2H, t), 7.35 (1H, s)

LRMS: m/z 341 (MH)$^+$

Preparation 7

Diethyl 1-(4-ethoxy-4-oxobutyl)-1H-pyrazole-3,5-dicarboxylate

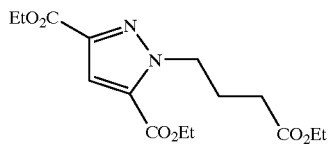

The title compound was obtained as a solid (quantitatively), from diethylpyrazole 3,5-dicarboxylate and ethyl 4-bromobutyrate, following the procedure described in preparation 6.

$^1$Hnmr (CDCl$_3$, 300 MHz) δ: 1.22 (3H, t), 1.39 (6H, m), 2.20 (2H, m), 2.32 (2H, m), 4.12 (2H, q), 4.34–4.46 (4H, m), 4.72 (2H, t), 7.34 (1H, s).

Preparation 8

2-[(tert-Butoxycarbonyl)amino]ethyl Methanesulfonate

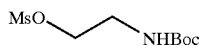

Triethylamine (27.0 ml, 194 mmol) was added to a solution of tert-butyl 2-hydroxyethyl carbonate (25.0 g, 155 mmol) in dichloromethane (500 ml), and the solution cooled in an ice-bath. Methanesulphonyl chloride (14.4 ml, 186 mmol) was added dropwise over 15 minutes, and the reaction stirred at room temperature for 2 hours. The mixture was washed with saturated sodium bicarbonate solution (500 ml), evaporated under reduced pressure and re-dissolved in ethyl acetate. The solution was washed again with 3% aqueous sodium bicarbonate solution (300 ml), then brine (300 ml), dried (MgSO$_4$), and evaporated under reduced pressure to afford the title compound as an oil, 38.2 g.

$^1$Hnmr (CDCl$_3$, 300 MHz) δ: 1.44 (9H, s), 3.02 (3H, s), 3.46 (2H, m), 4.28 (2H, t), 4.90 (1H, s).

Preparation 9

4-Nitro-1H-pyrazole-3,5-dicarboxylic Acid

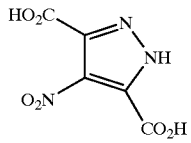

Fuming sulphuric acid (105 ml) was added dropwise over 45 minutes to ice-cooled fuming nitric acid (8 ml), so as to maintain the internal temperature below 20° C. Once addition was complete, the mixture was warmed to 40° C., pyrazole-3,5-dicarboxylic acid (1 25 g, 0.80 mol) was added portionwise over 75 minutes, so as to maintain the reaction temperature below 50° C., and the reaction then stirred at 60° C. for 18 hours. The cooled mixture was poured onto ice (1 Kg), and flaked potassium hydroxide carefully added with stirring, until the solution pH was 2. The resulting precipitate was filtered, and triturated with boiling water (500 ml), to afford the title compound as a white solid, 123 g. Mp 325–327° C.

Preparation 10

4-Nitro-1H-pyrazole-3,5-dicarboxylic Acid Dimethyl Ester

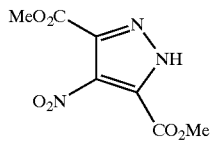

Thionyl chloride (290 ml, 3.98 mol) was added dropwise over 2 hours, to an ice-cooled suspension of the compound from preparation 9 (123 g, 0.61 mol) in dry methanol (1200 ml), and the reaction stirred under reflux for 48 hours. The cooled mixture was concentrated under reduced pressure, partitioned between water (500 ml) and dichloromethane (500 ml), and filtered. The phases were separated, the aqueous layer extracted with dichloromethane (4×250 ml), the combined organic solutions dried (Na$_2$SO$_4$), and evaporated under reduced pressure to afford the title compound, as a white solid, 74.6 g.

$^1$Hnmr (CDCl$_3$, 300 MHz)δ: 4.00 (6H, s).

LRMS: m/z 247 (MNH$_4$)$^+$

Anal. Found: C, 36.39; H, 2.98; N, 18.15. C$_7$H$_7$N$_3$O$_6$ requires C, 36.69; H, 3.08; H, 18.34%.

Preparation 11

Dimethyl 1-{2-[(tert-butoxycarbonyl)amino]ethyl}-4-nitro-1H-pyrazole-3,5-dicarboxylate

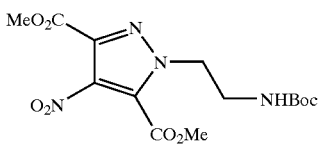

A solution of the mesylate from preparation 8 (36 g, 0.15 mol) in acetonitrile (100 ml) was added to a mixture of the pyrazole from preparation 10 (32.8 g, 0.143 mol) and potassium carbonate (24.8 g, 0.18 mol) in acetonitrile (150 ml) and N,N-dimethylformamide (250 ml), and the reaction stirred at 50° C. for 3 days. The mixture was diluted with ethyl acetate (700 ml), and this mixture washed consecutively with aqueous sodium bicarbonate solution (700 ml) and water (3×700 ml). The organic layer was dried (Na$_2$SO$_4$) and evaporated under reduced pressure. The residue was purified by column chromatography on silica gel using dichloromethane:methanol (97:3) as eluant to afford the title compound as an oil, 17.5 g.

$^1$Hnmr (CDCl$_3$, 300 MHz) δ: 1.39 (9H, s), 3.62 (2H, m), 3.94 (6H, s), 4.71 (3H, m).

Preparation 12

Diethyl 4-oxo-4,5,6,7-tetrahydropyrazolo[1,5-a]pyridine-2,5-dicarboxylate

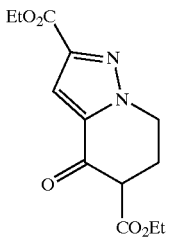

The pyrazole from preparation 7 (67.9 g, 0.208 mol) was azeotroped with toluene twice and then redissolved in fresh toluene (600 ml). Potassium tert-butoxide (25.0 g, 0.223 mol) was added, and the reaction stirred at room temperature for 15 minutes, and then heated under reflux for 1 ½ hours. The solution was left to stand overnight at room temperature and then diluted with hydrochloric acid (2M, 120 ml) and ethyl acetate (100 ml). The layers were separated, and the aqueous phase was extracted with ethyl acetate, the combined organic extracts were dried (Na$_2$SO$_4$), filtered and evaporated under reduced pressure, to give the title compound as a yellow solid, 65 g.

$^1$Hnmr (CDCl$_3$, 300 MHz) δ: 1.30–1.42 (6H, m), 2.90 (2H, t), 4.24–4.48 (6H, m), 7.15 (1H, s), 12.01 (1H, s).

Preparation 13

Diethyl 4-oxo-5,6,7,8-tetrahydro-4H-pyrazolo[1,5-a]azepine-2,5-dicarboxylate

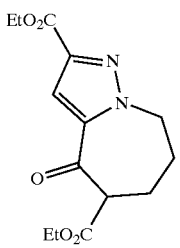

The title compound was obtained as an orange oil, in 93% yield, from the pyrazole of preparation 6, following the procedure of preparation 12.

¹Hnmr (CDCl₃, 400 MHz) δ: 1.28 (3H, t), 1.98 (2H, m), 2.16 (2H, m), 2.82 (2H, t), 4.38 (2H, q), 4.60 (2H, t), 7.31 (1H, s).

LRMS: m/z 223 (MH)⁺

Preparation 14

Methyl 3-nitro4-oxo-4,5,6,7-tetrahydropyrazolo[1,5-a]pyrazine-2-carboxylate

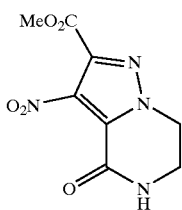

Trifluoroacetic acid (75 ml) was added to a solution of the pyrazole from preparation 11 (17.5 g, 47.0 mmol) in dichloromethane (75 ml), and the reaction stirred at room temperature for 2 hours. The solution was evaporated under reduced pressure, and the residual oil triturated well with ether to give a white gum. This was dissolved in methanol (200 ml), and triethylamine (26 ml, 192 mmol) added, while stirring the mixture vigorously. The resulting mixture was stirred for 30 minutes, the precipitate filtered off, washed with methanol, and dried to give the title compound, 6.5 g.

¹Hnmr (DMSOd₆, 400 MHz) δ: 3.68 (2H, m), 3.83 (3H, s), 4.43 (2H, t), 8.78 (1H, s).

Preparation 15

Methyl 5-ethyl-3-nitro-4-oxo-4,5,6,7-tetrahydropyrazolo[1,5-a]pyrazine-2-carboxylate

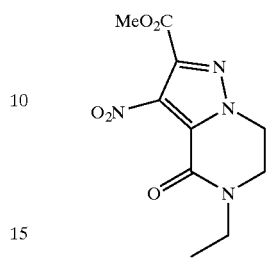

Sodium hydride (550 mg, 60% dispersion in mineral oil, 13.75 mmol) was added to a solution of the compound from preparation 14 (3.0 g, 12.5 mmol) in N,N-dimethylformamide (30 ml), and the solution stirred at room temperature for 1 hour. Ethyl iodide (1.2 ml, 15.0 mmol) was added, and the reaction stirred for a further hour. The reaction mixture was poured into 2% aqueous sodium bicarbonate solution (110 ml), and extracted with ether (100 ml) and ethyl acetate (70 ml). The combined organic extracts were dried (Na₂SO₄) and evaporated under reduced pressure. The residual yellow solid was purified by column chromatography on silica gel using ethyl acetate as eluant to give the title compound as a white solid, 2.09 g.

¹Hnmr (CDCl₃, 300 MHz) δ: 1.24 (3H, t), 3.61 (2H, q), 3.83 (2H, t), 3.96 (3H, s) 4.50 (2H, t).

Preparation 16

4-Oxo-4,5,6,7-tetrahydropyrazolo[1,5-a]pyridine-2-carboxylic Acid

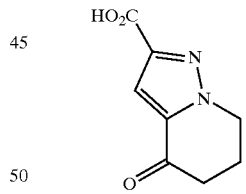

A mixture of the ethyl ester from preparation 12 (65 g, 0.232 mol) in concentrated hydrochloric acid (150 ml) and water (300 ml) was heated under reflux for 2 hours. The cooled mixture was evaporated under reduced pressure, and the residue azeotroped twice with a mixture of ethanol and toluene. The product was dried under vacuum to afford the title compound as a yellow solid. 52.3 g. which was used without further purification.

¹Hnmr (DMSOd₆, 300 MHz) δ: 2.27 (2H, m), 2.66 (2H, t), 4.40 (2H, t), 7.12 (1H, s).

LRMS m/z: 198 (MNH₄)⁺

Preparation 17

4-Oxo-5,6,7,8-tetrahydro-4H-pyrazolo[1,5-a]azepine-2-carboxylic Acid

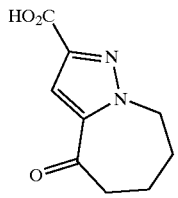

A mixture of the ethyl ester from preparation 13 (30.9 g, 0.105 mol) was heated under reflux in a mixture of water (200 ml) and concentrated hydrochloric acid (100 ml) for 5 hours under a nitrogen atmosphere. The cooled mixture was evaporated to dryness and azeotroped with a mixture of toluene and ethanol giving 22.6 g of product, which was used without further purification.

LRMS: m/z 195.2 (MH)$^+$

Preparation 18

Ethyl 4-oxo-4,5,6,7-tetrahydropyrazolo[1,5-a]pyridine-2-carboxylate

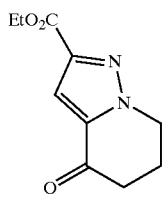

Concentrated sulphuric acid (30 ml) was added slowly to a solution of the crude acid from preparation 16 (52.3 g) in ethanol (400 ml), and the solution stirred under reflux for 2 hours. The cooled mixture was evaporated under reduced pressure to give an oil, which was poured onto ice and neutralised with sodium bicarbonate solution. This aqueous solution was extracted with dichloromethane (3×), and the combined organic extracts were dried (Na$_2$SO$_4$), filtered and evaporated under reduced pressure. The residual solid was triturated with ether (100 ml) filtered and dried to give the title compound as a white solid, 33.5 g.

$^1$Hnmr (CDCl$_3$, 300 MHz) δ: 1.40 (3H, t), 2.40 (2H, m), 2.76 (2H, m), 4.45 (4H, m), 7.38 (1H, s).

Preparation 19

Ethyl 4-oxo-5,6,7,8-tetrahydro-4H-pyrazolo[1,5-a]azepine-2-carboxylate

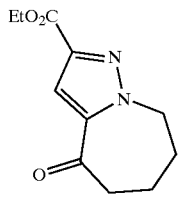

The title compound was obtained in 77% yield, from the acid from preparation 17, following a similar method to that described in preparation 18, except that, the product was isolated after column chromatography on silica gel, using ethyl acetate:pentane (75:25) as eluant.

$^1$Hnmr (CDCl$_3$, 300 MHz) δ: 1.40 (3H, t), 2.00 (2H, m), 2.15 (2H, m), 2.80 (2H, m), 4.40 (2H, q), 4.60 (2H, m), 7.30 (1H, s)

LRMS: m/z 223 (MH)$^+$

Preparation 20

Ethyl 4-methylene-4,5,6,7-tetrahydropyrazolo[1,5-a]pyridine-2-carboxylate

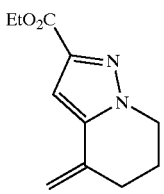

Potassium tert-butoxide (9.0 g, 0.08 mol) was added to a suspension of methyltriphenylphosphonium bromide (30.0 g, 0.084 mol) in toluene (500 ml) and the solution stirred for 10 minutes. The suspension was warmed gently for five minutes and then sonicated for 10 minutes before cooling in an ice-bath. The ketone from preparation 18 (15.60 g, 0.072 mol) was added and the resulting brown suspension was stirred at room temperature overnight. Water (300 ml) was added and the mixture extracted with ethyl acetate (200 ml). The organic extract was washed with water, dried (Na$_2$SO$_4$), filtered and evaporated under reduced pressure. The residual brown oil was purified by column chromatography on silica gel using an elution gradient of ethyl acetate: hexane (40:60 to 60:40), to afford the title compound as a colourless oil, 6.8 g.

$^1$Hnmr (CDCl$_3$, 400 MHz) δ: 1.39 (3H, t), 2.10 (2H, m), 2.58 (2H, m), 4.25 (2H, m), 4.40 (2H, q), 5.07 (1H, s), 5.50 (1H, s), 6.96 (1H, s).

LRMS: m/z 413 (2MH)$^+$

Preparation 21

Ethyl 4-methylene-5,6,7,8-tetrahydro-4H-pyrazolo[1,5-a]azepine-2-carboxylate

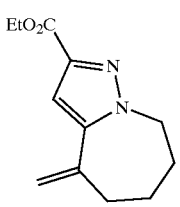

The title compound was obtained as a clear oil in 60% yield, from the ketone of preparation 19, following the procedure described in preparation 20.

$^1$Hnmr (CDCl$_3$, 400 MHz) δ: 1.39 (3H, t), 1.92 (4H, m), 2.45 (2H, m), 4.35 (2H, m), 4.39 (2H, q), 5.20 (1H, d), 5.28 (1H, d), 6.76 (1H, s).

LRMS m/z: 221 (MH)$^+$

Preparation 22

Ethyl 4-methyl-4,5,6,7-tetrahydropyrazolo[1,5-a]pyridine-2-carboxylate

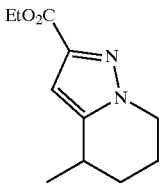

A mixture of the alkene from preparation 20 (6.8 g, 16.5 mmol) and 10% palladium on charcoal (1.80 g) in ethanol (200 ml) was hydrogenated at 60 psi and room temperature for 2½ hours. The reaction mixture was filtered through Arbocel®, washing the filter pad well with ethanol, and the filtrate evaporated under reduced pressure to afford the title compound, 6.2 g.

$^1$Hnmr (CDCl$_3$, 300 MHz) δ: 1.30 (3H, t), 1.38 (3H, t), 1.92–2.20 (4H, m), 2.92 (1H, m), 4.08 (1H, m), 4.25–4.42 (3H, m), 6.60 (1H, s).

LRMS: m/z 209.3 (MH)$^+$

Preparation 23

Ethyl 4-methyl-5,6,7,8-tetrahydro-4H-pyrazolo[1,5-a]azepine-2-carboxylate

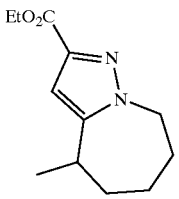

The title compound was obtained as an oil in quantitiative yield, from the alkene of preparation 21, following the procedure of preparation 22.

$^1$Hnmr (CDCl$_3$, 400 MHz) δ: 1.38 (6H, m), 1.58 (2H, m), 1.70 (1H, m), 1.83 (1H, m), 1.95 (1H, m), 2.07 (1H, m), 2.80 (1H, m), 4.10 (1H, dd), 4.29 (2H, q), 4.60 (1H, dd), 6.58 (1H, s).

LRMS: m/z 223 (MH)$^+$

Preparation 24

Ethyl 4-hydroxy-5,6,7,8-tetrahydro-4H-pyrazolo[1,5-a]azepine-2-carboxylate

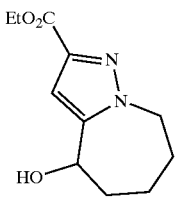

Sodium borohydride (285 mg, 7.44 mmol) was added to the ketone from preparation 19 (1.5 g, 6.76 mmol) in ethanol (75 ml) at 0° C. and the mixture stirred and left to warm to room temperature over 2 hours. The reaction mixture was evaporated to dryness and the residue partitioned between ethyl acetate and saturated sodium hydrogen carbonate solution. The layers were separated and the aqueous phase extracted with ethyl acetate (×2). The organic extracts were combined, dried (MgSO$_4$), filtered and evaporated under reduced pressure to afford the title compound as a clear oil, 1.48 g.

LRMS: m/z 225.2 (MH)$^+$

Preparation 25

Ethyl 7,8-dihydro-6H-pyrazolo[1,5-a]azepine-2-carboxylate

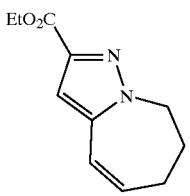

p-Toluenesulfonic acid (200 mg, 1.05 mmol) was added to the alcohol of preparation 24 (1.48 g, 6.6 mmol) in toluene (50 ml) and the mixture heated under reflux for 4 hours. Saturated sodium hydrogen carbonate solution was added and the layers separated. The aqueous phase was extracted with ethyl acetate (×2), the organic solutions combined, dried (MgSO$_4$), filtered and evaporated under reduced pressure to afford the crude title compound as a yellow oil, 1.4 g.

$^1$Hnmr (CDCl$_3$, 400 MHz) δ: 1.40 (3H, t), 2.10 (2H, m), 2.55 (2H, m), 4.40 (2H, q), 4.45 (2H, m), 5.95 (1H, m), 6.25 (1H, d), 6.65 (1H, s)

LRMS: m/z 207 (MH)$^+$

Preparation 26

Ethyl 5,6,7,8-tetrahydro-4H-pyrazolo[1,5-a]azepine-2-carboxylate

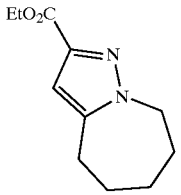

A mixture of the alkene from preparation 25 (1.4 g) and 10% palladium on charcoal (200 mg) in ethanol (50 ml) was hydrogenated for 17 hours at 60 psi and room temperature. The reaction mixture was filtered through Arbocel® and the catalyst washed thoroughly with methanol. The filtrate was evaporated under reduced pressure to yield the title compound as a clear oil 1.1 g.

$^1$Hnmr (CDCl$_3$, 300 MHz) δ: 1.40 (3H, t), 1.70 (2H, m), 1.80 (4H, m), 2.75 (2H, m). 4.35 (4H, m), 6.55 (1H, s)

LRMS: m/z 209.1 (MH)$^+$

Preparation 27

4-Methyl-5,6,7,8-tetrahydro-4H-pyrazolo[1,5-a]azepine-2-carboxylic Acid

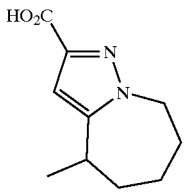

Sodium hydroxide (333 mg, 8.33 mmol) was added to a solution of the ester from preparation 23 (923 mg, 4.16 mmol) in water (5 ml) and dioxan (20 ml), and the solution stirred at room temperature for 72 hours. The solution was acidifed to pH 3, using hydrochloric acid, and the mixture was evaporated under reduced pressure, and the residue dried under vacuum. The product was used without further purification.

LRMS: m/z 195 (MH)$^+$

Preparation 28

3-Nitro-5,6-dihydro-4H-pyrrolo[1,2-b]pyrazole-2-carboxylic Acid

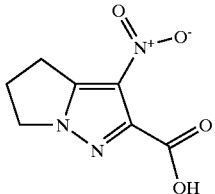

2N Sodium hydroxide (18 ml, 36 mmol) was added to a solution of the ester of preparation 3 (4.1 g, 22.8 mmol) in dioxan (70 ml) and the mixture stirred at 60° C. for 5 hours. The cooled reaction mixture was acidified with 2N hydrochloric acid (10 ml) and evaporated to dryness in vacuo.

Fuming nitric acid (4 ml) was added dropwise to ice-cooled concentrated sulphuric acid (25 ml) and the mixture heated to 40° C. The intermediate crude acid was added portionwise over 30 minutes maintaining the internal temperature below 55° C. The mixture was stirred at 50° C. for 4 hours, poured onto ice and stirred over 64 hours. The white precipitate was then filtered off and dried to afford 3.3 g of title compound.

$^1$Hnmr (CDCl$_3$, 300 MHz) δ: 2.70 (2H, m), 3.25 (2H, t), 4.25 (2H, t)

LRMS: m/z 220.1 (MNH$_4$)$^+$.

Preparation 29

3-Nitro-4,5,6,7-tetrahydropyrazolo[1,5-a]pyridine-2-carboxylic Acid

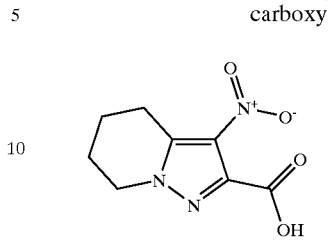

Sodium hydroxide solution (20 ml, 2M, 0.04 mol) was added to a solution of the ester from preparation 4 (5.8 g, 0.03 mol) in dioxan (100 ml), and the reaction stirred at room temperature overnight. The mixture was evaporated under reduced pressure, and hydrochloric acid (2M, 21 ml) was added. This mixture was evaporated under reduced pressure, the residue azeotroped with toluene, and the product dried under vacuum.

Fuming nitric acid (5 ml) was added to concentrated sulphuric acid (30 ml) with ice cooling. The resulting mixture was warmed to 40° C. and the intermediate acid was added portionwise over one hour so as to keep the internal temperature between 50 and 60° C. The reaction was stirred at 60° C. for 1 hour, followed by 4 hours at 50° C. and then stirred at room temperature overnight. The mixture was poured onto ice and the resulting precipitate filtered off, washed with water, and dried to afford the title compound, 4.6 g.

$^1$Hnmr (CDCl$_3$, 300 MHz) δ: 2.00 (2H, m), 2.15 (2H, m), 3.20 (2H, t), 4.28 (2H, t).

LRMS m/z: 229.3 (MNH$_4$)$^+$

Preparation 30

4-Methyl-3-nitro-4,5,6,7-tetrahydropyrazolo[1,5-a]ptridine-2-carboxylic Acid

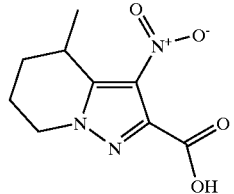

The title compound was obtained as a pale yellow solid, from the ester of preparation 22 in 74% yield, following the procedure described in preparation 29.

$^1$Hnmr (CDCl$_3$, 300 MHz) δ: 1.24 (3H, d), 1.68 (1H, m), 1.97 (2H, m), 2.07 (1H, m), 3.47 (1H, m), 4.01 (1H, m), 4.20 (1H, m).

Preparation 31

(5R)-5-Methyl-3-nitro-4,5,6,7-tetrahydropyrazolo[1,5-a]pyridine-2-carboxylic Acid

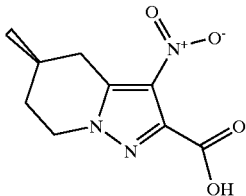

The title compound was obtained as a white solid in 83% yield, from the ester of preparation 5, following a similar procedure to that described in preparation 29.

LRMS: m/z 243 (MNH$_4$)$^+$

Preparation 32

3-Nitro-5,6,7,8-tetrahydro-4H-pyrazolo[1,5-a]azepine-2-carboxylic Acid

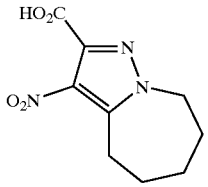

Sodium hydroxide pellets (423 mg, 10.6 mmol) were added to the ester of preparation 26 (1.1 g, 5.3 mmol) in a mixture of dioxan (20 ml) and water (5 ml), and the reaction was stirred at room temperature under nitrogen for 15 hours. Concentrated hydrochloric acid was added to neutralise the solution before evaporation under reduced pressure.

Fuming nitric acid (1.2 ml) was added to ice-cold concentrated sulphuric acid (8 ml) and the mixture heated to 40° C. for 10 minutes. The flask was then removed from the heat and the intermediate acid was added portionwise maintaining the internal temperature around 40° C. On complete addition the flask was immersed into an oil bath at 50° C. and heated for 4½ hours. The reaction mixture was poured onto ice, forming a green emulsion with a sticky solid residue, ether was added, dissolving the emulsion and solid, and the organic layer extracted. The aqueous phase was then further extracted with ether (x2). The organic extracts were combined and evaporated in vacuo to give a green/brown oil, 1.3 g. This was redissolved in dichloromethane, dried (MgSO$_4$), filtered and evaporated in vacuo to afford 990 mg of the title compound.

$^1$Hnmr (CDCl$_3$, 300 MHz) δ: 1.80 (4H, m), 1.95 (2H, m), 3.15 (2H, m), 4.45 (2H, m)

LRMS: m/z 243.2 (MNH$_4$)$^+$

Preparation 33

4-Methyl-3-nitro-5,6,7,8-tetrahydro-4H-pyrazolo[1,5-a]azepine-2-carboxylic Acid

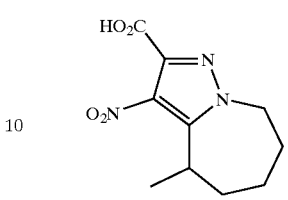

A mixture of fuming nitric acid (1.2 ml) and concentrated sulphuric acid (8 ml) was heated at 40° C. for 40 minutes, then stirred at room temperature for 5 hours. A solution of the acid from preparation 27 (895 mg, 4.59 mmol) in concentrated sulphuric acid (10 ml) was added portionwise, and once addition was complete, the reaction was heated at 50° C. for 24 hours, then stirred at room temperature for a further 72 hours. The mixture was poured onto ice, and this aqueous suspension extracted with ether (3x). The combined organic extracts were washed with water, brine, dried (MgSO$_4$) and evaporated under reduced pressure to give the title compound, 790 mg.

$^1$Hnmr (CDCl$_3$, 400 MHz) δ: 1.38 (3H, d), 1.62–1.81 (2H, m), 1.94–2.12 (4H, m), 4.02 (1H, m), 4.26 (1H, dd), 4.66 (1H, dd).

LRMS: m/z 257.7 (MNH$_4$)$^+$

Preparation 34

3-Nitro-4,5,6,7-tetrahydropyrazolo[1,5-a]pyridine-2-carboxamide

N,N-Dimethylformamide (0.1 ml) was added to an ice-cooled solution of the acid of preparation 29 (4.6 g, 22 mmol) in dichloromethane (100 ml), and oxalyl chloride (5.7 ml, 65 mmol) was added over 1 minute. The reaction was allowed to warm to room temperature over 2½ hours and the mixture then evaporated under reduced pressure, and dried under vacuum. The resulting solid was dissolved in tetrahydrofuran (100 ml) and cooled in an ice bath. Ammonia gas was bubbled through for 10 minutes and the reaction stirred at room temperature for one hour. The mixture was evaporated under reduced pressure and the resulting solid was treated with water (20 ml), washed with additional water (5 ml) and dried to give the title compound, as a beige solid, 4.2 g.

$^1$Hnmr (CDCl$_3$, 400 MHz) δ: 1.96 (2H, m), 2.10 (2H, m), 3.17 (2H, t), 4.21 (2H, m), 6.04 (1H, br s), 7.76 (1H, br s).

LRMS mz: 211.1 (MH)$^+$

Preparation 35

4-Methyl-3-nitro-4,5,6,7-tetrahydropyrazolo[1,5-a]pyridine-2-carboxamide

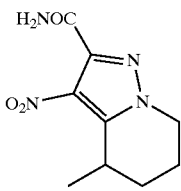

The title compound was obtained as a pink solid in 66% yield, from the compound of preparation 30, following the procedure described in preparation 34.

$^1$Hnmr (CDCl$_3$, 300 MHz) δ: 1.38 (3H, d), 1.83 (1H, m), 1.92–2.27 (3H, m), 3.68 (1H, m), 4.06 (1H, m), 4.36 (1H, m), 5.81 (1H, br s), 7.50 (1H, br s).

LRMS: m/z 225 (MH)$^+$

Preparation 36

(5R)-5-Methyl-3-nitro-4,5,6,7-tetrahydropyrazolo[1,5-a]pyridine-2-carboxamide

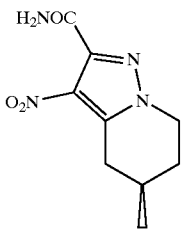

The title compound was obtained as a white solid in 67% yield, from the compound of preparation 31, following a similar procedure to that described in preparation 34.

$^1$Hnmr (DMSOd$_6$, 300 MHz) δ: 1.10 (3H, d), 1.72 (1H, m), 2.00 (2H, m), 2.58 (1H, m), 3.24 (1H, m), 4.05 (1H, m), 4.20 (1H, m), 7.65 (1H, br s), 7.94 (1H, br s).

LRMS: m/z 225 (MH)$^+$

Preparation 37

3-Nitro-5,6,7,8-tetrahydro-4H-pyrazolo[1,5-a]azepine-2-carboxamide

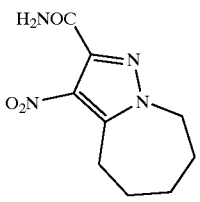

The product from preparation 32 (990 mg, 4.4 mmol) was dissolved in dichloromethane (30 ml) and N,N-dimethylformamide (1 drop) was added. Oxalyl chloride (1.15 ml, 13.2 mmol) was then added slowly and the mixture left to stir at room temperature for 66 hours. The reaction mixture was evaporated to dryness, azeotroped with toluene, redissolved in tetrahydrofuran (30 ml) and cooled to 0° C. Ammonia was bubbled through the solution of acid chloride for 20 minutes causing a brown precipitate to form. The flask was stoppered and left to warm to room temperature over 1½ hours. The mixture was then evaporated under reduced pressure and triturated with water to give a beige solid. This was washed with ether and dried to afford 620 mg of the title compound.

$^1$Hnmr (CDCl$_3$, 400 MHz) δ: 1.80 (4H, m), 1.90 (2H, m), 3.20 (2H, m), 4.40 (2H, m), 5.85 (1H, s), 7.15 (1H, s)

LRMS: m/z 225.2 (MH)$^+$

Preparation 38

4-Methyl-3-nitro-5,6,7,8-tetrahydro-4H-pyrazolo[1,5-a]azepine-2-carboxamide

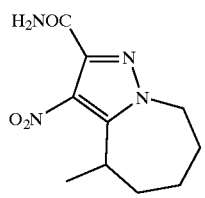

The title compound was obtained as a solid in 69% yield, from the acid of preparation 33, following the procedure of preparation 37.

$^1$Hnmr (CDCl$_3$, 300 MHz) δ: 1.38 (3H, d), 154 (2H, m), 1.60–1.80 (1H, m), 1.88–2.10 (3H, m), 3.98 (1H, m), 4.21 (1H, m), 4.60 (1H, m), 5.62 (1H, brs), 6.99 (1H, br s).

LRMS m/z: 239 (MH)$^+$

Preparation 39

3-Nitro-4-oxo-4,5,6,7-tetrahydropyrazolo[1,5-a]pyrazine-2-carboxamide

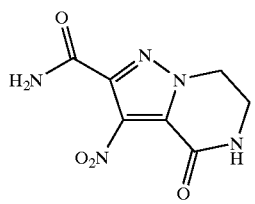

A solution of the ester from preparation 14 (500 mg, 2.1 mmol) in saturated ethanolic ammonia (10 ml) was heated at 100° C. in a sealed vessel for 16 hours. TLC analysis showed starting material remaining, so additional ethanolic ammonia (10 ml) was added, and the reaction heated at 120° C. in a sealed vessel for a further 24 hours. The mixture was cooled, the resulting precipitate filtered off, washed with ethanol, and dried to give the title compound as a white powder, 300 mg.

$^1$Hnmr (DMSOd$_6$, 300 MHz) δ: 3.68 (2H, m), 4.40 (2H, t), 7.72 (1H, s), 8.00 (1H, s), 8.74 (1H, s).

Preparation 40

Methyl 5-ethyl-3-nitro-4-oxo-4,5,6,7-tetrahydropyrazolo[1,5-a]pyrazine-2-carboxylate

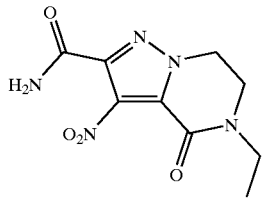

The title compound was obtained as a white solid (quantitatively), from the ester from preparation 15, following a similar procedure to that described in preparation 39.

¹Hnmr (DMSOd₆, 300 MHz) δ: 1.12 (3H, t), 3.44 (2H, q), 3.86 (2H, t), 4.46 (2H, t), 7.73 (1H, s), 7.99 (1H, s).

Preparation 41

3-Amino-5,6-dihydro-4H-pyrolo[1,2-b]pyrazole-2-carboxamide

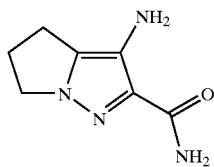

Oxalyl chloride (4.3 ml, 50 mmol) was added dropwise over 5 minutes, to an ice-cold solution of the acid from preparation 28 (3.25 g, 16.5 mol) and N,N-dimethylformamide (100 µl) in dichloromethane (50 ml), the solution stirred at 0° C. for 1 hour, then allowed to warm to room temperature. The solution was concentrated under reduced pressure, re-dissolved in tetrahydrofuran (50 ml), the solution cooled in ice, ammonia gas bubbled through for 5 minutes, and the solution stirred at room temperature overnight. The reaction mixture was evaporated under reduced pressure, the residue triturated with water (15 ml), and the resulting solid filtered and dried.

A mixture of this intermediate (2.95 g) was hydrogenated for 5 hours at 60 psi and room temperature in ethanol (100 ml) using 10% palladium on carbon (300 mg). The solution was warmed to 50° C., methanol (50 ml) and water (100 ml) were added and the solution filtered through Arbocel®. The filter pad was washed through with a hot methanol : water solution (4:1) and the filtrates combined and evaporated in vacuo to afford the title compound as a green solid, 2.0 g.

¹Hnmr (DMSOd₆, 300 MHz) δ: 2.44 (2H, m), 2.66 (2H, t), 3.97 (2H, t), 4.52 (2H, br s), 6.82 (1H, br s), 7.02 (1H, br s).

LRMS: m/z 167 (MH)⁺

Preparation 42

3-Amino-4,5,6,7-tetrahydropyrazolo[1,5-a]pyridine-2-carboxamide

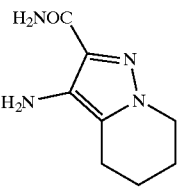

A mixture of the nitro compound from preparation 34 (4.2 g, 20 mmol) and 10% palladium on charcoal (0.5 g) in methanol (200 ml) was hydrogenated at 60 psi and room temperature for 5 hours. The mixture was diluted with methanol (200 ml) with warming, in order to dissolve the residual solid, then filtered through Arbocel®. The filtrate was evaporated under reduced pressure to afford the title compound as a brown solid, 3.15 g.

¹Hnmr (DMSOd₆, 400 MHz) δ: 1.75 (2H, m), 1.90 (2H, m), 2.55 (2H, t), 3.96 (2H, t), 4.40 (2H, br s), 6.86 (1H, br s), 7.04 (1H, br s).

LRMS m/z: 181.5 (MH)⁺

Preparation 43

3-Amino-4-methyl-4,5,6,7-tetrahydropyrrolo[1,5-a]pyridine-2-carboxamide

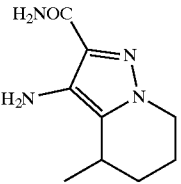

A mixture of the nitro compound from preparation 35 (3.50 g, 15.0 mmol) and 10% palladium on charcoal (500 mg) in ethanol (70 ml) was hydrogenated at 60 psi and 60° C. for 18 hours. The cooled mixture was filtered through Arbocel® and the filter pad washed well with a hot mixture of 10% water in methanol. The filtrate was evaporated under reduced pressure to afford the title compound, as a beige solid, 3.0 g.

¹Hnmr (CDCl₃, 400 MHz) δ: 1.30 (3H, d), 1.60 (1H, m), 1.97 (2H, m), 2.10 (1H, m), 3.00 (1H, m), 4.01 (4H, m), 5.19 (1H, br s), 6.55 (1H, br s).

LRMS: m/z 195 (MH)⁺

Preparation 44

3-Amino-(5R)-5-methyl-4,5,6,7-tetrahydropyrazolo[1,5-a]pyridine-2-carboxamide

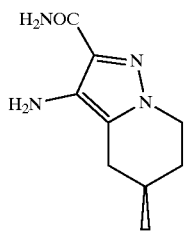

The title compound was obtained as a solid in 67% yield after recrystallisation from ethanol, from the the nitro compound from preparation 36, and following the procedure described in preparation 43.

LRMS: m/z 195 (MH)$^+$

Preparation 45

3-Amino-5,6,7,8-tetrahydro-4H-pyrazolo[1,5-a]azepine-2-carboxamide

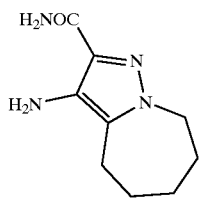

The title compound was obtained as a beige solid, in 66% yield from the nitro compound of preparation 37, following a similar procedure to that described in preparation 43, except, the crude product was additionally purified by column chromatography using an eluant of dichloromethane:methanol (90:10).

$^1$Hnmr (CDCl$_3$, 300 MHz) δ: 1.60 (2H, m), 1.80 (4H, m), 2.60 (2H, m), 4.20 (2H, m), 5.25 (1H, s), 6.60 (1H, s)

LRMS: m/z 195 (MH)$^+$

Preparation 46

3-Amino-4-methyl-4,5,6,7-tetrahydro-4H-pyrazolo[1,5-a]azepine-2-carboxamide

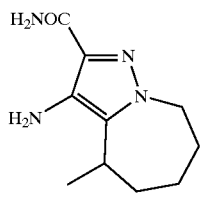

The title compound was obtained as a brown gum in 50% yield, from the nitro compound from preparation 38, following a similar procedure to that described in preparation 43.

$^1$Hnmr (CDCl$_3$, 400 MHz) δ: 1.30 (3H, d), 1.66 (2H, m), 1.85 (4H, m), 3.12 (1H, m), 4.14 (1H, m), 4.28 (1H, m), 5.26 (1H, brs), 6.56 (1H, brs).

LRMS: m/z 209 (MH)$^+$

Preparation 47

3-Amino-5-ethyl-4-oxo-4,5,6,7-tetrahydropyrazolo[1,5-a]pyrazine-2-carboxamide

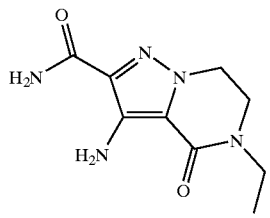

A mixture of the nitro compound from preparation 40 (690 mg, 2.7 mmol) and 10% palladium on charcoal (70 mg) in methanol (10 ml) was hydrogenated at 60 psi and 50° C. for 2 hours. The cooled mixture was filtered through Arbocel®, washing through with methanol, and the filtrate evaporated under reduced pressure to afford the title compound as a white solid, 600 mg.

$^1$Hnmr (DMSOd$_6$, 300 MHz) δ: 1.08 (3H, t), 3.42 (2H, q), 3.70 (2H, t), 4.23 (2H, t), 5.21 (2H, s), 7.10 (1H, s), 7.30 (1H, s).

Preparation 48

2-Hydroxy-5-sulfonicotinic Acid

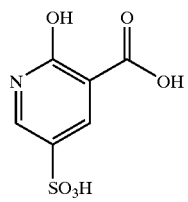

2-Hydroxynicotinic acid (27 Kg, 194.2 mol) was added portionwise to 30% oleum (58.1 Kg) at 50° C. over 1 hour. This caused an exotherm to 82° C. The reaction mixture was heated further to 140° C. After maintaining this temperature for 12 hours the reactor contents were cooled to 15° C. and filtered. The filter cake was then re-slurried with acetone (33 Kg) at room temperature, filtered and dried to afford the title compound, 35.3 Kg, as a white solid.

Decomposition pt 273° C.

$^1$Hnmr (DMSOd$_6$, 300 MHz) δ: 7.93 (1H, d), 8.42 (1H, d).

LRMS: m/z 220 (MH)$^+$

Preparation 49

Ethyl 2-Hydroxy-5-sulfonicotinoate

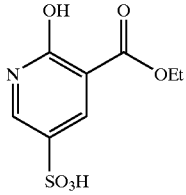

The acid from preparation 48 (500 g, 2.28 mol) was dissolved in ethanol (2.5 L) with stirring and heated to 80° C. After 30 minutes 0.5 L of solvent was distilled off, then replaced with fresh ethanol (0.5 L) and taken back to 80° C. After a further 60 minutes 1.0 L of solvent was distilled off, then replaced with fresh ethanol (1.0 L) and taken back to 80° C. After a further 60 minutes 1.0 L of solvent was distilled off, the reaction cooled to 22° C. and stirred for 16 hours. The precipitated product was filtered, washed with ethanol (0.5 L) and dried at 50° C. under vacuum to afford the title compound, 416 g, as a white solid.

Decomposition pt 237° C.

$^1$Hnmr (DMSOd$_6$, 300 MHz) δ: 1.25 (3H, t), 4.19 (2H, q), 7.66 (1H, d), 8.13 (1H, d).

LRMS: m/z 248 (MH)$^+$

Preparation 50

Ethyl 2-chloro-5-sulfonicotinoate

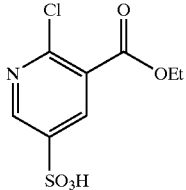

The ester from preparation 49 (24.7 g, 0.1 mol) was slurried in thionyl chloride (238 g, 2.0 mol) and N,N-dimethylformamide (1.0 mL) with stirring. The reaction mixture was then heated under reflux for 2.5 hours. The bulk of the thionyl chloride was removed under vacuum with residual thionyl chloride removed with a toluene azeotrope to afford the crude title compound (30.7 g, 108%) as a yellow oil. This was used without further purification.

$^1$Hnmr (CDCl$_3$, 300 MHz) δ: 1.46 (3H, t), 4.50 (2H, q), 8.72 (1H, d), 9.09 (1H, d).

Preparation 51

Ethyl 2-chloro-5-(4-ethyl-1-piperazinylsulfonyl)nicotinoate

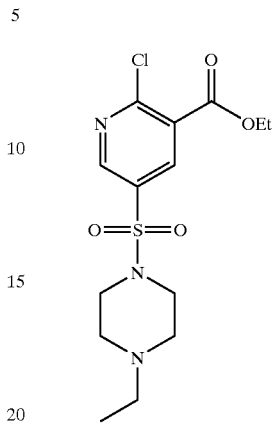

The sulphonic acid from preparation 50 (30.7 g, 0.1 mol) was dissolved in ethyl acetate (150 mL) with stirring then ice cooled. To this was added a solution of N-ethylpiperazine (11.4 g, 0.1 mol) and triethylamine (22.5 g, 0.22 mol) in ethyl acetate (50 mL), carefully over 30 minutes, keeping the internal temperature below 10° C. Once the addition was complete the reaction was allowed to warm to 22° C. and stirred for 1 hour. The solid was filtered off and the remaining filtrate was concentrated under vacuum to afford the title compound, 37.1 g, as a yellow gum.

$^1$Hnmr (CDCl$_3$, 300 MHz) δ: 1.10 (3H, t), 1.42 (3H, m), 2.50 (2H, m), 2.60 (4H, m), 3.19 (4H, m), 4.43 (2H, q), 8.40 (1H, d), 8.80 (1H, d).

LRMS: m/z 362 (MH)$^+$

Preparation 52

Ethyl 2-ethoxy-5-(4-ethyl-1-piperazinylsulfonyl)nicotinoate

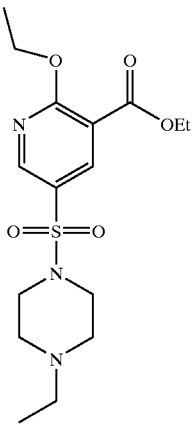

A solution of the chloride from preparation 51 (36.1 g, 0.1 mol) in ethanol (180 mL) was cooled to 10° C. with stirring.

Sodium ethoxide (10.2 g, 0.15 mol) was added portionwise keeping the temperature below 20° C. The reaction mixture was then stirred at ambient temperature for 18 hours. The precipitate was filtered off and water (180 mL) added to the filtrate. The filtrate was then heated to 40° C. for 1 hour. Ethanol (180 mL) was then distilled off at ambient pressure and the remaining aqueous solution allowed to cool to ambient temperature. The precipitated product was then filtered off, washed with water and dried under vacuo at 50° C. to afford the title compound, 12.6 g, as a light brown solid.

M.p. 66–68° C.

$^1$Hnmr (CDCl$_3$, 300 MHz) δ: 1.04 (3H, t), 1.39 (3H, t), 1.45 (3H, t), 2.41 (2H, q), 2.52 (4H, m), 3.08 (4H, m), 4.38 (2H, q), 2.57 (2H, q), 8.38 (1H, d), 8.61 (1H, LRMS: m/z 372 (MH)$^+$ Preparation 53

2-Ethoxy-5-(4-ethyl-1-piperazinylsulfonyl)nicotinic Acid

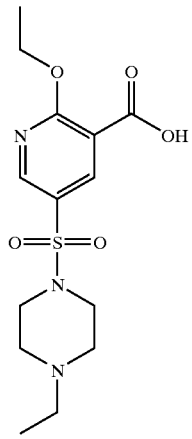

The ethyl ester from preparation 52 (10.2 g, 0.0275 mol) was dissolved in toluene (50 mL) and a solution of sodium hydroxide (1.1 g, 0.0275 mol) in water (20 mL) added to it. This two phase mixture was then stirred vigorously at ambient temperature overnight. The aqueous phase was separated off and adjusted to pH 5.6 by addition of concentrated hydrochloric acid. The precipitated product was slurried with ice cooling for 15 minutes, filtered, water washed and dried under vacuo at 50° C. to afford the title compound, 4.1 g, as an off-white solid.

Mpt 206–207° C.

$^1$Hnmr (CDCl$_3$, 300 MHz) δ: 1.25 (3H, t), 1.39 (3H, t), 2.82 (2H, q), 3.03 (4H, m), 3.25 (4H, m), 4.50 (2H, q), 8.25 (1H, d), 8.56 (1H, d).

LRMS: m/z 344 (MH)$^+$

Alternative Method

The compound from preparation 49 (441.5 g, 1.79 mol) was dissolved in toluene (1.77 L) and thionyl chloride (1.06Kg, 8.93 mol) and N,N-dimethylformamide (71.3 mL) were then added. The stirred suspension was then heated to reflux for 3 hours to yield a yellow solution. Thionyl chloride (2.87 L) was then distilled with continual replacement with toluene (2.15 L). The cooled pale yellow solution was then cooled to 10° C. and a stirred solution of N-ethylpiperazine (198.9 g, 1.66 mol) and triethylamine (392.2 g, 3.88 mol) in toluene (700 mL) was added dropwise over 90 minutes keeping the reaction mixture below 10° C. with external cooling. The reaction was stirred at ambient temperature for 18 hours then washed with water (2×700 mL) and brine (2×350 mL). The toluene phase was azeotropically dried by distilling off 1750 mL which was continuously replaced by dry toluene (1750 mL). The remaining brown solution was cooled to 10° C. and sodium ethoxide (178.0 g, 2.616 mol) was added portionwise keeping the temperature below 10° C. The reaction was then stirred at 10° C. for 1 hour then allowed to warm to ambient temperature and stirred for 18 hours. Sodium hydroxide (34.9 g, 0.873 mol) dissolved in water (1.5 L) was then added to the toluene mixture and the 2 phase mixture was vigorously stirred for 18 hours at 40° C. Once cooled to ambient temperature the aqueous phase was separated off. To this was added concentrated hydrochloric acid to pH 3 which precipitated a light brown solid which was granulated for 2 hour with ice cooling. The precipitate was filtered washed with water (300 mL) and dried under vacuo at 50° C. to afford the title compound, 338.4 g, as an off-white solid.

Preparation 54

2-Ethyl-5-(4-ethyl-1-piperazinylsulfonyl)nicotinic Acid Chloride Hydrochloride

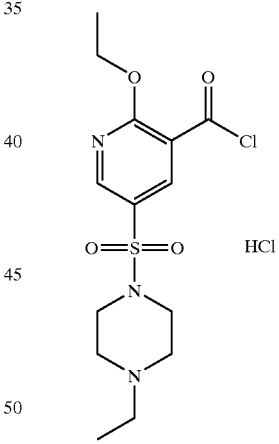

Oxalyl chloride (0.77 ml, 8.85 mmol) was added dropwise to a stirred, ice-cooled solution of the acid from preparation 53 (1.52 g, 4.42 mmol) and N,N-dimethylformamide (2 drops) in dichloromethane (30 ml), and the reaction mixture stirred for 18 hours at room temperature, then evaporated under reduced pressure. The residue was triturated with ethyl acetate and the resulting solid collected, washed with ether and dried under suction to afford the title compound, 1.68 g.

$^1$Hnmr (CDCl$_3$, 300 MHz) δ: 1.46 (6H, m), 2.95 (2H, q), 3.11 (2H, m), 3.48 (2H, m), 3.55 (2H, m), 3.92 (2H, m), 4.60 (2H, q), 8.58 (1H, s), 13.16 (1H, s).

Preparation 55

3-[({2-Ethoxy-5-[(4-ethyl-1-piperazinyl)sulfonyl]-3-pyridinyl}carbonyl)amino]-5,6-dihydro-4H-pyrrolo[1,2-b]pyrazole-2-carboxamide

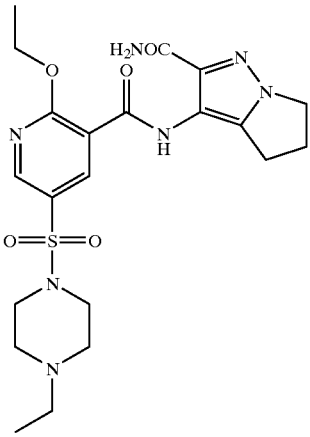

The acid from preparation 53 (4.94 g, 13 mmol) was suspended in a mixture of dichloromethane (100 ml) and N,N-dimethylformamide (0.25 ml) and cooled in ice. Oxalyl chloride (4.4 ml, 50 mmol) was added over 5 minutes, and the reaction stirred whilst reaching room temperature over 4 hours. The solution was evaporated to dryness in vacuo and azeotroped with toluene to give a white solid. This was dissolved in dichloromethane (100ml) and the amine from preparation 41 (2.0 g, 12 mmol) and triethylamine (5 ml, 36 mmol) were added, causing an exotherm. The mixture was stirred at room temperature for 16 hours. Sodium hydrogen carbonate solution was added and the organic phase removed and washed with water. The organic extract was dried ($Na_2SO_4$), filtered and evaporated in vacuo. The residue was purified by column chromatography on silica gel using an eluant of dichloromethane:methanol (100:0 to 95:5) to afford the title compound as a beige solid, 4.3 g $^1$Hnmr (CDCl$_3$, 400 MHz) δ: 1.00 (3H, t), 1.55 (3H, t), 2.40 (2H, q), 2.55 (4H, m), 2.60 (2H, m), 3.10 (4H, m), 3.45 (2H, t), 4.15 (2H, t), 4.80 (2H, q), 5.40 (1H, br s), 6.65 (1H, br s), 8.60 (1H, s), 8.80 (1H, s), 11.30 (1H, s)

LRMS: m/z 492.6 (MH)$^+$

Preparations 56 to 60

The following compounds of the general structure:

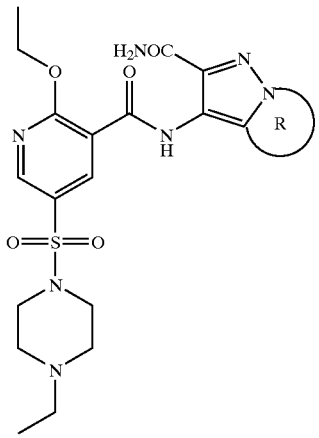

were prepared from the acid of preparation 53 and the appropriate amine, following similar methods to that described in preparation 55.

| Prep. No | R | Yield (%) | Data |
|---|---|---|---|
| 56 | cyclohexyl | 91 | $^1$Hnmr(CDCl$_3$, 300 MHz) δ: 1.01(3H, t), 1.58(3H, t), 1.90(2H, m), 2.27(2H, m), 2.39(2H, q), 2.53(4H, m), 3.00(2H, t), 3.10(4H, m), 4.17(2H, t), 4.79(2H, q), 5.30(1H, br s), 6.63(1H, br s), 8.62(1H, s), 8.81(1H, s), 10.74(1H, s). LRMS: m/z 506.9(MH)$^+$ |
| 57[1] | 2-methylcyclohexyl | 92 | $^1$Hnmr(CDCl$_3$, 300 MHz) δ: 1.01(3H, t), 1.10(3H, t), 1.58(4H, m), 1.98–2.18(3H, m), 2.40(2H, q), 2.55(4H, m), 3.10(4H, m), 3.63(1H, m), 4.14(2H, t), 4.80(2H, q), 5.26(1H, br s), 6.64(1H, br s), 8.65(1H, s), 8.83(1H, s), 10.72(1H, s). |
| 58 | 4-methylcyclohexyl | 74 | $^1$Hnmr(CDCl$_3$, 300 MHz) δ: 1.02(3H, t), 1.18(3H, d), 1.58(3H, t), 1.80(1H, m), 2.04(2H, m), 2.40(2H, q), 2.50–2.65(5H, m), 3.14(5H, m), 4.08(1H, m), 4.28(1H, m), 4.79(2H, q), 5.28(1H, br s), 6.65(1H, br s), 8.64(1H, d), 8.84(1H, d), 10.72(1H, s). |
| 59[1] | cycloheptyl | 47 | $^1$Hnmr(CDCl$_3$, 300 MHz) δ: 1.05(3H, t), 1.45(3H, t), 1.60(2H, m), 1.85(4H, m), 2.40(2H, m), 2.55(4H, s), 2.85(2H, m), 3.10(4H, m), 4.15(2H, m), 4.80(2H, q), 5.25(1H, s), 6.65 (1H, s), 8.65(1H, s), 8.85(1H, s), 10.50(1H, s) LRMS: m/z 520(MH)$^+$, |
| 60 | 4-methylcycloheptyl | | $^1$Hnmr(CDCl$_3$, 300 MHz) δ: 1.01(3H, t), 1.40(3H, d), 1.59(4H, m), 1.80(1H, m), 1.88–2.06(4H, m), 2.40(2H, q), 2.55(4H, m), 3.10(4H, m), 3.50(1H, m), 4.24(1H, m), 4.42 (1H, m), 4.78(2H, q), 5.22(1H, br s), 6.60(1H, br s), 8.63(1H, d), 8.83(1H, d), 10.34(1H, s). |

[1]= isolated after ether trituration, and not column chromatography.

Preparation 61

3-[({2-Ethoxy-5-[(4-ethyl-1-piperazinyl)sulfonyl]-3-pyridinyl}carbonyl)amino]-4-oxo-4,5,6,7-tetrahydropyrazolo[1,5-a]pyrazine-2-carboxamide

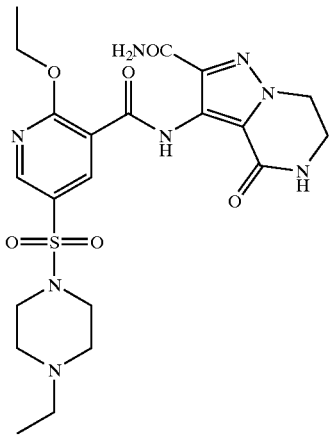

A mixture of the nitro compound from preparation 39 (300 mg, 1.33 mmol) and 10% palladium on charcoal (30 mg) in methanol (10 ml) was hydrogenated at 50° C. and 60 psi for 20 hours. The cooled mixture was concentrated under reduced pressure and azeotroped well with dichloromethane. This solid was suspended in pyrazole (12 ml), the acid chloride from preparation 54 (612 mg, 1.56 mmol) added, and the reaction stirred at 60° C. for 23 hours. The reaction mixture was evaporated under reduced pressure, and the residue partitioned between ethyl acetate (20 ml) and saturated aqueous sodium bicarbonate solution (20 ml). The aqueous phase was extracted with ethyl acetate (2×20 ml), and the combined organic solutions combined and allowed to concentrate to about 20 ml. The resulting crystalline product was filtered off, re-dissolved in warm methanol, and this solution filtered through Arbocel®. The filtrate was evaporated under reduced pressure to afford the title compound, 300 mg.

$^1$Hnmr (CDCl$_3$, 300 MHz) δ: 1.01 (3H, t), 1.59 (3H, t), 2.39 (2H, q), 2.51 (4H, m), 3.07 (4H, m), 3.84 (2H, m), 4.40 (2H, t), 4.78 (2H, q), 5.43 (1H, br s), 6.01 (1H, s), 6.70 (1H, br s), 8.65 (1H, s), 8.92 (1H, s), 10.80 (1H, s).

Preparation 62

3-[({2-Ethoxy-5-[(4-ethyl-1-piperazinyl)sulfonyl]-3-pyridinyl}carbonyl)amino]-5-ethyl-4-oxo-4,5,6,7-tetrahydropyrazolo[1,5-a]azepine-2-carboxamide

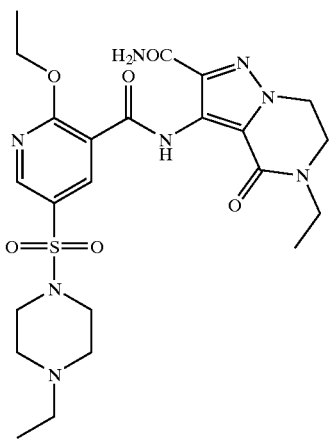

A mixture of the acid chloride from preparation 54 (910 mg, 2.32 mmol) and the amine from preparation 47 (470 mg, 2.11 mmol) in pyrazole (17 ml) was heated at 80° C. for 3 days. The cooled mixture was concentrated under reduced pressure and azeotroped with toluene. The residue was partitioned between 3% aqueous sodium bicarbonate solution and ethyl acetate, and the layers separated. The aqueous phase was extracted with ethyl acetate, the combined organic solutions dried (Na$_2$SO$_4$), and evaporated under reduced pressure. The oily residue was purified by column chromatography on silica gel using an elution gradient of dichloromethane:methanol (95:5 to 90:10) to afford the title compound, 750 mg.

$^1$Hnmr (CDCl$_3$, 300 MHz) δ: 1.01 (3H, t), 1.24 (3H, t), 1.59 (3H, t), 2.39 (2H, q), 2.50 (4H, m), 3.10 (4H, m), 3.63 (2H, q), 3.81 (2H, t), 4.38 (2H, t), 4.78 (2H, q), 5.41 (1H, br s), 6.71 (1H, br s), 8.64 (1H, d), 8.92 (1H, d), 10.68 (1H, s).

Preparation 63

5-Acetyl-2-ethoxynicotinic Acid

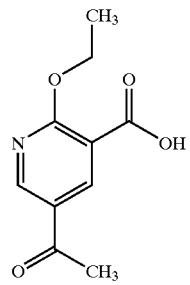

Triethylamine (354 ml, 2.54 mol), was added to a slurry of 5-bromo-2-ethoxynicotinic acid (250 g, 1.02 mol) in acetonitrile (1 L). To this reaction mixture was added palladium (II) acetate (4.56 g, 20.3 mmol), butyl vinyl ether (305 g, 3.05 mol) and tri-o-tolyl phosphine (12.4 g, 40.6 mmol), each addition being washed in with acetonitrile. Further acetonitrile (1 L) was then added and the reaction mixture heated to reflux under nitrogen for 22 hours. The reaction mixture was left at room temperature for 16 hours, and then the precipitate removed by filtration. The filtrate was concentrated in vacuo to give a brown gum, which was then stirred for 1 hour in water (1 L) and concentrated HCl (1 L). The reaction mixture was diluted with water (6.25 L), and extracted with dichloromethane (6×500 mL). The combined organic layers were extracted with 5% sodium bicarbonate solution (1.2 L, 2×400 ml). The basic aqueous extracts were washed with dichloromethane (250 ml), and then acidified to pH 3. After stirring for 30 minutes the precipitated product was removed by filtration, washed with water (250 ml) and dried at 50° C. in vacuo to yield the target compound as a white solid (134 g, 64.1 mmol, 63%).

$^1$H NMR (CDCl$_3$) δ: 1.56 (t, 3H), 2.64 (s, 3H), 4.78 (q, 2H), 8.96 (d, 1H), 8.98 (d, 1H).

LRMS: m/z (ES$^-$) 208 [M-H$^-$]

Preparation 64

3-{[(5-Acetyl-2-ethoxy-3-pyridinyl)amino}-4-methyl-4,5,6,7-tetrahydropyrazolo[1,5-a]pyridine-2-carboxamide

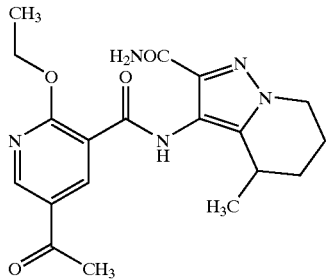

A mixture of the acid from preparation 63 (600 mg, 2.9 mmol) and O-(7-azabenzotriazol-1-yl)-N,N,N',N'-tetramethyluronium hexafluorophosphate (1.14 g, 3.0 mmol) in dichloromethane (10 ml) was added to a suspension of the pyrazole from preparation 43 (557 mg, 2.9 mmol), and N,N-diisopropylethylamine (2.5 ml, 14.3 mmol) in N,N-dimethylformamide (1 ml) and dichloromethane (10 ml), and the reaction mixture stirred at room temperature for 20 hours. The mixture was concentrated under reduced pressure, and the brown residue suspended in ethyl acetate (50 ml). The resulting precipitate was filtered off, and washed with diethyl ether. The solid was partitioned between dichloromethane (50 ml) and saturated sodium bicarbonate solution (25 ml), and the layers separated. The aqueous phase was further extracted with dichloromethane (3×25 ml), and the combined organic solutions were washed with 2N hydrochloric acid (25 ml), brine (25 ml), dried (MgSO$_4$) and evaporated under reduced pressure. The resulting solid was recrystallised from ethyl acetate to afford the title compound as a white solid, 570 mg.

$^1$H NMR (CDCl$_3$) δ: 1.04 (d, 3H), 1.55 (m, 4H), 1.97–2.14 (m, 3H), 2.59 (s, 3H), 3.60 (m,1H), 4.08 (m, 2H), 4.78 (q, 2H), 5.26 (bs,1 H), 6.62 (bs, 1H), 8.84 (s, 1H), 9.00 (d, 1H), 10.65 (s, 1H).

LRMS: m/z (TSP$^+$) 386.2 [MH$^+$]

EXAMPLES

Example 1

2-{2-Ethoxy-5-[(4-ethyl-1-piperazinyl)sulphonyl]-3-pyridinyl}-3,7,8,9-tetrahydro-4H-pyrrolo[2',1':5,1]pyrazolo[4,3-d]pyrimidin-4-one

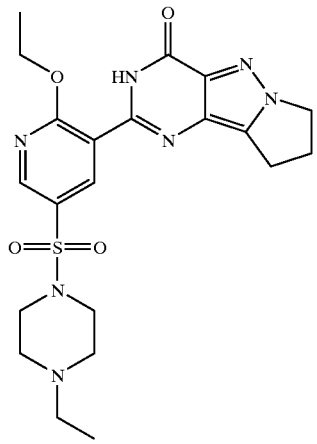

Potassium bis(trimethylsilyl)amide (7.5 g, 37.5 mmol) was added to a solution of the product from preparation 55 (4.3 g, 8.7 mmol) in ethanol (200 ml) and the reaction mixture heated in a sealed vessel at 130° C. for 16 hours. The cooled reaction mixture was evaporated under reduced pressure, and the residue partitioned between dichloromethane and water. Solid carbon dioxide was added to neutralise the solution causing a thick precipitate to form. The precipitate was filtered through Celite®, washing through with dichloromethane. The combined filtrates were dried (Na$_2$SO$_4$), filtered and evaporated under reduced pressure. The crude product was purified by column chromatography on silica gel, using an elution gradient of dichloromethane: methanol (99:1 to 92:8) to afford 180 mg of title product.

$^1$Hnmr (CDCl$_3$, 400 MHz) δ: 1.00 (3H, t), 1.60 (3H, t), 2.40 (2H, q), 2.55 (4H, m), 2.80 (2H, m), 3.10 (4H, m), 3.25 (2H, m), 4.40 (2H, t), 4.75 (2H, q), 8.60 (1H, s), 9.05 (1H, s) 10.70 (1H, s).

LRMS: m/z 474.7 (MH)$^+$

Found: C, 52.28; H, 5.71; N, 20.36. C$_{21}$H$_{27}$N$_7$O$_4$S; 0.5H$_2$O requires C, 52.26; H, 5.85, N, 20.32%.

Example 2

2-{2-Ethoxy-5-[(4-ethyl-1-piperazinyl)sulfonyl]-3-pyridinyl}-7,8,9,10-tetrahydropyrido[2',1':5,1]pyrazolo[4,3-d]pyrimidin-4(3H)-one

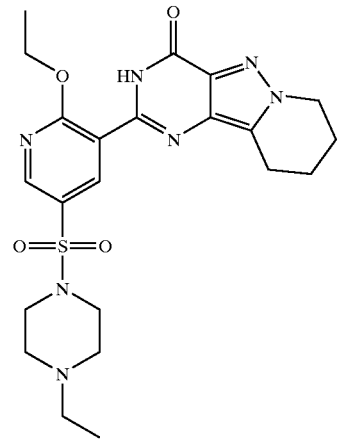

A mixture of the compound from preparation 56 (1.0 g, 1.98 mmol), ethyl acetate (100 μl, 1.0 mmol) and potassium bis(trimethylsilyl)amide (1.20 g, 6.0 mmol) in ethanol (80 ml) was heated in a sealed vessel at 130° C. for 18 hours. The cooled mixture was concentrated under reduced pressure and the residue partitioned between water and dichloromethane. The mixture was neutralised by the addition of solid carbon dioxide, the layers separated, and the aqueous phase extracted with dichloromethane (3×). The combined organic extracts were dried (Na$_2$SO$_4$), filtered and evaporated under reduced pressure. The crude product was purified by column chromatography on silica gel using an elution gradient of dichloromethane:methanol (98:2 to 94:6) to afford the title compound as a solid, 490 mg.

$^1$Hnmr (CDCl$_3$, 400 MHz) δ: 1.01 (3H, t), 1.57 (3H, t), 2.01 (2H, m), 2.18 (2H, m), 2.40 (2H, q), 2.55 (4H, m), 3.14 (6H, m), 4.40 (2H, m), 4.75 (2H, q), 8.61 (1H, s), 9.04 (1H, s), 10.66 (1H, s).

Found: C, 52.65; H, 6.02; N, 19.46. C$_{22}$H$_{29}$N$_7$O$_4$S;H$_2$O requires C, 52.25; H, 6.18; N, 19.39%.

Example 3

2-{2-Ethoxy-5-[(4-ethyl-1-piperazinyl)sulfonyl]-3-pyridinyl}-10-methyl-7,8,9,10-tetrahydropyrido[2',1':5,1]pyrazolo[4,3-d]pyrimidin-4(3H)-one

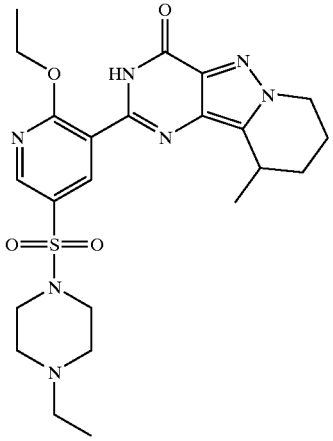

The title compound was obtained in 49% yield from the amide of preparation 57, following the procedure of example 2.

¹HNMR (CDCl₃, 300 MHz) δ: 1.02 (3H, t), 1.59 (7H, m), 2.02–2.28 (3H, m), 2.41 (2H, q), 2.57 (4H, m), 3.15 (4H, m), 3.38 (1H, m), 4.34 (1H, m), 4.43 (1H, m) 4.77 (2H, q), 8.62 (1H, d), 9.03 (1H, d), 10.65 (1H, s).

LRMS: m/z 502.2 (MH)⁺

Found: C, 54.44; H, 6.24; N, 19.32. $C_{23}H_{31}N_7O_4S;0.5H_2O$ requires C, 54.10; H, 6.31; N, 19.20%.

Example 4

(9R)-2-{2-Ethoxy-5-[(4-ethyl-1-piperazinyl)sulfonyl]-3-pyridinyl}-9-methyl-7,8,9,10-tetrahydropyrido[2',1':5,1]pyrazolo[4,3-d]pyrimidin-4(3H)-one

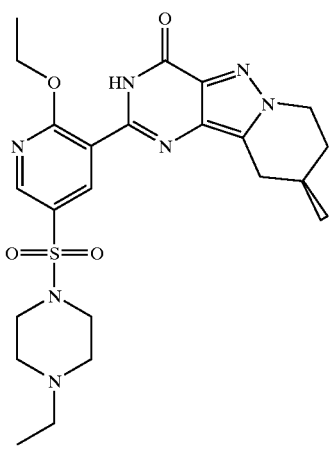

The title compound was obtained as a white solid in 52% yield after trituration with ether, from the amide of preparation 58, following the method of example 2.

¹HNMR (CDCl₃, 300 MHz) δ: 1.02 (3H, t), 1.25 (3H, d), 1.58 (3H, t), 1.90 (1H, m), 2.18 (2H, m), 2.41 (2H, q), 2.58 (4H, m), 2.63 (1H, m), 3.14 (4H, m), 3.38 (1H, m), 4.35 (1H, m), 4.58 (1H, m), 4.77 (2H, q), 8.62 (1H, d), 9.06 (1H, d), 10.78 (1H, s).

LRMS: m/z 502.5 (MH)⁺

Example 5

2-{2-Ethoxy-5-[(4-ethyl-1-piperazinyl)sulfonyl]-3-pyridinyl}-9-ethyl-8,9-dihydropyrazino[2',1':5,1]pyrazolo[4,3-d]pyrimidine-4,10(3H,7H)-dione

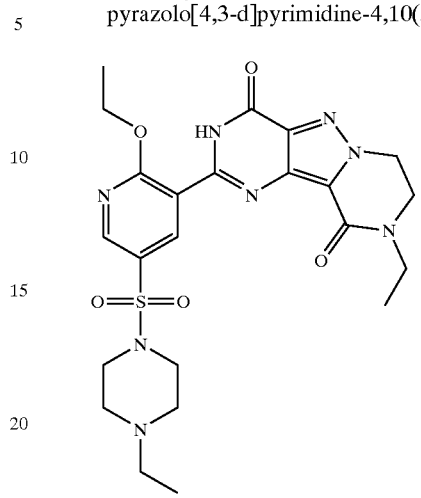

A mixture of the compound from preparation 62 (100 mg, 0.182 mmol), ethyl acetate (6 mg, 0.07 mmol) and potassium bis(trimethylsilyl)amide (91 mg, 0.46 mmol) in ethanol (7 ml) was heated at 130° C. for 2 hours in a sealed vessel. The cooled mixture was partitioned between ethyl acetate and saturated sodium bicarbonate solution, and the layers separated. The aqueous phase was extracted with ethyl acetate, the combined organic solutions dried (Na₂SO₄) and evaporated under reduced pressure. The crude product was purified by column chromatography on silica gel using an elution gradient of ethyl acetate:methanol:dichloromethane (90:10:0 to 0:10:90) to afford the title compound, 20 mg.

¹Hnmr (CDCl₃, 300 MHz) δ: 1.01 (3H, t), 1.26 (3H, t), 1.59 (3H, t), 2.40 (2H, q), 2.57 (4H, m), 3.16 (4H, m), 3.67 (2H, q), 3.86 (2H, t), 4.62 (2H, t), 4.78 (2H, q), 8.66 (1H, d), 9.19 (1H, d), 10.94 (1H, s).

Example 6

2-{5-[(4-Ethyl-1-piperazinyl)sulfonyl]-2-n-propoxy-3-pyridinyl}-7,8,9,10-tetrahydropyrido[2',1':5,1]pyrazolo[4,3-d]pyrimidin-4(3H)-one

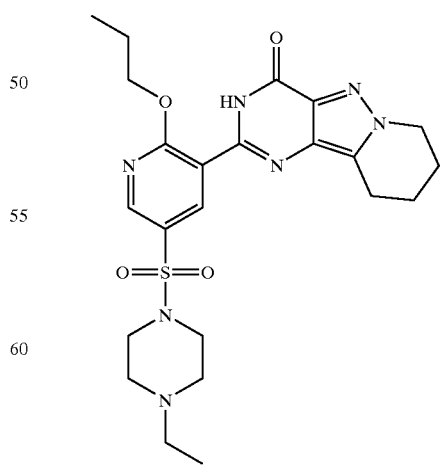

A solution of the title compound from example 2 (250 mg, 0.51 mmol) in n-propanol (20 ml) was heated to reflux, and some solvent allowed to evaporate off. The solution was cooled to room temperature, potassium bis(trimethylsilyl) amide (510 mg, 2.6 mmol) was added, and the reaction heated under reflux for 18 hours. The cooled mixture was concentrated under reduced pressure and the residue partitioned between dichloromethane and water. This mixture was neutralised using carbon dioxide pellets, the layers separated, and the aqueous phase extracted with dichloromethane (3×). The combined organic extracts were dried ($Na_2SO_4$) and evaporated under reduced pressure. The crude product was purified by column chromatography on silica gel using an elution gradient of dichloromethane:methanol (98:2 to 95:5), to afford the title compound as a solid, 130 mg.

$^1$Hnmr ($CD_3OD$, 300 MHz) δ: 1.02 (6H, m), 1.83 (2H, m), 2.00 (2H, m), 2.18 (2H, m), 2.41 (2H, q), 2.57 (4H, m), 3.10 (6H, m), 4.38 (2H, t), 4.54 (2H, t), 8.44 (1H, d), 8.64 (1H, d).

LRMS: m/z 502.2 (MH)$^+$

Found: C, 54.09; H, 6.27; N, 19.14. $C_{23}H_{31}N_7O_4S;0.5H_2O$ requires C, 54.10; H, 6.31; N, 19.20%.

Example 7

2-{5-[(4-Ethyl-1-piperazinyl)sulfonyl]-2-(2-methoxyethoxy)-3-pyridinyl}-7,8,9,10-tetrahydropyrido[2',1':5,1]pyrazolo[4,3-d]pyrimidin-4(3H)-one

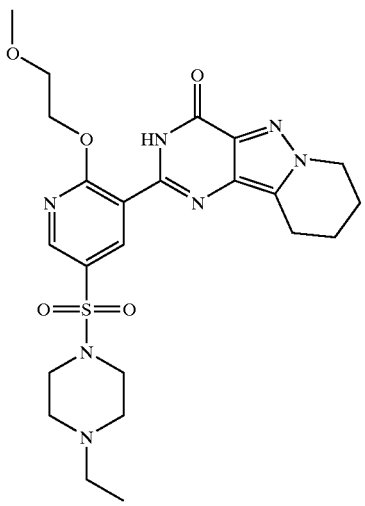

The title compound was obtained as a white solid (59%), from the title compound from example 2 and 2-methoxyethanol, using the procedure described in example 5.

$^1$Hnmr ($CDCl_3$, 300 MHz) δ: 1.00 (3H, t), 2.00 (2H, m), 2.18 (2H, m), 2.40 (2H, q), 2.56 (4H, m), 3.12 (6H, m), 3.57 (3H, s), 3.84 (2H, t), 4.40 (2H, t), 4.78 (2H, t), 8.60 (1H, d), 8.98 (1H, d), 10.80 (1H, s).

LRMS: m/z 518.1 (MH)$^+$

Found : 52.37; H, 6.11; N, 18.42. $C_{23}H_{31}N_7O_5S;0.5H_2O$ requires C, 52.45; H, 6.12; N, 18.62%.

Example 8

2-{5-[(4Ethyl-1-piperazinyl)sulfonyl]-2-n-propoxy-3-pyridinyl}-10-methyl-7,8,9,10-tetrahydropyrido[2',1':5,1]pyrazolo[4,3-d]pyrimidin-4(3H)-one

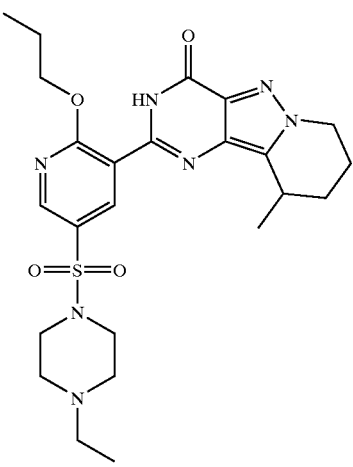

The title compound was obtained as a solid in 61% yield after recrystallisation from iso-propyl acetate, from example 3 and n-propanol, following the method of example 5.

$^1$Hnmr ($CDCl_3$, 300 MHz) δ: 1.01 (3H, t), 1.13 (3H, t), 1.60 (4H, m), 1.98 (2H, m), 2.08 (1H, m), 2.20 (2H, m), 2.41 (2H, q), 2.56 (4H, m), 3.15 (4H, m), 3.38 (1H, m), 4.32 (1H, m), 4.42 (1H, m), 4.61 (2H, t), 8.62 (1H, d), 9.02 (1H, d), 10.63 (1H, s).

LRMS: m/z 516.1 (MH)$^+$

Example 9

2-{5-[(4-Ethyl-1-piperazinyl)sulfonyl]-2-(2-methoxyethoxy)-3-pyridinyl}-10-methyl-7,8,9,10-tetrahydropyrido[2',1':5,1]pyrazolo[4,3-d]pyrimidin-4(3H)-one

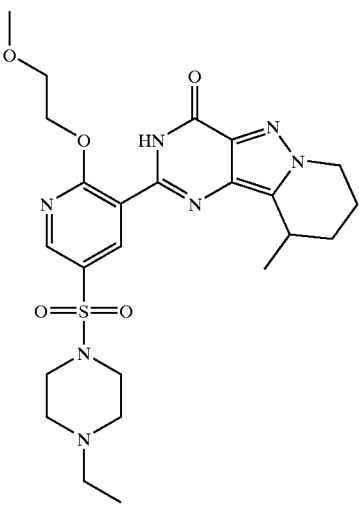

The title compound was obtained as a solid in 67% yield after recrystallisation from ethyl acetate, from example 3 and 2-methoxyethanol, following the method of example 5.

$^1$Hnmr ($CDCl_3$, 300 MHz) δ: 1.02 (3H, t), 1.58 (4H, m), 2.06 (1H, m), 2.20 (2H, m), 2.40 (2H, q), 2.56 (4H, m), 3.15

(4H, m), 3.37 (1H, m), 3.57 (3H, s), 3.85 (2H, t), 4.30 (1H, m), 4.42 (1H, m), 4.78 (2H, t), 8.60 (1H, s), 8.98 (1H, s), 10.78 (1H, s).

LRMS: m/z 532.2 (MH)+

Example 10

(9R)-2-{5-[(4-Ethyl-1-piperazinyl)sulfonyl]-2-(2-methoxyethoxy)-3-pyridinyl}-9-methyl-7,8,9,10-tetrahydropyrido[2',1':5,1]pyrazolo[4,3-d]pyrimidin-4(3H)-one;

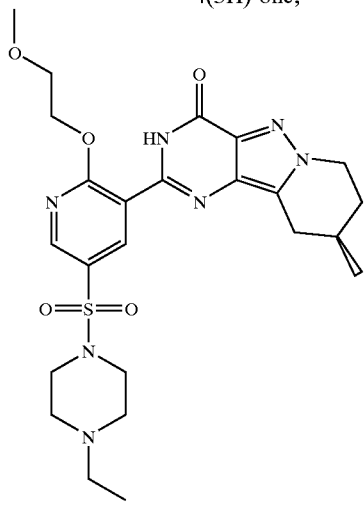

The title compound was obtained as a white solid, (61%), from the compound from example 4 and 2-methoxyethanol, following a similar procedure to that described in example 5.

$^1$Hnmr (CDCl$_3$, 300 MHz) δ: 1.01 (3H, t), 1.24 (3H, d), 1.88 (1H, m), 2.17 (2H, m), 2.41 (2H, q), 2.57 (4H, m), 2.61 (1H, m), 3.15 (4H, m), 3.36 (1H, m), 3.57 (3H, s), 3.86 (2H, t), 4.30 (1H, m), 4.56 (1H, m), 4.79 (2H, t), 8.60 (1H, d), 9.00 (1H, d), 10.80 (1H, s).

Example 11

2-[5-[(4-Ethyl-1-piperazinyl)sulfonyl]-2-(2-methoxyethoxy)-3-pyridinyl]-3,7,8,9,10,11-hexahydro-4H-pyrimido[5',4':3,4]pyrazolo[1,5-d]azepin-4-one

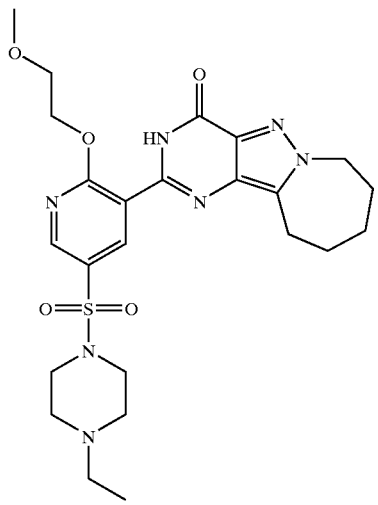

The product of preparation 59 (210 mg, 0.40 mmol) was stirred in 2-methoxyethanol (5 ml), potassium bis (trimethylsilyl)amide (420 mg, 2.1 mmol) was then added and the mixture heated to reflux under an air condenser and drying tube for 5.5 hours. The cooled mixture was concentrated under reduced pressure and the residue partitioned between dichloromethane and water. The aqueous phase was neutralised with solid carbon dioxide and further extracted with dichloromethane (×2). The organic phase was separated, dried (Na$_2$SO$_4$), filtered and evaporated under reduced pressure. The crude product was purified by column chromatography on silica gel using an elution gradient of dichloromethane:methanol (100:0 to 95:5) to afford the title compound, 100 mg.

$^1$Hnmr (CDCl$_3$, 400 MHz) δ: 1.05 (3H, t), 1.90 (6H, m), 2.40 (2H, q), 2.55 (4H, t), 3.15 (6H, s), 3.55 (3H, s), 3.85 (2H, t), 4.55 (2H, m), 4.80 (2H, m), 8.60 (1H, s), 9.00 (1H, s), 10.75 (1H, s)

LRMS: m/z 532.2 (MH)+

Found: C, 53.22; H, 6.29; N, 18.08 C$_{24}$H$_{33}$N$_7$O$_5$S;0.5H$_2$O requires C, 53.32; H, 6.34; N, 18.14%

Example 12

2-[5-[(4-Ethyl-1-piperazinyl)sulfonyl]-2-(2-methoxyethoxy)-3-pyridinyl]-11-methyl-3,7,8,9,10,11-hexahydro-4H-pyrimido[5',4':3,4]pyrazolo[1,5-d]azepin-4-one

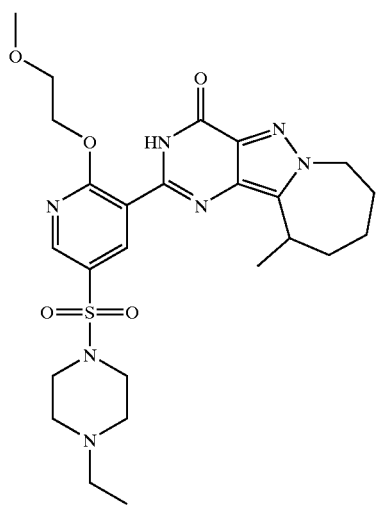

The title compound was obtained as a white solid in 60% yield, after trituration from ether, from the compound of preparation 60 and 2-methoxyethanol, following a similar procedure to that described in example 11.

$^1$Hnmr (CDCl$_3$, 400 MHz) δ: 1.04 (3H, t), 1.58 (3H, m), 1.82 (2H, m), 1.94 (2H, m), 2.07 (1H, m), 2.41 (2H, q), 2.57 (4H, m), 3.15 (4H, m), 3.50 (2H, m), 3.56 (3H, s), 3.85 (2H, t), 4.50–4.63 (2H, m), 4.78 (2H, t), 8.61 (1H, d), 8.98 (1H, d), 10.76 (1H, s).

LRMS: m/z 547 (MH)+

Example 13

2-{5-[(4-Ethyl-1-piperazinyl)sulfonyl]-2-n-propoxy-3-pyridinyl}-9-ethyl-8,9-dihydropyrazino[2'1':5,1]pyrazolo[4,3-d]pyrimidine-4,10(3H,7H)-dione

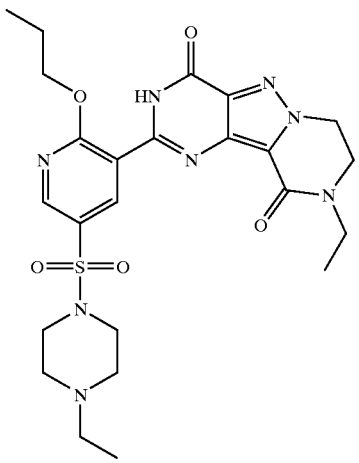

The title compound was obtained as a solid in 3% yield from the compound from preparation 62 and n-propanol, following a similar procedure to that described in example 5.

¹Hnmr (CDCl₃, 300 MHz) δ: 1.01 (3H, t), 1.15 (3H, t), 1.29 (3H, t), 2.00 (2H, m), 2.40 (2H, q), 2.56 (4H, m), 3.17 (4H, m), 3.70 (2H, q), 3.86 (2H, t), 4.64 (4H, m), 8.66 (1H, d), 9.20 (1H, d), 10.94 (1H, s).

Example 14

2-{2-n-Butoxy-5-[(4ethyl-1-piperazinyl)sulfonyl]-3-pyridinyl}-9-ethyl-8,9-dihydropyrazino[2', 1':5,1]pyrazolo[4,3-d]pyrimidine-4,10(3H,7H)-dione

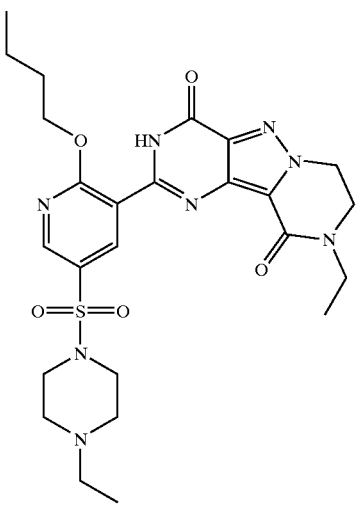

The title compound was obtained as a solid in 51% yield from the compound from preparation 62 and n-butanol, following a similar procedure to that described in example 5.

¹Hnmr (CDCl₃, 300 MHz) δ: 1.01 (6H, m), 1.28 (3H, t), 1.57 (2H, m), 1.96 (2H, m), 2.40 (2H, q), 2.56 (4H, m), 3.15 (4H, m), 3.68 (2H, q), 3.96 (2H, t), 4.65 (4H, m), 8.64 (1H, d), 9.18 (1H, d), 10.90 (1H, s).

Example 15

2-{2-n-Butoxy-5-[(4ethyl-1-piperazinyl)sulfonyl]-3-pyridinyl}-8,9-dihydropyrazino[2'1, ':5,1]pyrazolo[4,3-d]pyrimidine-4,10(3H,7H)-dione

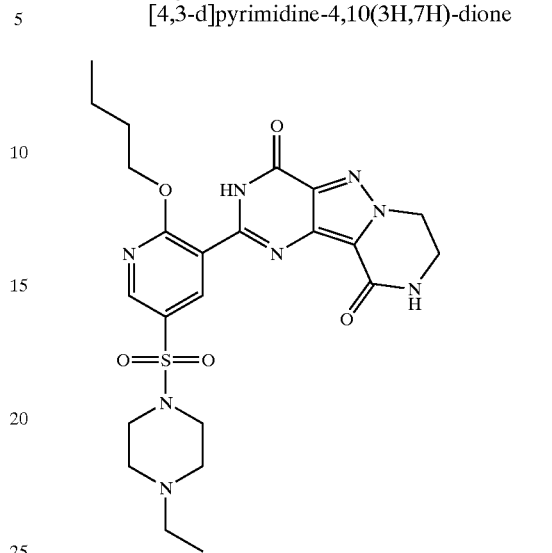

The title compound was obtained in 52% yield, from the compound from preparation 61 and n-butanol, following a similar procedure to that described in example 5.

¹Hnmr (CDCl₃, 300 MHz) δ: 1.01 (6H, m), 1.59 (2H, m), 1.96 (2H, m), 2.40 (2H, q), 2.55 (4H, m), 3.16 (4H, m), 3.96 (2H, m), 4.66 (4H, m), 6.60 (1H, s), 8.66 (1H, d), 9.16 (1H, d), 10.90 (1H, s).

Example 16

(−)-2-{2-Ethoxy-5-[(4-ethyl-1-piperazinyl)sulfonyl]-3-pyridinyl}-10-methyl-7,8,9,10-tetrahydropyrido[2', 1':5,1]pyrazolo[4,3-d]pyrimidin-4(3H)-one, and

Example 17

(+)-2-{2-Ethoxy-5-[(4-ethyl-1-piperazinyl)sulfonyl]-3-pyridinyl}-10-methyl-7,8,9,10-tetrahydropyrido[2', 1':5,1]pyrazolo[4,3-d]pyrimidin-4(3H)-one A sample of example 3 (150 mg) was purified by HPLC, using a Chiralcel OJ column and an eluant of hexane:ethanol:diethylamine (70:30:0.1), to give the title compound of example 16, 35 mg, ¹HNMR (CDCl₃, 300 MHz) δ: 1.02 (3H, t), 1.59 (7H, m), 2.02–2.28 (3H, m), 2.41 (2H, q), 2.57 (4H, m), 3.15 (4H, m), 3.38 (1H, m), 4.34 (1H, m), 4.43 (1H, m) 4.77 (2H, q), 8.62 (1H, d), 9.03 (1H, d), 10.65 (1H, s).

LRMS: m/z 501.3 (M)⁺

Found: C, 53.48; H, 6.28; N, 18.76. C₂₃H₃₁N₇O₄S.H₂O requires C, 53.15; H, 6.40; N, 18.87%.

And the compound of example 17, 27 mg.

¹HNMR (CDCl₃, 300 MHz) δ: 1.02 (3H, t), 1.59 (7H, m), 2.02–2.28 (3H, m), 2.41 (2H, q), 2.57 (4H, m), 3.15 (4H, m), 3.38 (1H, m), 4.34 (1H, m), 4.43 (1H, m) 4.77 (2H, q), 8.62 (1H, d), 9.03 (1H, d), 10.65 (1H, s).

LRMS: m/z 501.9 (M)⁺

[α]_D=+55.0° (c=0.1, methanol)

Found: C, 53.37; H, 6.24; N, 18.87. C₂₃H₃₁N₇O₄S.H₂O requires C, 53.15; H, 6.40; N, 18.87%.

Example 18

2-{5-[(4-Ethyl-1-piperazinyl)sulfonyl]-2-n-propoxy-3-pyridinyl}-10-methyl-7,8,9,10-tetrahydropyrido[2',1':5,1]pyrazolo[4,3-d]pyrimidin-4(3H)-one and

Example 19

2-{5-[(4-Ethyl-1-piperazinyl)sullenly]-2-n-propoxy-3-pyridinyl}-10-methyl-7,8,9,10-tetrahydropyrido[2',1':5,1]pyrazolo[4,3-d]pyrimidin-4(3H)-one A sample of example 8 (100 mg) was purified by HPLC using a Chiralcel OJ column and an eluant of hexane:ethanol:diethylamine (70:30:1), to give, after trituration from ether, the title compound of example 18, 9 mg, $^1$HNMR (CDCl$_3$, 400 MHz) δ: 1.00 (3H, t), 1.12 (3H, t), 1.59 (4H, m), 1.98 (2H, m), 2.08 (1H, m), 2.20 (2H, m), 2.40 (2H, q), 2.56 (4H, m), 3.16 (4H, m), 3.38 (1H, m), 4.32 (1H, m), 4.43 (1H, m), 4.62 (2H, t), 8.62 (1H, s), 9.02 (1H, s), 10.65 (1H, s).

LRMS: m/z 516.1 (MH)$^+$ and the compound of example 19, 13 mg.

$^1$HNMR (CDCl$_3$, 400 MHz) δ: 1.00 (3H, t), 1.12 (3H, t), 1.59 (4H, m), 1.98 (2H, m), 2.08 (1H, m), 2.20 (2H, m), 2.40 (2H, q), 2.56 (4H, m), 3.16 (4H, m), 3.38 (1H, m), 4.32 (1H, m), 4.43 (1H, m), 4.62 (2H, t), 8.62 (1H, s), 9.02 (1H, s), 10.65 (1H, s).

LRMS: m/z 516.1 (MH)$^+$

Example 20

(−)-2-{5-[(4-Ethyl-1-piperazinyl)sulfonyl]-2-(2-methoxyethoxy)-3-pyridinyl}-10-methyl-7,8,9,10-tetrahydropyrido[2',1':5,1]pyrazolo[4,3-d]pyrimidin-4(3H)-one and

Example 21

(+)-2-{5-[(4-Ethyl-1-piperazinyl)sulfonyl]-2-(2-methoxyethoxy)-3-pyridinyl}-10-methyl-7,8,9,10-tetrahydropyrido[2',1':5,1]pyrazolo[4,3-d]pyrimidin-4(3H)-one A sample of example 9 (89 mg) was further purified by HPLC using a Chiralpak AD 250 column and hexane:ethanol:diethylamine (70:30:1) as eluant to afford the title compound of example 20, 26 mg, $^1$HNMR (CDCl$_3$) δ:1.02 (3H, t), 1.58 (6H, d), 2.07 (1H, m), 2.20 (2H, m), 2.40 (2H, q), 2.55 (4H, m), 3.15 (4H, m), 3.38 (1H, m), 3.57 (3H, s), 3.86 (2H, t), 4.32 (1H, m), 4.42 (1H, m), 4.78 (2H, t), 8.61 (1H, d), 8.98 (1H, d), 10.77 (1H, s).

LRMS m/z: 532 (MH)$^+$

Found: C, 52.58; H, 6.32; N, 17.95. C$_{24}$H$_{33}$N$_7$O$_5$S.H$_2$O requires C, 52.44; H, 6.42; N, 17.84%.

And the compound of example 21, 16 mg.

$^1$HNMR (CDCl$_3$) δ: 1.02 (3H, t), 1.58 (6H, d), 2.07 (1H, m), 2.20 (2H, m), 2.40 (2H, q), 2.55 (4H, m), 3.15 (4H, m), 3.38 (1H, m), 3.57 (3H, s), 3.86 (2H, t), 4.32 (1H, m), 4.42 (1H, m), 4.78 (2H, t), 8.61 (1H, d), 8.98 (1H, d), 10.77 (1H, s).

LRMS m/z: 532 (MH)$^+$

[α]$_D$=+54.0° (c=0.1, methanol)

Found: C, 53.23; H, 6.32; N, 18.05. C$_{24}$H$_{33}$N$_7$O$_5$S.0.5H$_2$O requires C, 53.32; H, 6.34; N, 18.14%.

Example 22

2-(5-Acetyl-2-ethoxy-3-pyridinyl)-10-methyl-7,8,9,10-tetrahydropyrido[2',1':5,1]pyrazolo[4,3-d]pyrimidin-4(3H)-one

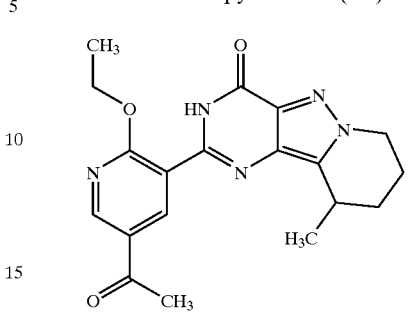

Cesium carbonate (507 mg, 1.56 mmol) and molecular sieves (spatula of) were added to a solution of the compound from preparation 64 (200 mg, 0.52 mmol) in tert-amyl alcohol (20 ml), and the mixture heated under reflux for 18 hours. The cooled mixture was concentrated under reduced pressure and the residue partitioned between dichloromethane (30 ml) and saturated sodium bicarbonate solution (25 ml). The layers were separated, the aqueous phase extracted with dichloromethane (2×30 ml), and the combined organic solutions washed with brine (30 ml), dried (MgSO$_4$) and evaporated under reduced pressure. The residual yellow solid was purified by column chromatography on silica gel using dichloromethane:methanol:0.88 ammonia (97.5:2.5:0.25) as eluant to afford the title compound as a white solid, 47 mg.

$^1$HNMR (CDCl$_3$) δ: 1.52 (t, 3H), 1.60 (m, 4H), 2.02 (m, 1H), 2.18 (m, 2H), 2.60 (s, 3H), 3.38 (m, 1H), 4.27 (m, 1H), 4.40 (m, 1 H), 4.70 (q, 2H), 8.80 (s, 1H), 9.21 (s, 1H), 10.65 (s, 1H).

LRMS: m/z (ES$^+$) 368 [MH$^+$]

Microanalysis found: C, 61.54; H, 5.75; N, 18.69. C$_{19}$H$_{21}$N$_5$O$_3$.0.2H$_2$O requires C, 61.51; H, 5.81; N, 18.69%.

Example 23

2-(5-Acetyl-2-isobutoxy-3-pyridinyl)-10-methyl-7,8,9,10-tetrahydropyrido[2',1':5,1]pyrazolo[4,3-d]pyrimidin-4(3H)-one

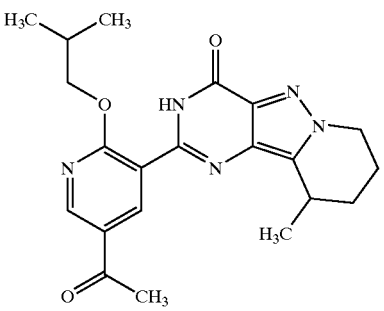

The title compound was obtained as a solid in 49% yield from the compound from preparation 64 and 2-methyl-1-propanol, following the procedure described in example 22.

$^1$HNMR (CDCl$_3$) δ: 1.16 (d, 6H), 1.65 (m, 4H), 2.02–2.38 (m, 4H), 2.66 (s, 3H), 3.41 (m, 1H), 4.35 (m, 1H), 4.46 (m, 3H), 8.86 (s, 1H), 9.25 (s, 1H), 10.78 (s, 1H).

LRMS: m/z (ES$^+$) 368 [MH$^+$]

Microanalysis found: C, 62.05; H, 6.26; N, 16.96. C$_{21}$H$_{25}$N$_5$O$_3$.0.6H$_2$O requires C, 62.08; H, 6.50; H, 17.24%.

What is claimed is:

1. A compound of Formula Iaa, having the formula:

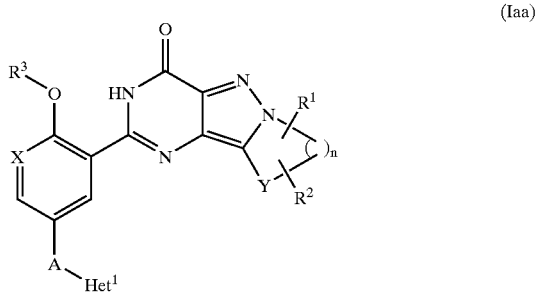

(Iaa)

or a pharmaceutically acceptable salt thereof wherein

A represents $SO_2$;

X represents N;

Y is $CH_2$;

n equals 3;

$Het^1$ represents a piperazinyl-1-yl group having a substituent $R^5$ at the 4-position of the piperazinyl group wherein said piperazinyl group is optionally substituted with one or two $C_1$ to $C_4$ alkyl groups and is optionally in the form of its 4-N-oxide;

$R^1$ and $R^2$ independently represent hydrogen; $C_1$ to $C_6$ alkyl; $C_1$ to $C_6$ alkoxy; $C_3$ to $C_6$ cycloalkyl; $C_3$ to $C_6$ alkenyl; phenyl; heterocyclyl containing one or more atoms from N, S or O, wherein each of the aforementioned substituents may be further substituted with a group selected from —CN, —$NO_2$, —$R^6$, —$S(O)_2R^6$; —$NR^4R^5$, —$OR^6$; —$OC(O)(C_1$ to $C_4$ alkyl); halo;

$R^3$ represents $C_1$ to $C_6$ alkyl optionally substituted with one or two substituents selected from $C_3$ to $C_5$ cycloalkyl, hydroxy, $C_1$ to $C_4$ alkoxy, benzyloxy, $NR^4R^5$, phenyl, $Het^2$, $Het^3$, $Het^4$ or $Het^5$ wherein the $C_1$ to $C_6$ alkyl and $C_1$ to $C_4$ alkoxy groups may be optionally terminated by a haloalkyl group such as $CF_3$ and wherein the $C_3$–$C_5$ cycloalkyl group may be optionally substituted by $C_1$–$C_4$ alkyl, hydroxy or halo; $C_3$ to $C_6$ cycloalkyl; $Het^2$, $Het^3$, $Het^4$ or $Het^5$;

$R^4$ and $R^5$ each independently represents hydrogen; $C_1$ to $C_4$ alkyl optionally substituted with $C_3$ to $C_5$ cycloalkyl or $C_1$ to $C_4$ alkoxy, or, together with the nitrogen atom to which they are attached, form an azetidinyl, pyrrolidinyl, piperidinyl or morpholinyl group;

$R^6$ represents hydrogen; $C_1$ to $C_4$ alkyl optionally substituted with one or two substituents selected from halo, hydroxy, $NR^4R^5$, $CONR^4R^5$, phenyl optionally substituted with $C_1$ to $C_4$ alkyl or $C_1$ to $C_4$ alkoxy; $C_3$ to $C_6$ alkenyl; $C_1$ to $C_4$ haloalkoxy; or $Het^5$;

$Het^2$ represents an N-linked 4-, 5- or 6-membered nitrogen-containing heterocyclic group optionally containing one or two further heteroatoms selected from S, N or O;

$Het^3$ represents a C-linked 5-membered heterocyclic group containing an O, S or N heteroatom optionally containing one or two further heteroatoms selected from N, O or S;

$Het^4$ represents a C-linked 6-membered heterocyclic group containing an O or S heteroatom optionally containing one or two further heteroatoms selected from O, S or N or $Het^3$ is a C-linked 6-membered heterocyclic group containing three N heteroatoms;

$Het^5$ represents a C-linked 4-, 5- or 6-membered heterocyclic group containing one, two or three heteroatoms selected from S, O or N; and wherein any of said heterocyclic $Het^2$, $Het^3$, $Het^4$ or $Het^5$ may be saturated, partially unsaturated or aromatic and wherein any of said heterocyclic groups may be optionally substituted with one or more substituents selected from $C_1$ to $C_4$ alkyl, $C_3$ to $C_4$ alkenyl, $C_1$ to $C_4$ alkoxy, halo , $COF_3$, $CO_2R^6$, $COR^6$, $SO_2R^6$, $NHR^6$ or $NHCOR^6$ and/or wherein any of said heterocyclic groups is benzo-fused.

2. A compound as claimed in claim 1, wherein $R^1$ represents hydrogen or $C_1$ to $C_6$ alkyl.

3. A compound as claimed in claim 1, wherein $R^2$ represents hydrogen or $C_1$ to $C_6$ alkyl.

4. A compound as claimed in claim 1, wherein $R^3$ represents $C_1$–$C_6$ alkyl optionally substituted by $C_1$–$C_6$ alkoxy.

5. A compound as claimed in claim 4, wherein $R^3$ is ethyl, n-propyl, n-butyl, i-butyl, or 2-methoxyethoxy.

6. A compound as claimed in claim 1, wherein piperazin-1-yl is substituted by $C_1$–$C_6$ alkyl.

7. A compound as claimed in claim 6, wherein $R^4$ is 4-ethylpiperazinyl, or 4-methylpiperazinyl.

8. A compound as claimed in claim 1 wherein $R^1$ and $R^2$ each independently represent hydrogen, $C_1$–$C_6$ alkyl or $C_1$–$C_6$ alkoxy.

9. A compound as claimed in claim 8, wherein $R^1$ and $R^2$ each independently represent hydrogen or $C_1$–$C_6$ alkyl.

10. A compound as claimed in claim 1, wherein $R^6$ represents a $C_1$ to $C_4$ alkyl group.

11. A compound as claimed in claim 1, wherein $R^3$ represents $C_1$ to $C_6$ optionally substituted by one or two $C_1$ to $C_4$ alkoxy groups.

12. A compound selected from the group consisting of:

2-{2-Ethoxy-5-[(4-ethyl-1-piperazinyl)sulfonyl]-3-pyridinyl}-7,8,9,10-tetrahydropyrido[2',1':5,1]pyrrolo[4,3-d]pyrimidin-4(3H)-one;

2-{2-Ethoxy-5-[(4-ethyl-1-piperazinyl)sulfonyl]-3-pyridinyl}-10-methyl-7,8,9,10-tetrahydropyrido[2',1':5,1]pyrrolo[4,3-d]pyrimidin-4(3H)-one;

(9R)-2-{2-Ethoxy-5-[(4-ethyl-1-piperazinyl)sulfonyl]-3-pyridinyl}-9-methyl-7,8,9,10-tetrahydropyrido[2',1':5,1]pyrrolo[4,3-d]pyrimidin-4(3H)-one;

2-{5-[(4-Ethyl-1-piperazinyl)sulfonyl]-2-n-propoxy-3-pyridinyl}-7,8,9,10-tetrahydropyrido[2',1':5,1]pyrrolo[4,3-d]pyrimidin-4(3H)-one;

2-{5-[(4-Ethyl-1-piperazinyl)sulfonyl]-2-(2-methoxyethoxy)-3-pyridinyl}-7,8,9,10-tetrahydropyrido[2',1':5,1]pyrrolo[4,3-d]pyrimidin-4(3H)-one;

2-{5-[(4-Ethyl-1-piperazinyl)sulfonyl]-2-n-propoxy-3-pyridinyl}-10-methyl-7,8,9,10-tetrahydropyrido[2',1':5,1]pyrrolo[4,3-d]pyrimidin-4(3H)-one;

2-{5-[(4-Ethyl-1-piperazinyl)sulfonyl]-2-(2-methoxyethoxy)-3-pyridinyl}-10-methyl-7,8,9,10-tetrahydropyrido[2',1':5,1]pyrrolo[4,3-d]pyrimidin-4(3H)-one;

(9R)-2-{5-[(4-Ethyl-1-piperazinyl)sulfonyl]-2-(2-methoxyethoxy)-3-pyridinyl}-9-methyl-7,8,9,10-tetrahydropyrido[2',1':5,1]pyrrolo[4,3-d]pyrimidin-4(3H)-one;

or pharmaceutically acceptably salts, solvates and polymorphs thereof.

13. A pharmaceutical composition including a compound of the claim 1 or a pharmaceutically acceptable salt thereof, together with a pharmaceutically acceptable excipient, diluent or carrier.

14. A method for the treatment of male erectile dysfunction (MED) or impotence comprising administering a therapeutically effective amount of a compound of claim 1 to a patient in need of such treatment.

* * * * *